US012293809B2

(12) United States Patent
Zavoronkovs et al.

(10) Patent No.: US 12,293,809 B2
(45) Date of Patent: May 6, 2025

(54) WORKFLOW FOR GENERATING COMPOUNDS WITH BIOLOGICAL ACTIVITY AGAINST A SPECIFIC BIOLOGICAL TARGET

(71) Applicant: INSILICO MEDICINE IP LIMITED

(72) Inventors: Aleksandrs Zavoronkovs, Pak Shek Kok (HK); Yan Ivanenkov, Moscow (RU); Daniil Polykovskiy, Moscow (RU); Aleksandr Aliper, Moscow (RU)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 1201 days.

(21) Appl. No.: 17/000,109

(22) Filed: Aug. 21, 2020

(65) Prior Publication Data

US 2021/0057050 A1 Feb. 25, 2021

Related U.S. Application Data

(60) Provisional application No. 62/891,050, filed on Aug. 23, 2019.

(51) Int. Cl.
| | |
|---|---|
| *G16C 20/50* | (2019.01) |
| *C07D 231/56* | (2006.01) |
| *C07D 245/04* | (2006.01) |
| *C07D 401/06* | (2006.01) |
| *C07D 401/12* | (2006.01) |
| *C07D 403/06* | (2006.01) |
| *C07D 403/10* | (2006.01) |
| *C07D 403/12* | (2006.01) |
| *C07D 409/12* | (2006.01) |
| *C07D 471/04* | (2006.01) |
| *C07D 471/10* | (2006.01) |
| *C07D 487/04* | (2006.01) |
| *C07D 487/10* | (2006.01) |
| *C07D 491/20* | (2006.01) |
| *C07D 513/10* | (2006.01) |
| *G06N 20/00* | (2019.01) |
| *G16C 20/40* | (2019.01) |
| *G16C 20/70* | (2019.01) |
| *G16H 10/20* | (2018.01) |

(52) U.S. Cl.
CPC ........... *G16C 20/50* (2019.02); *C07D 231/56* (2013.01); *C07D 245/04* (2013.01); *C07D 401/06* (2013.01); *C07D 401/12* (2013.01); *C07D 403/06* (2013.01); *C07D 403/10* (2013.01); *C07D 403/12* (2013.01); *C07D 409/12* (2013.01); *C07D 471/04* (2013.01); *C07D 471/10* (2013.01); *C07D 487/04* (2013.01); *C07D 487/10* (2013.01); *C07D 491/20* (2013.01); *C07D 513/10* (2013.01); *G06N 20/00* (2019.01); *G16C 20/40* (2019.02); *G16C 20/70* (2019.02); *G16H 10/20* (2018.01)

(58) Field of Classification Search
CPC ........ G16C 20/50; G16C 20/40; G16C 20/70; G16H 10/20; G06N 20/00; C07D 231/56; C07D 245/04; C07D 401/06; C07D 401/12; C07D 403/06; C07D 403/10; C07D 403/12; C07D 409/12; C07D 471/04; C07D 471/10; C07D 487/04; C07D 487/10; C07D 491/20; C07D 513/10

See application file for complete search history.

(56) References Cited

U.S. PATENT DOCUMENTS

| 5,767,144 | A | 6/1998 | Winn et al. |
| 2017/0161635 | A1 | 6/2017 | Oono et al. |

FOREIGN PATENT DOCUMENTS

| CN | 101115717 A | 1/2008 |
| CN | 102056927 A | 5/2011 |
| CN | 106146391 A | 11/2016 |
| CN | 109988151 A | 7/2019 |
| JP | 2011-509071 A | 3/2011 |
| WO | 9806874 A1 | 2/1998 |

(Continued)

OTHER PUBLICATIONS

Wang, et al, "Discovery and optimization of a series of 3-substituted indazole derivatives as multi-target kinase inhibitors for the treatment of lung squamous cell carcinoma" European Journal of Medicinal Chemistry vol. 163, Feb. 1, 2019, pp. 671-689 https://doi.org/10.1016/j.ejmech.2018.12.015.

(Continued)

*Primary Examiner* — Jerry Lin
(74) *Attorney, Agent, or Firm* — MASCHOFF BRENNAN

(57) ABSTRACT

A computer-implemented method can include: receiving input of a biological target; receiving a generative model (e.g., tensorial reinforcement learning (GENTRL) model or other model) trained with reference compounds, wherein the reference compounds include: general compounds, compounds that modulate the biological target, and compounds that modulate biomolecules other than the biological target; generating structures of generated compounds with the generative model; prioritizing structures of generated compounds based on at least one criteria; processing prioritized chemical structures of the generated compounds through a Sammon mapping protocol to obtain hit structures; and providing chemical structures of the hit structures. One or more non-transitory computer readable media are provided that store instructions that in response to being executed by one or more processors, cause a computer system to perform operations, the operations comprising performing the computer methods described herein for providing chemical structure of hit structures generated by the generative model.

16 Claims, 32 Drawing Sheets

(56) References Cited

FOREIGN PATENT DOCUMENTS

| WO | 0049539 | A1 | 8/2000 |
|---|---|---|---|
| WO | 2003074515 | A1 | 9/2003 |
| WO | 2005073189 | A1 | 8/2005 |
| WO | 2007081630 | A2 | 7/2007 |
| WO | 2007/139037 | A | 12/2007 |
| WO | 2011061548 | A2 | 5/2011 |
| WO | 203034048 | A1 | 3/2013 |
| WO | 2016161571 | A1 | 10/2016 |
| WO | 2019/018780 | A1 | 1/2019 |
| WO | 2019/100158 | A | 5/2019 |
| WO | 2019201297 | A1 | 10/2019 |
| WO | 2020079652 | A1 | 4/2020 |
| WO | 2020152067 | A1 | 7/2020 |

OTHER PUBLICATIONS

Wang, et al. "Design, synthesis, and biological evaluation of new B-RafV600E kinase inhibitors" Bioorganic & Medicinal Chemistry, vol. 26, Issue 9, May 15, 2018, pp. 2372-2380 https://doi.org/10.1016/j.bmc.2018.03.038.

Ren, et al. "Identification of GZD824 as an Orally Bioavailable Inhibitor That Targets Phosphorylated and Nonphosphorylated Breakpoint Cluster Region—Abelson (Bcr-Abl) Kinase and Overcomes Clinically Acquired Mutation-Induced Resistance against Imatinib" J. Med. Chem. 2013, 56, 3, 879-894.

Xu, et al. "Discovery of novel 4-amino-6-arylaminopyrimidine-5-carbaldehyde oximes as dual inhibitors of EGFR and ErbB-2 protein tyrosine kinases" Bioorganic & Medicinal Chemistry Letters vol. 18, Issue 12, Jun. 15, 2008, pp. 8495-3499 https://doi.org/10.1016/j.bmcl.2008.05.024.

International Search Report, PCT/IB2020/057884, Mailed Dec. 1, 2020.

Written Opinion, PCT/IB2020/057884, Mailed Dec. 1, 2020.

International Search Report, PCT/IB2020/057885, Mailed Nov. 30, 2020.

Written Opinion, PCT/IB2020/057885, Mailed Nov. 30, 2020.

Zhavoronkov, et al. "Deep learning enables rapid identification of potent DDR1 kinase inhibitors" Nature Biotechnology vol. 37, pp. 1038-1040, Sep. 2019, https://doi.org/10.1038/s41587-019-0224-x.

Maniyar, et al. "Data Visualization during the Early Stages of Drug Discovery" J. Chem. Inf. Model. May 26, 2006, 46, 4, 1806-1818, https://doi.org/10.1021/ci050471a.

Popova et al. "Deep reinforcement learning for de novo drug design" Science Advances Jul. 25, 2018: vol. 4, No. 7, eaap7885, DOI: 10.1126/sciadv.aap7885.

Ekins et al. "In silico pharmacology for drug discovery: applications to targets and beyond", British Journal of Pharmacology, vol. 152, Issue1, Jun. 4, 2007, pp. 21-37 DOI: 10.1038/sj.bjp.0707305.

European Patent Office; Extended European Search Report issued in EP App. No. 20857750.2 dated Aug. 3, 2023; 10 pages.

Sattarov B. et al.; "De Novo Molecular Design by Combining Deep Autoencoder Recurrent Neural Networks with Generative Topographic Mapping"; Journal of Chemical Information and Modeling; vol. 59, No. 3; Feb. 20, 2019; pp. 1182-1196; XP055731747; ISSN: 1549-9596; DOI: 10.1021/acs,jcim.8b00751.

Vamathevan J. et al.; "Applications of Machine Learning in Drug Discovery and Development"; Nature Reviews Drug Discovery, Nature Publishing Group; GB; vol. 18, No. 6; Apr. 11, 2019; pp. 463-477; XP036796445; ISSN: 1474-1776; DOI: 10.1038.S41573-019-0024-5.

Maniyar D.M. et al.; "Data Visualization during the Early Stages of Drug Discovery"; Journal of Chemical Information and Modeling; vol. 46, No. 4; pp. 1806-1818; DOI: 10.1021/ci050471a; XP055786036.

Japan Patent Office; Notice of Rejection issued in JP App. No. 2022-511189 dated Jul. 4, 2023.

Polykovskiy, Daniil; "Entangled Conditional Adversarial Autoencoder for de Novo Drug Discovery". Molecular Pharmaceutics, ACS Publications, 2018, pp. 4389 4405.

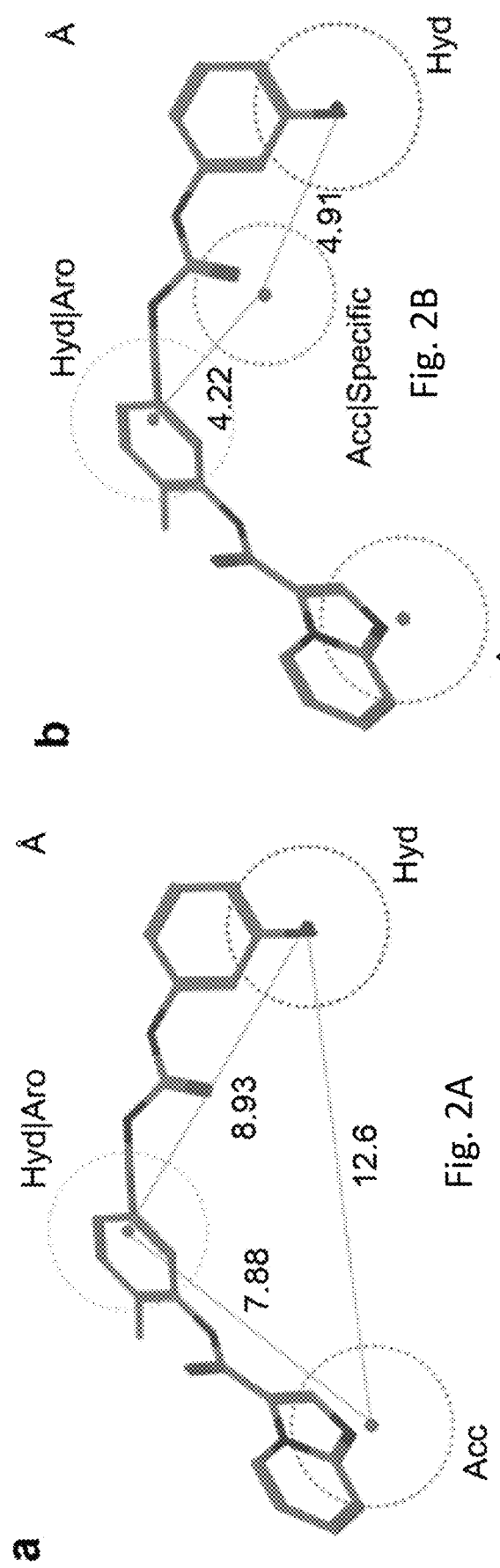

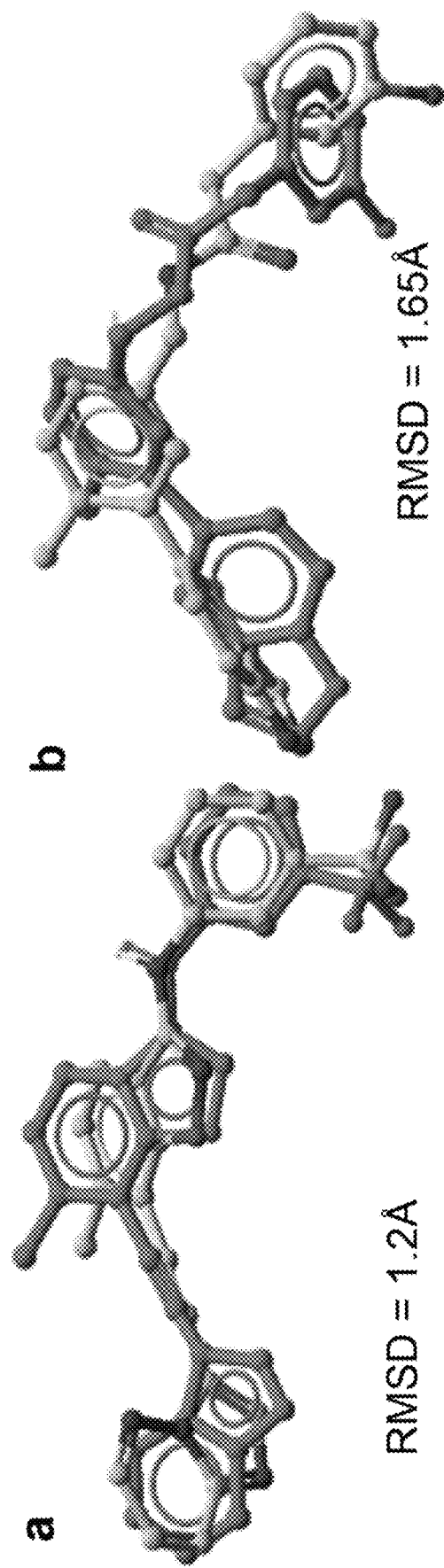
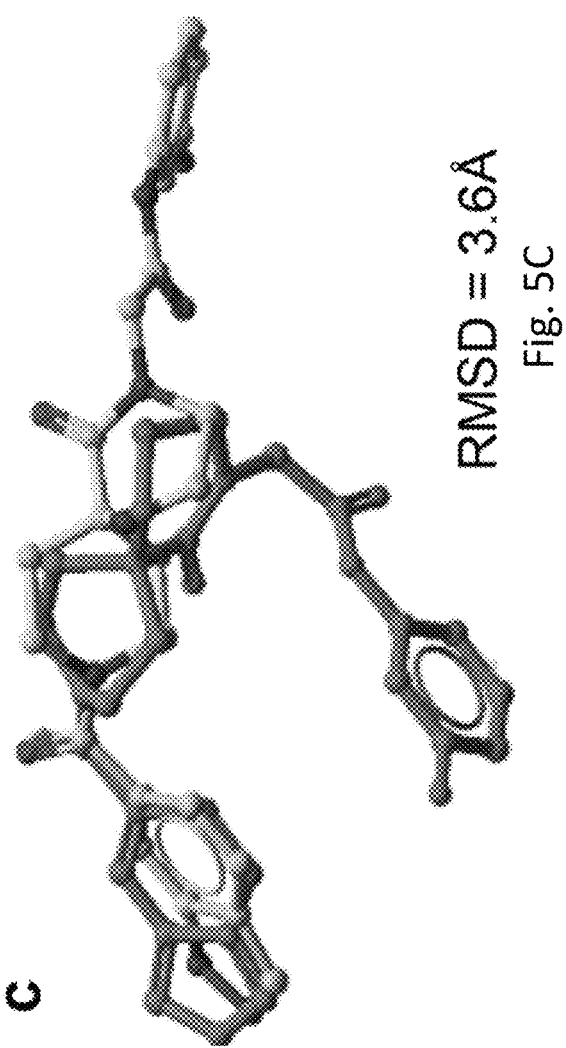
RMSD = 1.2Å
Fig. 5A
RMSD = 1.65Å
Fig. 5B
RMSD = 3.6Å
Fig. 5C

WORKFLOW FOR GENERATING COMPOUNDS WITH BIOLOGICAL ACTIVITY AGAINST A SPECIFIC BIOLOGICAL TARGET

CROSS-REFERENCE TO RELATED APPLICATIONS

This patent application claims priority to U.S. Provisional Application No. 62/891,050 filed Aug. 23, 2019, which provisional is incorporated herein by specific reference in its entirety.

BACKGROUND

Field

The present disclosure relates to workflow protocols for identifying a therapeutic target, acquiring background data, training models, generating structures, prioritizing compounds, synthesizing compounds, and biologically evaluating compounds in order to identify a compound that modulates the therapeutic target.

Description of Related Art

Drug discovery is a multidisciplinary field that requires seamless integration of several computational and experimental disciplines. The process typically involves a large number of compounds that are designed, synthesized and tested in an iterative, trial-and-error manner, with the majority of the compounds being discarded because of a lack of bioactivity, selectivity, physicochemical properties, poor pharmacokinetic (PK) profile, unacceptable toxicity or other problems. Recent advances in artificial intelligence (AI) and specifically in the generative adversarial networks (GANs), as well as reinforcement learning (RL), may help design novel compounds that are already placed within an acceptable safety and therapeutic window, thus, improving the likelihood of successful clinical trials.

The traditional discovery pipeline for new molecular entities (NME) or first-in-class drug is a complex, resource-consuming activity, which typically takes 10-20 years and costs between 0.5 to 2.6 billion USD per NME[1-3]. The uncertainty stems from reliance on assays with unknown clinical relevance and less than stringent critical assessment of available information. Failures in the preclinical stages, or during clinical evaluation, due to a lack of clinical efficacy, poor PK profiles, unacceptable toxicity and selectivity, continuously changing regulatory or commercial strategy positions, are leading causes of the increased costs of drug discovery[1]. Many drug candidates fail to reach clinical evaluation stages or gain regulatory approval. Smaller organizations struggle to advance innovative drug discovery projects of potential therapeutic importance beyond the early stages of development.

Many organizations engaged in drug discovery are exploring the integration and deployment of AI systems to bolster in-house research and development (R&D) programs for novel compounds, improved target bioactivity and selectivity, PK profile, toxicity, solubility, metabolic stability, synthetic accessibility, and other properties[4]. Despite skepticism regarding the potential impact of in silico models, A systems have progressed enormously in recent years across many fields of science and technology[5-7]. The breadth of AI applications extends from computer vision, voice and text analysis, route selection and autonomous driving, to healthcare diagnostics, drug discovery and biotechnology[8]. AI techniques can identify patterns hidden in huge volumes of data and perform reliable and sophisticated generalizations that traditional data analysis techniques could not achieve. Many experts in the field of drug discovery expect AI-driven instruments to become increasingly important and prominent in the near future[9-11].

One of the innovative A methods is the generative adversarial networks approach[12]. GANs have been used to "imagine" new photorealistic images, videos and music with the desired set of properties, and have the potential to generate chemical structures[13]. While the theoretical base for the GANs applications in drug discovery have exploded, there are few experimental examples demonstrating the ability to generate novel, diverse and effective small-molecule compounds. The early experiments in GANs utilized the binary fingerprint representation of the molecular structure[14,15] that needed to be matched to the known chemical space. The string-based representations allowed for the novel structures to be generated for synthesis[16-20]. Many studies focused on the graph and 3D structures[21] to allow new applications. Segler et al. extended the generative models with transfer and reinforcement learning and used the predicted binding affinity as an objective[22]. Merk et al. demonstrated the application of SMILES-based recurrent neural networks using transfer learning for the generation of active molecules[23,24]. Although recent AI developments have focused on de-novo molecular design, one of the main drawbacks is the absence of a full cycle of experimental validation: from the in silico design to chemical synthesis and biological evaluation.

Therefore, it would be advantageous to have an advanced, experimentally validated approach for the generation of novel, synthetically feasible compounds active against a biomolecular target.

SUMMARY

In some embodiments, a computer-implemented method can include: receiving input of a biological target; receiving a generative model (e.g., tensorial reinforcement learning (GENTRL) model) trained with reference compounds; generating structures of generated compounds with the generative model; prioritizing structures of generated compounds based on at least one criteria; processing prioritized chemical structures of the generated compounds through a Sammon mapping protocol to obtain hit structures; and providing chemical structures of the hit structures. In some aspects, the reference compounds include: general compounds, compounds that modulate the biological target, and compounds that modulate biomolecules other than the biological target.

In some embodiments, a computer-implemented method can include: receiving input of a biological target or ligand for any biological target (e.g., the biological target or other biological target); receiving input of properties of a generated compound; receiving at least one generative model trained with reference compounds; generating structures of generated compounds with each generative model, wherein the generated compounds are designed to interact with the biological target and/or correlate with structural features of the ligand; prioritizing structures of the generated compounds of each generative model based on at least one reward criteria; processing prioritized chemical structures of the generated compounds through a Sammon mapping protocol to obtain hit structures; and providing chemical structures of the hit structures.

In some embodiments, one or more non-transitory computer readable media are provided that store instructions that in response to being executed by one or more processors, cause a computer system to perform operations, the operations comprising performing the computer methods described herein for providing chemical structure of hit structures generated by the generative model.

In some embodiments, a computer system can include: one or more processors; and one or more non-transitory computer readable media storing instructions that in response to being executed by the one or more processors, cause the computer system to perform operations, the operations comprising performing the methods described herein for providing chemical structure of hit structures generated by the generative model.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 2A-2C show examples of performance of a pharmacophore hypothesis.

FIGS. 5A-5C show quantum mechanical calculations for a best fitted pharmacophore hypothesis.

Figure 1A:
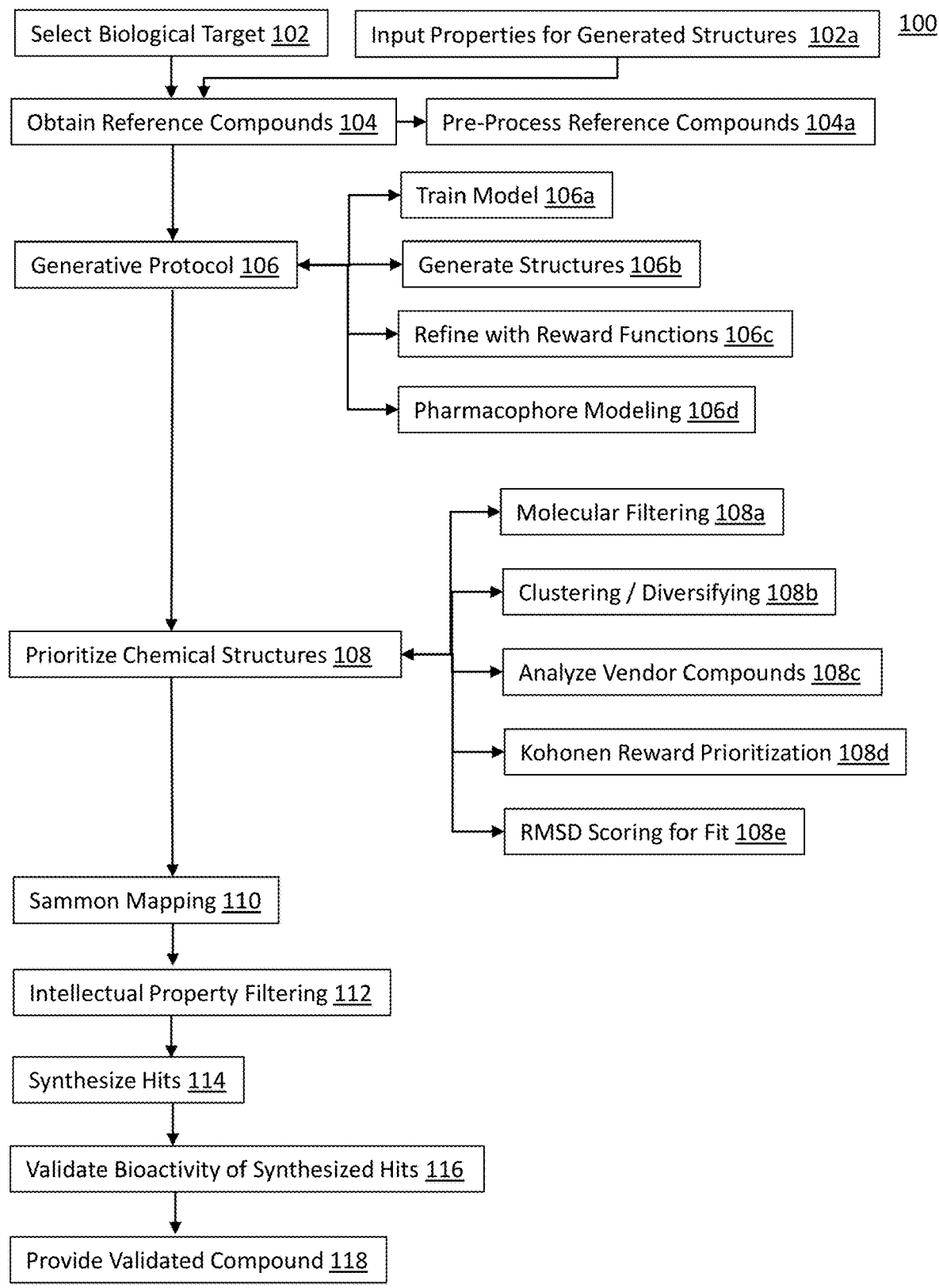
FIG. 1A shows an embodiment of a workflow for generating new compounds that are biologically active against a specific biological target.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to a workflow for generating compounds that have specific activity toward a biological target, such as the DDR1 or others. The workflow can include four connected components, which include: an input and configuration component; a generative component; a reward component; and an output component that outputs the generated compounds that have been prioritized by the reward component.

In some embodiments, the input and configuration component can be configured to receive and process input data of a biological target and input data of specified properties of a generated compound with specific activity on the biological target. The specific properties can include acceptable reward ranges for a reward component. For example, the specific properties can allow for the input data to specify acceptable physicochemical property, synthetic accessibility of a compound, and other properties that are evaluated in a reward and scoring protocol with an ensemble of modules.

In some embodiments, the generative component can include at least one model that is capable of generating compounds, such as compounds that with specific activity against the biological target. For example, the generative component can include up to 30 or more AI models, including GENTRL. GENTRL as an example of one of the generative models. However, the generative component of the workflow is suitable for many other different generative models with different architectures (e.g., GANs, genetic algorithms, RNNs, etc.).

In some embodiments, the reward component is configured to feed the reward linked to an individual generated compound back to the generative component to enable active learning. As such, the reward component includes all of the modules and their combinations for performing the reward prioritization. The reward prioritization allows for filtering out less preferred compounds. In some aspects, when each model (e.g., out of 30+) of the generative component generates a chemical structure, this individual structure is evaluated in the reward component. Depending on the generation time the workflow protocol can go through millions of generated and reward scored compounds.

In some embodiments, the output component is configured to select novel generated and scored chemical structures for the hit compounds. For example, a Sammon mapping protocol can be used for selecting the novel generated and scored chemical structures for the hit compounds.

In some embodiments, the present document shows experimental validation of small molecules designed using the generative adversarial networks (GANs). The present invention provides a generative tensorial reinforcement learning (GENTRL) model or other generative model or combinations of models for de novo drug design, which has been shown to be used to generate novel inhibitors of DDR1 kinase. In 21 days, the GENTRL model generated 6 compounds. Out of the hits, 2 compounds were low-digit nanomolar lead-like highly-active inhibitors that are new. Further biological and animal experiments confirmed anti-fibrotic activity, microsomal stability, and pharmacokinetics (PK) properties. Thus, the present invention can be used to generate compounds for specific activity (e.g., targeting specific protein) that can be synthesized and biologically validated.

In some embodiments, the workflow for the generative protocol can be formulated by combining: reinforcement learning[25-27], varational inference[28,29] and tensor decompositions[30-32], into an original generative, two-step machine learning algorithm. A first protocol is to generate an underlying manifold of a large number of the reported compounds. The second protocol expands the first protocol to discover new chemical scaffolds for compounds. The protocols can parameterize the structure of the learned manifold in the tensor train format[32] to use partially known properties (vide infra). By combining several approaches, the algorithm is quite robust: it avoids mode collapse, it uses partially labeled data, and it extrapolates the chemical space of molecules, thus suggesting novel valid structures which are not presented in the training libraries.

In some embodiments, the generative protocol that includes the GENTRL model avoids the drawbacks of generative models reported previously. The GENTRL can avoid the problems of GANS and avoid mode collapse. This overcomes a problem where GANs can suffer from mode collapse, namely they fail to suggest entire chemical classes of compounds attractive for drug discovery. Autoencoder-based generative models, such as variational autoencoders (VAE)[33] and adversarial autoencoders (AAE),[34] avoid mode collapse by compressing the space of structures onto a simply organized latent distribution that usually follows a standard Gaussian distribution. Simple latent distributions facilitate machine learning (ML) model training but may not be optimal mappings for the topology of the latent space for chemical structures. The proposed prior distribution used in the GENTRL model flexibly parametrizes the latent space in a high-dimensional lattice with an exponentially large number of multidimensional Gaussians in its nodes. This parametrization better ties the latent codes and properties, and works with missing values without explicitly imputing them (in contrast to other semi-supervised models[35]).

Previous reinforcement-learning-based approaches used reward functions that are less relevant for the generation of new structures because they used rather trivial rewards, for example the predicted n-octanol/water partition coefficient[36], traditional drug-likeness rules[37], and synthetic accessibility[18,38-39]. The current generative protocol uses self-organizing maps (SOMs)[40] to estimate how chemical structures relate to reported bioactive compounds (e.g., small-molecule kinase inhibitors), incorporating temporal structure-based trends observed in intellectual property for drug discovery. The method of the generative protocol employs the following three features: 1) Trending SOM (e.g., intellectual property trends); 2) General Biological Pathway SOM (E.g., general Kinase pathway); and 3) Specific Biological Target SOM (e.g., the specific Kinase, such as DDR1).

In some embodiments, the generative protocol uses the Trending SOM, which is a Kohonen-based reward function that discriminates "novel" compounds from "old" compounds considering the application priority date of chemical structures disclosed in relevant patents and published patent applications from any country, region or PCT. Compounds claimed during different time periods are located in distinct areas within the Kohonen map. Neurons abundantly populated with novel chemical entities have been used to positively reward the generative model, driving it closer to clusters that contain new molecules. The Trending SOM can be used in a protocol for any biological target.

In some embodiments, the generative protocol uses the General Kinase SOM, which is a Kohonen map that reliably distinguishes kinase inhibitors from other classes of molecules, guiding the ML engine towards kinase-biased structures. These two groups (e.g., kinase inhibitors versus other classes of molecules) are uniformly spread along distinct areas of the map, providing a statistically significant separation. Structures predicted as kinase inhibitors with the cell coefficient over 1.3 were then subjected to the specific Kohonen-based classifier, described below. For other biological targets, this General SOM can be a General Biological Target Family SOM.

In some embodiments, the generative protocol uses the Specific Kinase SOM, which has been trained to isolate DDR1 inhibitors from the total pool of kinase-targeted molecules. It was observed that DDR1 inhibitors were distributed within an ensemble of closely-related neurons at the periphery of the map. For other biological targets, this SOM can be a Specific Biological Target SOM In some embodiments, the generative protocol prioritized the generated structures using the above combination of three SOMs, thus at the final step placing more emphasis on nodes occupied by inhibitors of the biological target (e.g., DDR1 inhibitors). This results in obtaining chemical structures that are more likely to be specific inhibitors of specific biological targets.

In some embodiments, the present invention provides an accelerated workflow protocol 100 for generating chemical structures of compounds that have a specific activity against a biological target that is schematically depicted in FIG. 1A. FIG. 1A is a biological target based protocol that uses information of the biological target to design and generate compounds that interact with the biological target. The workflow protocol 100 includes selecting a biological target that is relevant to a disease or disorder or for any other biological reason where modulating the biological target can result in some benefit (Step 102). In an example, DDR1 kinase is selected as the biological target. Step 102a includes obtaining input of properties for the generated structures, which properties can range from physicochemical, pharmacochemical, responses to rewards or other properties that can be associated with a desired generated structure. Once the biological target is selected and properties input, the protocol 100 can identify reference compounds for use in training and compound generation with the generative model (Step 104). The reference compounds can include different groups of compounds, such as known inhibitors of the biological target (e.g., DDR1 kinase) that have ability to modulate the biological target above an upper modulation threshold, known inhibitors of other targets related to the biological target (e.g., general kinase inhibitors) that do not modulate the biological target or modulate the biological target below a lower modulation threshold, compounds that are not inhibitors of the biological target or related targets (e.g., non-kinase inhibiting compounds), compounds identified by retrosynthetic analysis (RSA), which facilitates synthesis of any resulting identified compound, and compounds identified by an analysis of an intellectual property (IP) database so that known compounds can be avoided and new compounds can be generated. The obtained reference compounds can be narrowed by pre-processing the reference compounds to remove unfavorable compounds (Step 104a), which can be unfavorable for various reasons, such as compounds having structures that are unfavorable for biological use or for synthesis, poor solubility, or gross outliers in structure. In some embodiments, the reference compounds can include general compounds, which can be those compounds that are known inhibitors of unrelated targets (e.g., receptors not in same family or class of the biological target receptor), compounds that are not known inhibitors of any targets, compounds having favorable medicinal chemistry properties, and compounds that are capable of being synthesized by a reasonable synthetic protocol.

Once the database includes the reference compounds, the generative protocol can be performed (Step 106), such as with the GENTRL model or other models of the workflow protocol 100. The generative protocol (Step 106) can include model training (Step 106a), structure generation (Step 106b), refining with reward functions (Step 106c), and pharmacophore modeling (Step 106d). The model training can be performed as well known in AI, where the generative models are trained with inputs from the reference compounds in the database. As such, an embodiment includes providing a trained generative model for each type of model. The trained generative models can each generate structures based upon the model training. The generated structures from all of the models can be refined by using the Kohonen SOMs, such as the trending SOM, general biological target family SOM, and specific biological target SOM. In some instances, the generated structures can be refined by excluding known or patented compounds, which is an assessment of novelty of the structures of the generated compounds. The pharmacophore hypothesis can be implemented with pharmacophore modeling to analyze structures for scaffolds or pendant groups that are responsible for biological or pharmacological interaction (e.g., modeling the structures with the biological target (e.g., modeling interaction of structure with the DDR1 kinase), such as docking, binding, dissociation, or other studies). The generative protocol (step 106) can then reduce the number of generated structures and refine the structures toward being novel and specific for the biological target.

Once the generative protocol has been implemented, the generated compounds are refined by a prioritization protocol (Step 108) that uses prioritization modules. Each prioritization protocol can include a module that performs the rewards and scoring, which modules are described herein. The prioritization protocol can implement molecular filtering to remove compounds that do not fit within certain reward criteria (Step 108a), which criteria can be defined and varied for different biological targets (e.g., see refine with reward functions step 106c). Also, the molecular filtering can be performed with medicinal chemistry filters (MCF) that filters out compounds that do not satisfy certain medicinal chemistry criteria. The MCF filter can include many (e.g., over 100) different substructure queries and analysis, where compounds that do not satisfy the criteria can be filtered out. The generated structures can also be processed with clustering analysis and diversity sorting procedures (Step 108b). In some instances, vendor databases can be compared to the generated structures so that structures that are the same or undesirably close to known compounds that are for sale can be filtered from the group of generated structures (Step 108c). The generated compounds can also be processed through the Kohonen SOMs again for prioritization (Step 108d), such as the general kinase SO and the specific kinase SOM, which provides additional prioritization of structures towards the potential inhibition of the biological target (e.g., DDR1 kinase). Models, such as pharmacophore modeling, crystallographic modeling, 3D pharmacophore modeling, and others can be used for obtaining an root-mean-square deviation value (RMSD), which reflects the degree of fit into the biological target (Step 108e).

The prioritized structures can then be processed through a Sammon mapping approach with the same set of descriptors as well as RMSD values that are output from the pharmacophore modeling (see Steps 106d and 108e). The Sammon map can be constructed and a number (e.g., defined or arbitrary) of specific compound structures can be selected.

In some embodiments, an optional additional intellectual property filtering may be performed to remove compounds that may be covered by a patent or subject to other intellectual property protection (Step 112). As a result, the remaining compounds can be novel and patentable compounds.

The remaining selected compounds are considered to be "hits" for the biological target, and the hits can then be synthesized (Step 114). The synthesis protocol can include analyzing the possible synthetic routes to obtain the compounds. Compounds that cannot be easily synthesized can be removed (e.g., see prioritization Step 108).

The synthesized hit compounds are then processed through assays to validate the biological activity on the biological target, such as modulation of activity of the biological target (Step 116). The types of assays vary depending on the biological target. For example, the synthesized hits can be assayed for binding and/or modulation of the biological target.

The hit compounds that are validated to have biological activity on the biological target can then be provided (Step 118). These compounds can be provided for further assessment, clinical trials, and potentially to patients for therapeutic treatment.

As an example, the AI-driven genesis of new molecules with nanomolar activity against DDR1 kinase can be performed as shown in FIG. 1A. The workflow protocol 100 can considerably reduce the timeframe needed for obtaining a compound that is validated to be biologically active on a biological target. The workflow protocol 100 uses a robustly tuned set of models for producing valid structures that medicinal chemists would consider to be tractable molecules. The starting point includes selecting a biological target of interest.

Figure 1B:
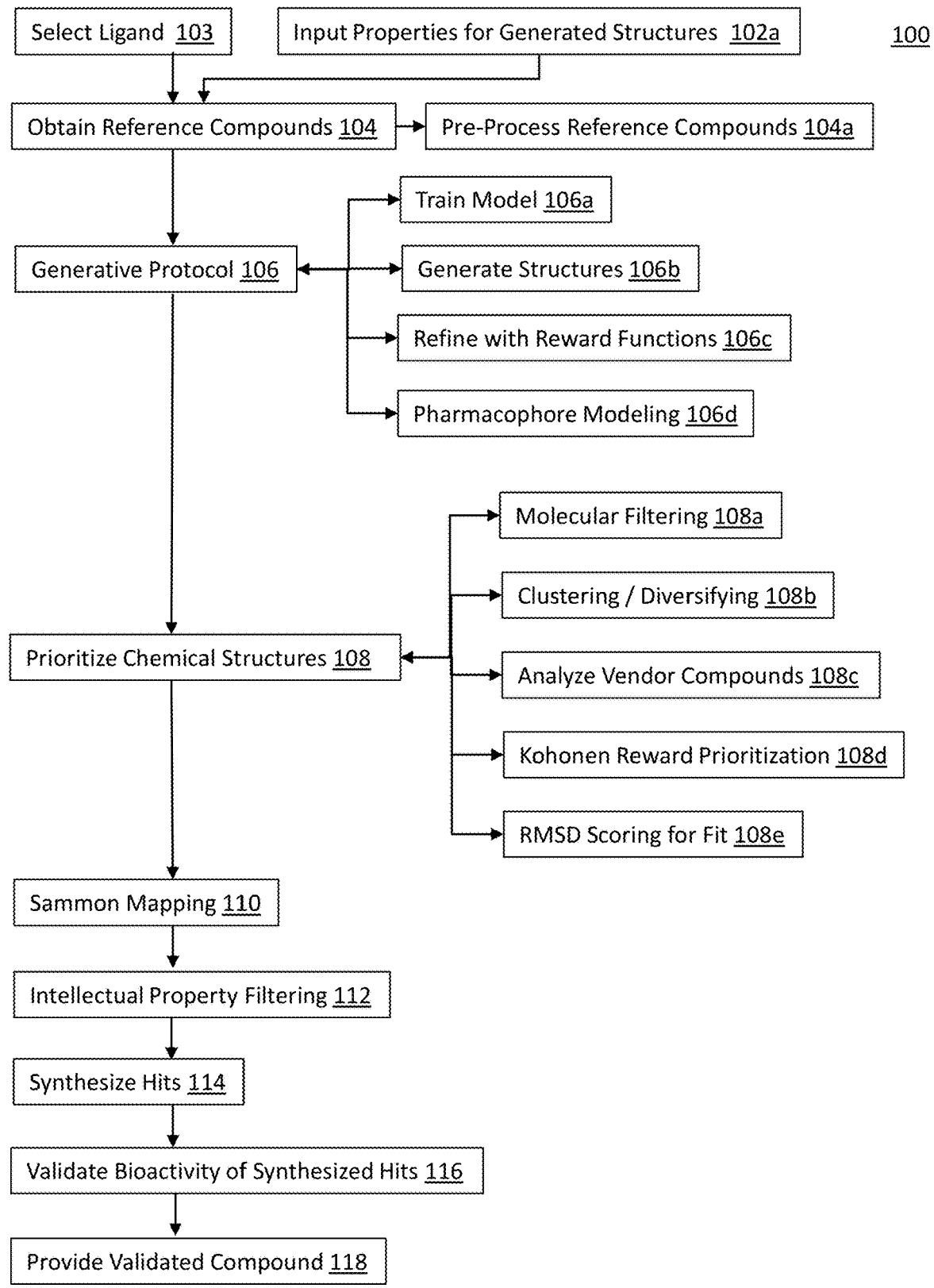
FIG. 1B shows an embodiment of a workflow for generating new compounds that match or correlate with a selected ligand (e.g., of a known biological target), such that generated compounds correlate with the 3D shape, space, hydrogen bonding, and other features of the selected ligand.

FIG. 1B includes a workflow protocol 100 that uses a ligand to design other ligands that match or correlate with the provided/selected ligand. In this workflow, the protocol creates chemical structures of potential ligands based on the chemical structures of the provided/selected ligand. Otherwise, the workflow in FIG. 1B follows the protocols of FIG. 1A, although focused on the structure of the provided/selected ligands in order to generate new potential ligands that would function similarly as the provided/selected ligand in order to have similar bioactivity, such as similar bioactivity to the same biological target, although the actual biological target is not specifically defined. However, the biological target may also be included in the step of receiving input of properties of a generated compound.

Accordingly, FIG. 1A includes a protocol for analyzing the biological target, such as the binding pockets or other binding features, for generating chemical structures that bind therewith as ligands. FIG. 1B includes a protocol for analyzing a ligand for a biological target, such as analyzing the 3D structure, hydrogen boding, etc., and using the ligand information to design additional potential ligands with similar shape or 3D presence, with similar binding features for binding with the same biological target.

The biological target can be selected as an example of an appropriate biological target that met initial criteria, which were: a) this target must be validated, or at least implicated in a disease or disorder or other condition (e.g., fibrosis) and should be classified as relatively novel in this application; b) the reference dataset should contain a low to moderate (but sufficient) number of molecules to assess the "cognitive" skills of the generative model. For example, 5 datasets can be used: 1) small-molecule compounds with inhibition activity against the biological target (e.g., DDR1 kinase); 2) a common database of reported inhibitors (e.g., kinase inhibitors) as a positive control set; 3) molecules acting on other unrelated biological targets (e.g., non-kinase targets) as a negative control set; 4) patent data for biologically active molecules claimed by the top pharmaceutical companies arranged by the priority date; and 5) structure data (e.g., X-Ray diffraction data) published for the known inhibitors of the biological target, such as DDR1 inhibitors in an example. An $IC_{50}$ value of 1 μM can be selected as a threshold for classifying reference molecules as active or not active. The databases 2) through 4) can then preprocessed to exclude gross outliers and normalize the input chemical space by reducing the number of compounds containing similar structure per each cluster.

The generative protocol can provide modeling techniques that can produce and analyze immense amounts of data based on available information and pinpoint the inferred and objective relationships hidden in the studied phenomena. In drug discovery, deep learning algorithms of GENTRL or other models can put chemical data in precise context and uncover deeply buried patterns that are otherwise invisible, yet potentially valuable for medicinal chemists. Accordingly, the workflow protocol offers part of the solution to address this sector's widely recognized declining productivity-cost balance. This workflow demonstrates that the generative models are maturing quickly and are likely to become mainstream tools for de novo hit and lead generation, in addition to solving many other challenges in pharmaceutical research and development.

In some embodiments, the generative models can be used in methods for de novo design of compounds for the creation of novel chemical entities with desired properties (e.g., pharmacological activity). The workflow protocol can begin with the identification of the most appropriate biological target based on the knowledge of the disease mechanisms. The first step of the design procedure is to identify a set of lead compounds to be optimized. The most promising hits (e.g., compounds) are selected and their property profiles undergo further optimization. Finally, an effective method for the synthesis of the final drug compound can be established. Although standard design methods have the capabilities to create molecular structures that are often synthesizable within a few reaction steps, these methods suffer from the fact that they often rely on explicit chemical knowledge accumulation in the form of synthesis rules or basic physical models. The generative models can identify patterns within complex, nonlinear data in an automatic fashion without the need for manual feature engineering.

In an example generative model, the GENTRL model operates on a AI-based platform that combines ML and deep learning (DL) models (GANs, Autoencoders, RNN-based language models, Genetic algorithms, combinatorial approaches, Ensembles). These methods are combined with the RL optimization and integrated into an end-to-end pipeline (FIGS. 1A-1B). In practice, once the user has entered all required information, the generative protocol begins with up to 30 models running in parallel. The average duration for a standard generation experiment is around 72 hours. The interface allows following the progress of the generation process together with the performance and convergence rate of each model in real time. All molecules which are progressively being generated can be compared in terms of various metrics using the interactive capabilities of the user interface.

In further reference to FIGS. 1A-1B, the workflow protocol can use 2D models with first line filters for generated compounds and the SOM filtering of generated compounds for reward and scoring. The first line filters can include the following modules: MCE-18; MCFs; ROG5, T-indexes, Similarity; Diversity; physicochemical (PC) profile; Drug-likeness, Privileged Fragments; Synthetic accessibility (SA) score; and clustering. The SOM filtering can include: Hierarchical Active Molecules (HAM) dataset; Parent SOMs; and Zoom Maps.

Additionally, the reward and scoring for 3D models can include: Conformation Generation (3D conformations, minimization, flex score); Descriptors (similarity to template molecule); Pharmacophore modeling (pharmacophore hypothesis, searching); shape analysis (shape similarity); Pocket analysis (binding affinity, pocket identification and scoring). Further structure morphing can be implemented, such as metabolic stability enhancements, and bioisosteres (chemical substituents or groups with similar physical or chemical properties which produce broadly similar biological properties to another chemical compound).

In some embodiments, once all required information has been entered, the generation begins with up to 30 models running in parallel in the generative component. The input can include 2D or 3D structures (sdf or mol), x-ray data (target, pocket of binding), and target name. The reference database, such as for training, can be input. The different AI models can also be identified and input into the system. The average duration for a standard generation experiment is around 72 hours. The interface allows following the progress of the generation process together with the performance and convergence rate of each model in real time. For example, the progress can be shown on a computer display. All molecules which are progressively being generated can be compared in terms of various metrics using the interactive capabilities of the user interface.

Regarding FIGS. 1A-1B, the workflow protocol operates with a platform that includes more than 30 advanced DL models with multiple generative paradigms based on multiple molecular representations, such as 3D, graph and string representations. Training, validation and model selection as well as benchmarking and evaluation procedures for reward components are automatized and a set of integral metrics are integrated for assessing the quality of generations. Novelty and diversity of the molecules are encouraged through the use of improved reward functions which penalize molecules similar to known structures and promote exploration of novel chemical spaces. This includes a method for designing a novel and diverse set of structures as starting points for future generations and multiple tools for designing, scoring, filtering and ranking molecular conformers with 3D reward functions. Two SA scores are implemented to prioritize molecular structures according to their synthesis accessibility. See FIG. 10B.

Figure 10A:
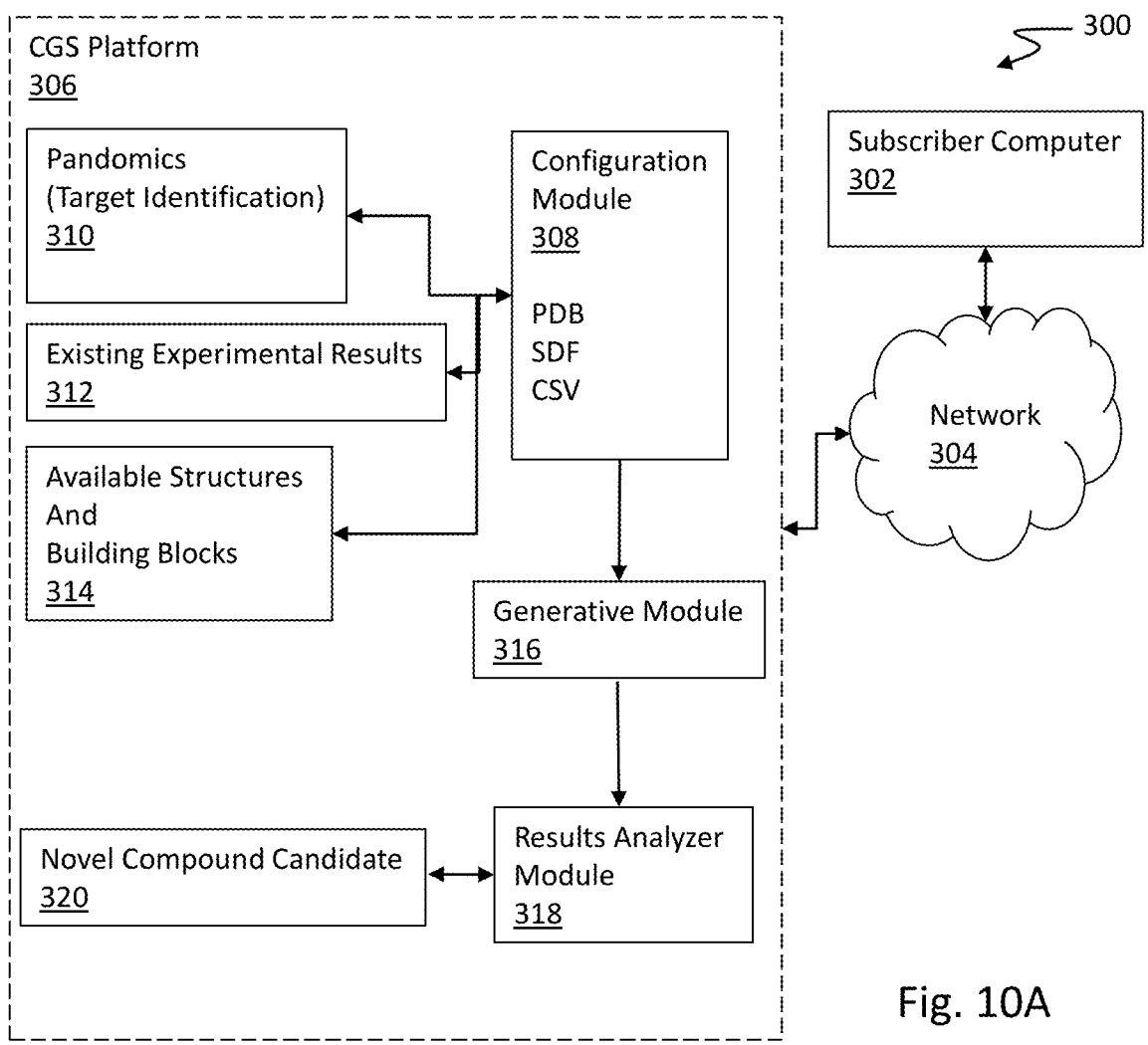
FIG. 10A illustrates a schematic example of a chemical generating system platform in accordance with the workflow protocol.
Figure 10B:
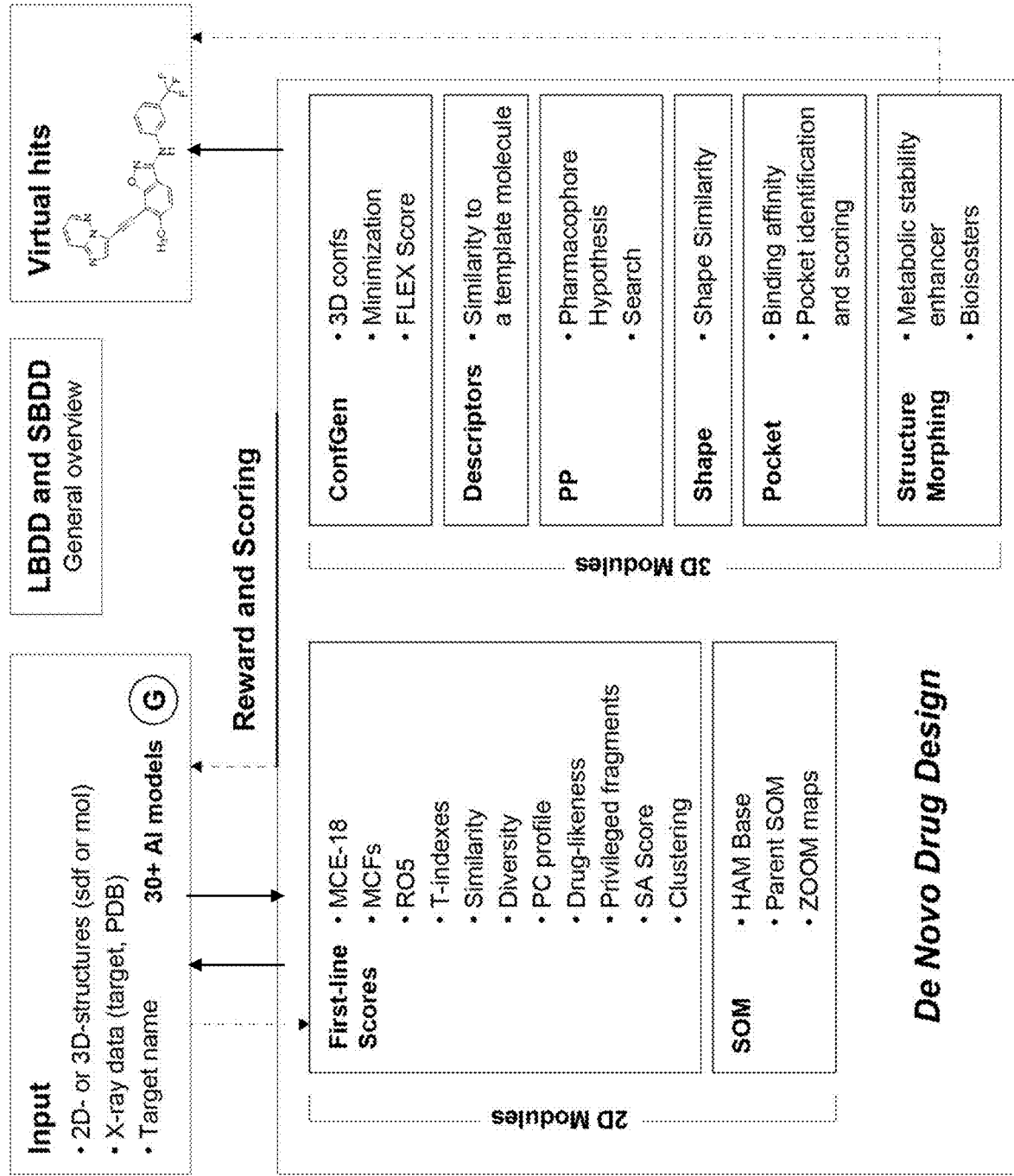
FIG. 10B illustrates an example of a workflow for operating with the generative model.
Figure 10C:
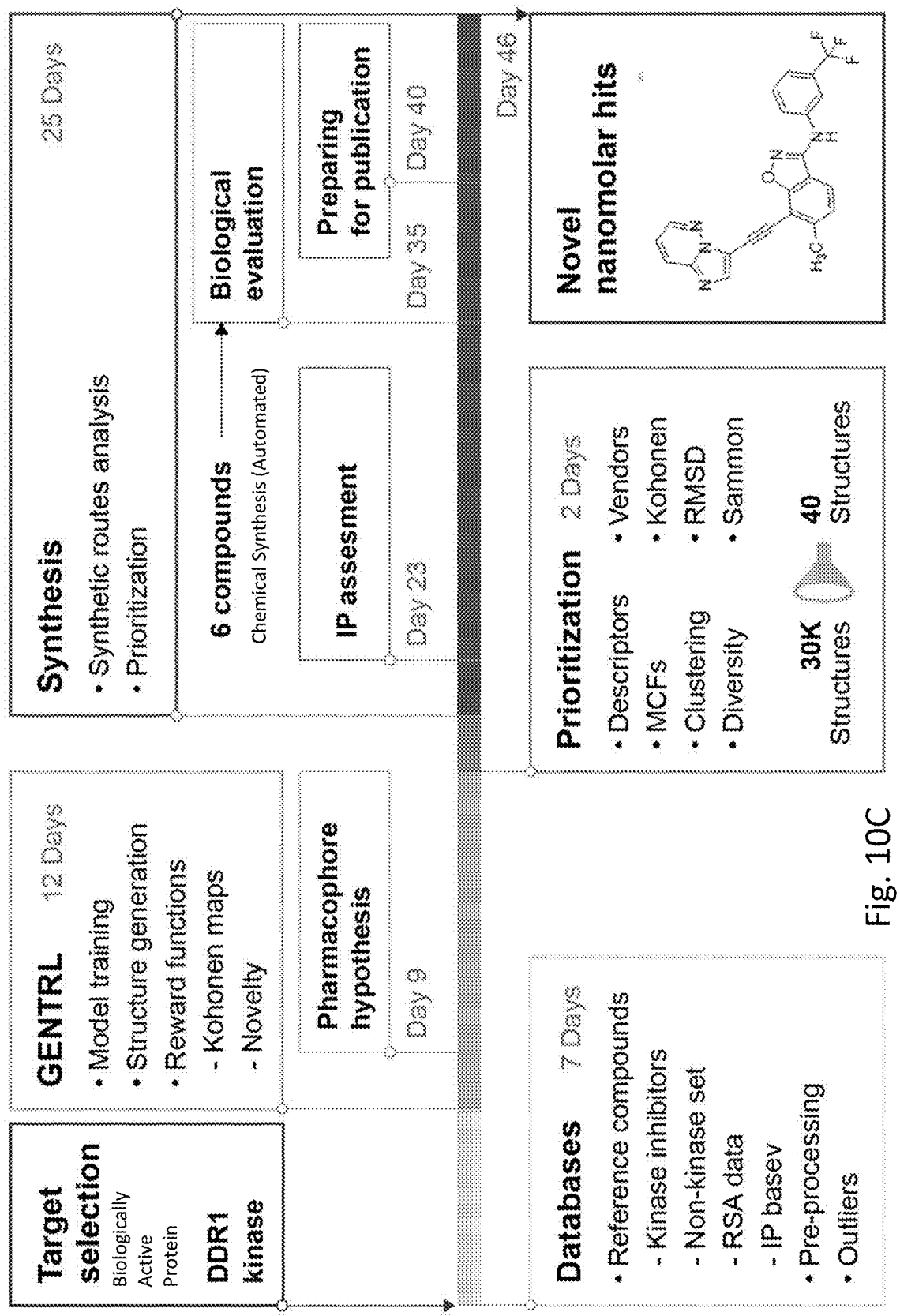
FIG. 10C illustrates an example of a workflow for operating with the generative model.

FIG. 10B shows an example of a workflow that can be operated with the system of FIG. 10A. The workflow shows the input component and models used for the de novo drug design with the first-line scores and SOM for 2D modules, and with the Confgen, Descriptors, PP, Shape, Pocket, and Structure Morphing for 3D modules. The rewards and scoring are used for generating compounds with improved properties, which are provided as virtual hits. FIG. 10C shows an example timeline of using the FIG. 10B workflow.

The compound generation through RL involves two distinct classes of rewards and scoring—2D modules and 3D modules. The set of 2D modules is made of two categories. The first category is the set of first-line filters which includes different filtering modules that perform different filtering methods, such as by rewards and scoring. Some of the modules are described below. The MCE-18 module is a unique molecular descriptor filter to score structures in terms of medicinal chemistry evolution. Medicinal chemistry filter (MCFs) modules are composed of around 460 MCFs can be used to filter for compounds that satisfy medicinal chemistry needs, which are used to exclude unsuitable compounds containing structure alerts (e.g. reactive, unstable, toxic, etc.). The Lipinski's Rule of Five (RO5) module performs a filtering based on that poor absorption or permeation is more likely when there are more than 5H-bond donors, 10H-bond acceptors, the molecular weight is greater than 500, and the calculated Log P (C Log P) is greater than 5. The T-indexes modules constitutes a set of rules to eliminate structures with an unbalanced number of carbons and heteroatoms. The similarity scores module can be used for the assessment of 2D-similarity between the generated structures and the available chemical space. The pharmacochemical or physicochemical (PC) profile module assesses compounds using a set of molecular descriptors, such as Log P, PSA, HBD, HBA, molecular weight (MW), or the like. The drug-likeness module filtering is estimated using extended rules for drug-likeness estimation. Other important filter modules in this category are based on the privileged fragments (PFs). PFs are the substructures that are statistically more common for the molecules active against a selected target or a target class than for the rest biological targets. The privileged structure module has an automatic prioritization of fragments, which are useful for a selected class of compounds or biological targets. The PF filters analyzing PFs automatically prioritize fragments considered as essential for a specific class of compounds or target. PFs are automatically identified based on Hierarchical Active Molecules (HAM) dataset. HAM is a wide dataset of biologically active molecules with the reported in vitro activities against various targets (IC50<10 μM, ~4M records) and are integrated within the second category of filters containing the self-organizing maps (SOM). The synthetic accessibility (SA) score and Retrosynthesis Related Synthetic Accessibility (ReRSA) modules are used as filters to assess the SA of the generated structures. ReRSA is an improved fragment-based SA estimation method. The idea of fragment presence in large databases was taken from the SA score method, but the fragmentation method differs significantly. ReRSA score is based on more thoughtful fragmentation from the organic synthesis perspective, and that helps to estimate SA more accurately. The diversity module performs filtering by a main diversity that calculated for all the generated structures using the proprietary FPs. A set of rules based on FPs are also used to cluster the generated structures with a cluster module.

The second class of reward functions can include a number of different 3D modules. In an example, the second class can include up to five categories of 3D modules. The first category of 3D modules includes ConfGen, FLEXScore and Minimization. To begin, an ensemble of different conformations is generated. A set of rules with the pre-defined substructure geometries is implemented based on X-Ray data. The FLEX Score module is used to rank and select the structures by rigidity (using the binding entropy factor). The second category of filters contains a set of 3D-descriptors which aims at providing an assessment of 3D-similarity between the generated structures and the reference molecules.

The third category of filters relate to the pharmacophore hypothesis and search, and includes 3D-pharmacophore hypothesis construction with the potential binding points and also with settings on distances, angles and tolerance followed by the automatic assignment of potential structures and visualization. The fourth category contains filters using the shape similarity as an assessment of the 3D-shape similarity to a reference molecule. This includes the shape scoring for the pharmacophore alignment. The last category of filters focuses on the pocket identification and scoring.

In some embodiments, metabolic stability enhancer modules are used to enhance the metabolic stability of the generated compounds. The potential sites of metabolism are identified, and these sites are replaced by more stable fragments or groups of chemical structures.

In some embodiments, 3D descriptor similarity modules are used for a rough assessment of the 3D similarity between the generated structures and the reference molecules in terms of the 3D molecular descriptors. This can be a shape similarity for the assessment of 3D shape similarity to a reference molecule. There is a shape scoring for pharmacophore alignment.

In some embodiments, the pharmacophore hypothesis module can include 3D construction and modeling with the target protein. The identified binding sites of the generated compound are evaluated. Valuable settings on distances or angles or tolerance can be placed on the generated compounds to filter unacceptable compounds.

In some embodiments, a pocket identification and scoring module can be used to scan pockets of the biological target to identify potential binding sites. The scanner can be for de novo or template-based grid mapping. An ultra rapid binding affinity assessment can be performed for the generated structures. Hydrogen bonds, clashes, and repulsive features can be avoided. Mandatory binding points can be identified. The module can use validation by x-ray co-crystal data. The pocket results can be similar to data obtained from docking studies. Additionally, volume increment scoring can be performed.

In some embodiments, the present technology includes development and application of AI-based algorithms for de novo design of compounds. The AI protocols allow for the ability to compare and estimate the performance of models and to assess the properties of the generated molecules. Comparison of DL-models is challenging and requires specific benchmarks and metrics because the training parameters and architecture hyper-parameters can significantly alter the performance.

In some aspects, Molecular Sets (MOSES) can be used. The MOSES can be designed as a benchmarking platform to support research on DL for drug discovery by making available a set of molecular generative models and metrics for evaluating the novelty and quality of the generated molecules. Those approaches are integrated within the AI platforms described herein. These features allow users to keep record of results, codes, training data and any information required to ensure that experiments can be reproduced without having to go through a manual saving process. Working within such a working environment is important especially when doing research experimentation which requires either testing variations of the same model or investigating the relative performance of different models using different sets of training data.

In some embodiments, the protocols described herein can be used to provide metrics to estimate the novelty and diversity of the generated molecules, based on distance metrics in the chemical space. The novelty and diversity assessment of the molecules is performed using different approaches including automated preprocessing of training data that maximizes novelty and diversity efficiency and methods for dynamic novelty and diversity optimization through generative optimization rather than filtering.

In some embodiments, the protocols described herein can be implemented on a distributed cloud platform with scalable cloud architecture, such as being run on Amazon Web Services (AWS). The implementation integrates a variety of features aiming at optimizing its performance and improves the user experience. This includes cluster management with Kubernetes, multiple flexible workflows, automated C/CD, integrated monitoring and logging. The integrated nature of the GENTRL platform allows its deployment on the cloud or on-premise. In the case of a deployment on-premise, the platform can be easily integrated within an already operational workflow.

FIG. 10A show an embodiment of a system for implementing a compound generating protocol. A subscriber computer 302 is connected through a network 304 to compound generating system (CGS) platform 306. The CGS platform 306 can be configured as a small molecule generative chemistry platform that allows for exploration of compounds with an automated machine learning platform, and that can access structure-based design and ligand-based design of drugs, which can be used to generate novel and diverse molecules for protein targets of interest. The subscriber computer 302 uploads subscriber data to an input module 308 of the CGS platform 306. For example, the subscriber data can include structural data of one or more compounds, whether related or different, which can be starting points for compound generation. The subscriber computer 302 uploads information for a desired outcome into the configuration module 308, which desired outcome can include an outline of desired outcome from the platform (e.g., with web interface or via an API). The desired outcome can be a molecule that interacts with a specific biological target (e.g., DDR1) or is active for treating a specific disease (e.g., fibrosis). The configuration module 308 then interfaces with pandomics 310, and obtains the relevant protein information (e.g., target identification). Pandomics 310 is a multi-omics target discovery and deep biology analysis engine, which can utilize published omics data and decipher the same, analyze any omics data type, evaluate drug target proteins, and get strategies for drug repurposing. Pandomics provides access to information ranging from disease signatures to prospective targets and molecular candidates. Pandomics combines classic bioinformatics tools such as signaling pathway analysis using iPANDA. The configuration module 308 can obtain existing experimental results data 312, such as from a database or from the subscriber computer 302. The input module can obtain available structures and building blocks data 314, such as from a database of from the subscriber computer 302. The input module 308 then provides the data to the generative module 316, and processed according to the protocols described herein. The generative module 316 uses the AI protocols for analysis of chemical structures and substructures in view of the target protein to generate suitable structures, which can be processed using medicinal chemistry and computational chemistry units. The AI protocols can provide AI-aided de novo drug design. The medicinal chemistry and computational chemistry units can include models, which training and benchmarking, and provide interpretable domain-specific analytics for generative chemistry tools. The generative module 316 provides the one or more generated structures to the results analyzer module 318, which analyzes the results in accordance with the protocols described herein. The results analyzer module 318 can include graphs, analytics, and comparisons of the generated structures, and can save the information (e.g., SDF CSV), or provide the data to a database. The results analyzer module 318 may provide the data to the subscriber computer 302 for analysis. For example, the results analyzer module 318 can analyze the results with the platform, or export the results in a standard format from a web-interface or via an API. The results analyzer module 318 can also provide novel compound candidates 320 that are selected based on the protocols described herein. These novel compound candidates 320 can then be provided to the subscriber computer 302.

The configuration module 308 can be configured to utilize existing experimental results and available compound structures and sub-structures (e.g., building blocks). The configuration module 308 can include target identification data and the desired properties of a generated compound, which can also use structural data, active compounds. The configuration module 308 may also receive input of generation options for the generated compounds. In some aspects, the configuration module 308 can be configured to handle data for different targets, such as when having data of: crystal structure only, crystal and ligand data, ligand data only, no crystal data or no ligand data, or desired properties.

The generative module 316 can be configured to perform generative exploration of chemical spaces for the desired outcome of a compound interacting with a target protein. This can include molecular property optimization, structural optimization, and affinity optimization, which are all based on the protocols described herein. The molecular property optimization can include optimizing the structure to have the desirable molecular properties, such as stability, solubility, permeability, absorbability, pharmacodynamics, pharmacokinetics, and the like. The structural optimization can include optimizing the structure to have feature suitable for medicinal chemistry and to be capable of being synthesized, with simple synthesis being preferred. The affinity optimization can include optimizing the molecule fitting and binding and thereby having affinity with the target protein. In some aspects, the generative module 316 can include a number of models, such as those described herein, which models can be provided with the platform.

In some embodiments, a subscriber can upload their own models via the subscriber computer 302, and thereby the subscriber models can be interfaced with and sued with the generative module 316. The subscriber model can be trained as described herein. The model can then be used for compound generation alone or with the other models of the system.

The results analyzer module 318 can be configured to perform annotation and virtual screening of the generated compounds. This can include screening the compounds through vendor databases for identifying whether the compound or derivative thereof is present or the component parts of the compounds are available for purchase to use to synthesize the compounds. The screening can also be against a clinical trials analysis, such as an insilico clinical trials (e.g., Inclinico), which allows for prediction of clinical trials outcomes, by predicting clinical trial success rates, identifying weak points in trial design, and adopting an enhanced ability to obtain best practices in clinical trials. The molecular properties can also be screened, in order to filter for compounds having desired molecular properties. The rewards-based rankings (e.g., SOMs) can be used to filter through the generated compounds during the analysis. The patentability or novelty of the generated compounds can be assessed with the results analyzer module 318, which can filter for molecules that have not been generated before. The results analyzer module 318 can also filter the generated compounds through a synthetic accessibility analysis to determine the ease or difficulty in synthesizing each specific compound, and filtering for compounds that can be synthesized.

The results analyzer module 318 can also perform ranking and prioritization of the generated compound. The ranking and prioritization can be performed as described herein to rank the compounds to identify the compounds to be synthesized and validated. The selected compounds can then be provided, e.g., in a report, for results visualization (e.g., on a display or printed report) and validation. The selected compounds can be provided to the subscriber computer 302.

In some embodiments, a method of obtaining a generated compound can be performed with the CGS platform 306. The method can include a user identifying a target protein or a target disease and defining output criteria for any generated compound to satisfy. The GCS platform them performs the computations for compound generation and identifies one or more generated compounds, which are generated, analyzed, and ranked as described herein. The compounds having the highest ranking to satisfy the output criteria and then identified and the identification and other information of these compounds are provided to the user (e.g., via subscriber computer). The CGS platform can be configured for operating at pathway activity levels that make it possible to handle high dimensionality data. The CGS platform has an AI-powered toolkit including: depth feature selection engine for pathway reconstruction, pathway scoring engine, target association, deep-learned transcriptional response scoring engine, and activation-based scoring engine. This multimodal approach combining big data, chemistry, biology and medicine allows a complete characterization of the interplay between molecular structures, properties, alteration in biological samples and drug response required for generation of compounds that are biologically active for a target protein (e.g., protein of a biological pathway).

In some embodiments, a computer-implemented method can include: receiving input of a biological target; receiving a generative tensorial reinforcement learning (GENTRL) model or other generative model trained with reference compounds, wherein the reference compounds include: general compounds, compounds that modulate the biological target, and compounds that modulate biomolecules other than the biological target; generating structures of generated compounds with the generative model; prioritizing structures of generated compounds based on at least one criteria; processing prioritized chemical structures of the generated compounds through a Sammon mapping protocol to obtain hit structures; and providing chemical structures of the hit structures. In some aspects, the method can include: receiving the reference compounds; and training the generative model with the reference compounds. In some aspects, comprising at least one: refining, with the generative model, structures with at least one reward function; or performing a pharmacophore modeling with the generative model.

In some embodiments, the at least one criteria to be satisfied for prioritizing is determined to be satisfied by at least one of: performing a molecular filtering operation on the generated compounds; performing a clustering/diversifying operation on the generated compounds; analyzing vendor compounds in view of the generated compounds; performing a reward prioritization; performing a root-mean-square deviation value determination for fit of generated compounds to the biological target; or analyzing novelty of the generated compounds based on published intellectual property documents.

In some embodiments, the method can include performing a structure refining protocol with at least one Kohonen self-organizing map (SOM). In some aspects, the Kohonen SOM includes: a trending SOM that rewards structures that are newer based on a chronological timeline compared to older structures; a general biological target SOM that rewards a class of structures for a family of biological targets that include the biological target over other classes of structures without biological activity to the family of biological targets; and a specific biological target SOM that rewards a structure that specifically targets the biological target.

In some embodiments, the method can include performing a pharmacophore modeling with a generated compound and biological target to analyze a scaffold structure or pendant substituent structures of the generated compound. This can include structure analysis as well as docking analysis with the biological target.

In some embodiments, the method can include: generating a latent space manifold having a plurality of the reference compounds in the trained generative model; and generating new compounds with the trained generative model that are not present in the latent space manifold.

In some embodiments, the method can include prioritizing the structures of generated compounds based on at least one criteria includes at least one of the following: filtering compounds to meet a predefined range molecular descriptors; applying a medicinal chemistry filter to remove compounds having undesirable medicinal chemistry properties; applying a Tanimoto-based clustering and diversity to remove compounds having similar structures; applying a trending SOM that selects structures that are newer based on a chronological timeline compared to older structures; applying a general biological target SOM that selects structures that are biologically active for a family of biological targets that include the biological; applying a specific biological target SOM that selects structures that specifically target the biological target; or applying a pharmacophore filter to remove compounds that fail pharmacophore modeling.

In some embodiments, the method can include screening the generated compounds for patentability.

In some embodiments, the method can include obtaining at least one data set having the reference compounds including: patient data for a set of known compounds having a specific functional activity, the known compounds being arranged by date of identification of the known compound; and/or chemical structure data for a set of known compounds having the specific functional activity.

In some embodiments, the methods can include identifying an activity threshold for a specific functional activity in modulating the biological target, wherein generated compounds with less than the activity threshold are defined as inactive and compounds having the activity threshold or higher activity are defined as active compounds.

In some embodiments, the methods can include: processing data sets of the reference compounds to exclude outlier compounds; and normalize an input chemical space by reducing the number of compounds containing similar structures per each cluster of compounds.

In some embodiments, the methods can include: identify a plurality of first compounds, the plurality of first compounds being part of a learned manifold of the first compounds; parameterizing a structure of the learned manifold with a tensor train using partially known properties of the compounds, the partially known properties include known properties of the compounds; and generating a plurality of second compounds, the second compounds being based on the first plurality of compounds, wherein the second compounds are the generated compounds.

In some embodiments, the methods can include: identifying a predetermined range of molecular descriptors; obtaining an output of generated compounds from the generative model; and excluding compounds outside of the predetermined range to obtain a chemical space with the generated compounds within the predetermined range.

In some embodiments, the methods can include randomly selecting a number of generated compound from the Sammon Mapping that cover a chemical space to obtain the hit structures.

In some embodiments, a method of synthesizing generated compounds can include: obtaining a report with the provided chemical structures of the hit structures; selecting at least one compound from the provided chemical structures that has a specific functional activity with the biological target; and synthesizing the at least one compound.

In some embodiments, a method of validating biological activity of generated compounds can include: obtaining the synthesized at least one compound generated by the generative model; and validating the synthesized at least one compound in a biological assay to have the specific functional activity.

In some embodiments, a method of generating a compound having a specific functional activity can include: selecting the specific functional activity; obtain reference compounds; training a model for the specific functional activity with the reference compounds; generating structures of compounds; processing the generated structures with defined reward functions; prioritizing a set of the generated structures; selecting at least one compound from the generated structures that have the specific functional activity in silico; synthesizing the at least one compound; and validating the synthesized at least one compound to have the specific functional activity.

In some embodiments, the methods can include: avoiding mode collapse; utilizing partially labeled data; and extrapolating a chemical space of compounds from the manifold of the first compounds, wherein the extrapolated chemical space of compounds include second compounds that are not part of the manifold of the first compounds and/or a training library of compounds. In some aspects, the mode collapse is avoided by compressing the chemical space of compounds into a latent distribution. In some aspects, the latent distribution is a Gaussian distribution.

In some embodiments, the methods can include: parameterizing the latent space in a high-dimensional lattice with a plurality of multi-dimensional Gaussian distributions at each node using a prior distribution of compounds, wherein the parameterizing relates latent codes to compound properties, and wherein the parameterizing operates with omitted parameter values without explicitly imputing the omitted parameter values.

In some embodiments, the methods can include estimating chemical structure relation to defined functional compound having a defined bioactivity using self-organizing maps (SOMs). In some aspects, the SOMs includes a trending SOM that is a Kohonen-based reward function that discriminates unknown compounds from defined functional compounds. In some aspects, neurons having a plurality of unknown compounds are used to positively reward a compound generating model in order to obtain unknown compounds. In some aspects, the SOMs includes a general functional SOM that is a Kohonen map that distinguishes compounds having the general function from compounds that do not have the general function in order to obtain compounds having the general function. In some aspects, the general function is kinase inhibition and the compounds are kinase inhibitors. In some aspects, unknown compounds predicted to have the general function with a cell coefficient over 1.3 are processed through a Kohonen-based classifier protocol. In some aspects, the SOMs include a specific functional SOM, which has been trained to identify compounds having the specific functional activity. In an example, the specific functional activity is DDR1 kinase inhibition. In some aspects, known compounds having the known specific functional activity are distributed over a plurality of related neurons. In some aspects, the method can include prioritizing generated compound structures by using the trending SOM, general functional SOM, and specific functional SOM. In some aspects, the methods can include identifying nodes having compounds with the specific functional activity, and preferentially using the identified nodes.

In some aspects, the methods can include obtaining at least one data set having: (A) small molecule compounds with the specific functional activity; (B) a positive set of compounds having the specific functional activity; (C) a negative set of compounds having a different functional activity, optionally not having the specific functional activity; (D) patient data for a set of known compounds having the specific functional activity, the known compounds being arranged by date of identification of the known compound (e.g., patent filing date); or (E) chemical structure data for a set of known compounds having the specific functional activity. In some aspects, the method can include identifying an activity threshold for the specific functional activity, compounds with less than the activity threshold are defined as inactive and compounds having the activity threshold or higher activity are defined as active compounds. In some aspects, the methods can include processing the data sets of (A)-(D) to exclude outlier compounds; and normalizing an input chemical space by reducing the number of compounds containing similar structures per each cluster of compounds.

In some embodiments, the methods can include: identify a plurality of first compounds, the plurality of first compounds being part of a learned manifold of the first compounds; parameterizing a structure of the learned manifold with a tensor train using partially known properties of the compounds, the partially known properties include known properties of the compounds; and generating a plurality of second compounds, the second compounds being based on the first plurality of compounds.

In some embodiments, the methods can include: training a generative model for the specific functional activity with a set of compounds having the general functional activity (e.g., kinase inhibitors) and a set of compounds having the specific functional activity (e.g., DDR1 inhibitors). In some aspects, the methods can include: pre-training the generative model for the specific functional activity with a dataset of general molecules (e.g., ZINC database).

In some embodiments, the methods can include: identifying a predetermined range of molecular descriptors; obtaining an output of generated molecules from the model; and excluding compounds outside of the predetermined range to obtain a chemical space with compounds within the predetermined range. In some aspects, the methods can include reducing the chemical space by clustering and sorting procedures. In some aspects, the method includes prioritizing structures with the general activity SOM and the specific functional activity SOM. In some aspects, the methods include obtaining a 3D-pharmacophore hypothesis from crystallographic data for compounds complexed with a protein (e.g., DDR1 kinase) of the specific functional activity (e.g., inhibiting DDR1 kinase).

In some embodiments, the methods include prioritizing compounds by at least one of: Sammon mapping; and root-mean-square deviation value from the 3D-pharmacophore hypothesis. In some aspects, the Sammon mapping is used for randomly selecting a number of chemical structures covering the chemical space thereof.

EXAMPLE

An example protocol is now described. The datasets of the known inhibitors of the biological target and related targets (e.g., kinase inhibitors and DDR1 inhibitors) were used to fine-tune the generative GENTRL model that was pre-trained on a large dataset of molecules available in ZINC database. The initial output of GENTRL was 30,000 small molecule structures as a "crude mixture". Compounds which did not meet the predefined ranges of molecular descriptors were excluded. To remove molecules bearing structural alerts or reactive groups, the protocol applied medicinal chemistry filters (MCFs) containing over 100 substructure queries. The resulted chemical space was then reduced by clustering and diversity sorting procedures.

Then, the protocol used the constructed general biological target family SOM (e.g., general kinase SOM) and specific biological target SOM (e.g., specific kinase SOMs) to perform an additional prioritization of structures towards the potential biological target inhibition (e.g., kinase inhibition) activity and activity against the specific biological target (e.g., DDR1 kinase), respectively. Although the generative model was focused on the production of structures classified a priori as specific biological target inhibitors (e.g., DDR1 inhibitors) by the Kohonen-based reward function described above, the protocol also used pharmacophore modeling to evaluate the generated structures. Crystallographic data available for small-molecule compounds in complex with the biological target (e.g., DDR1 kinase) was used to construct 3D-pharmacophore hypotheses. These models were applied to score the obtained structures by root-mean-square deviation value (RMSD, Å) which reflects the degree of fit to the developed pharmacophore (see examples in FIGS. 2A-2C).

FIG. 2A shows a 3-Centered pharmacophore hypothesis: Acc—hydrogen bond acceptor (r=2 Å), HydjAro—hydrophobic or aromatic center (r=2 Å), Hyd—hydrophobic center (r=2 Å). FIG. 2B shows a 4-centered pharmacophore hypothesis: Acc—hydrogen bond acceptor (r=2 Å), HydjAro—hydrophobic or aromatic center (r=2 Å), Hyd—hydrophobic center (r=2 Å), Acc|Specific—hydrogen bond acceptor or a fragment with similar spatial geometry (e.g. double or triple bond, planar cycle) (r=1.7 Å). Non-depicted distances are the same as for 3-centered pharmacophore. FIG. 2C shows a 5-centered pharmacophore hypothesis containing the same points that are highlighted in FIG. 2B with an additional hydrophobic feature. Non-depicted distances are the same as for 3-centered and 4-centered pharmacophores. This is based on the reported small-molecule DDR1 inhibitor (PDB code: 5BVN).

Figure 3:
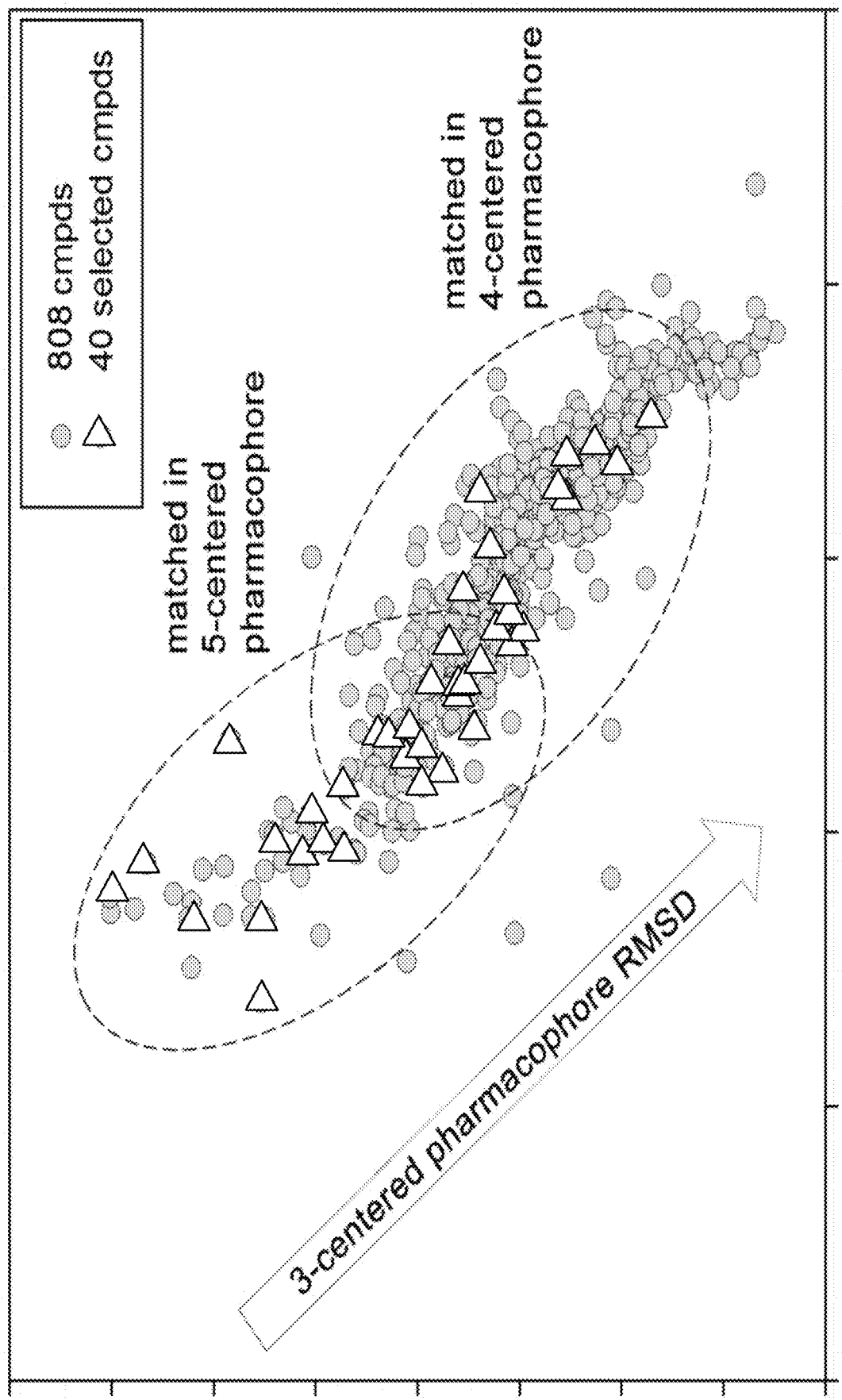
FIG. 3 includes a non-linear Sammon map with the selected 40 molecules are marked by triangles.

At the final step of the prioritization, the protocol used a Sammon mapping approach with the same set of descriptors as well as RMSD values outputted from the pharmacophore modeling. When the map was constructed, the protocol selected a number (e.g., 40) structures in random fashion, which smoothly covered the resulting chemical space. Special attention was placed on the distribution of RMSD values (see FIG. 3). FIG. 3 shows a non-linear Sammon map with the selected 40 molecules are marked by triangles. Areas of the best pharmacophore matching are highlighted by circles.

All the performed prioritization procedures are summarized below. The physical chemistry filter is for compounds meeting a predefined range of molecular descriptors (e.g., 12147 compounds selected). The MCF filter is for compounds containing alert-substructures that are usually undesirable in medicinal chemistry (e.g., 7912 compounds selected). The clustering and diversity filter is a Tanimoto-based clustering followed by diversity maximization per each cluster, removing (5 compounds in cluster) of similar compounds and chemical space normalization (e.g., 5542 compounds selected). The similarity filtering is a Tanimoto-based similarity towards compounds available within vendors' (MolPort, ZINC) stocks (threshold 0.5) (e.g., 4642 compounds selected). The general biological target family SOM (e.g., general kinase SOM) filters structures classified as inhibitors versus non-inhibitors for the biological target family (e.g., 2570 compounds selected). The specific biological target SOM (e.g., DDR1 kinase) filters structures selected from neurons containing at least one specific target inhibitor to overcome bias (e.g. 1951 compounds selected). The pharmacophore searching filter is for structures that successfully passed the pharmacophore modeling (e.g., 848 compounds selected). The Sammon mapping filter is for compounds subjected to Sammon learning procedures to randomly select the final set of structures (e.g., 40 compounds selected).

In some embodiments, the protocol can include a chemistry professional to analyze the structures for the ease of synthesis. Synthesis of the selected compounds, as well as cell-based assays can be performed.

In the present example, six molecules were generated, selected, and synthesized and were submitted for biological testing (e.g., within 35 days). Among the tested samples four compounds have demonstrated moderate to high activity (see dose-response curves in FIG. 4A). Compound 1 (i.e., INS015_036) and Compound 2 (i.e., INS015_37) showed strong inhibition of DDR1 activity with an $IC_{50}$ value of 10 and 21 nM, respectively. Compound 3 (i.e., INS015_030) and Compound 4 (i.e., INS015_032) demonstrated moderate potency (1 µM and 278 nM, respectively), while Compound 5 (i.e., INS015_039) and Compound 6 (i.e., INS015_038) were inactive. Since the dose-response curves for Compounds 2 and 4 seemed likely inconsistent, additional experiments were performed to confirm the activity of these molecules towards DDR1 kinase (see FIG. 4B). In these studies, Compound 2 has demonstrated an $IC_{50}$ value of 37 nM, while Compound 4 was 4-times less active ($IC_{50}$=156 nM). Thus, nanomolar activity of both compounds was proved in two different biochemical assays. Compounds 1 and 2 were also evaluated towards DDR2 kinase. According to the results depicted in FIG. 4A, the activity of compound 1 was 23-times weaker than for DDR1, while compound 2 showed an $IC_{50}$ value of 76 nM. Based on these results, it was concluded that two the most active DDR1 inhibitors (Compounds 1 and 2) are interesting structures for further investigation and optimization.

Figure 4A:
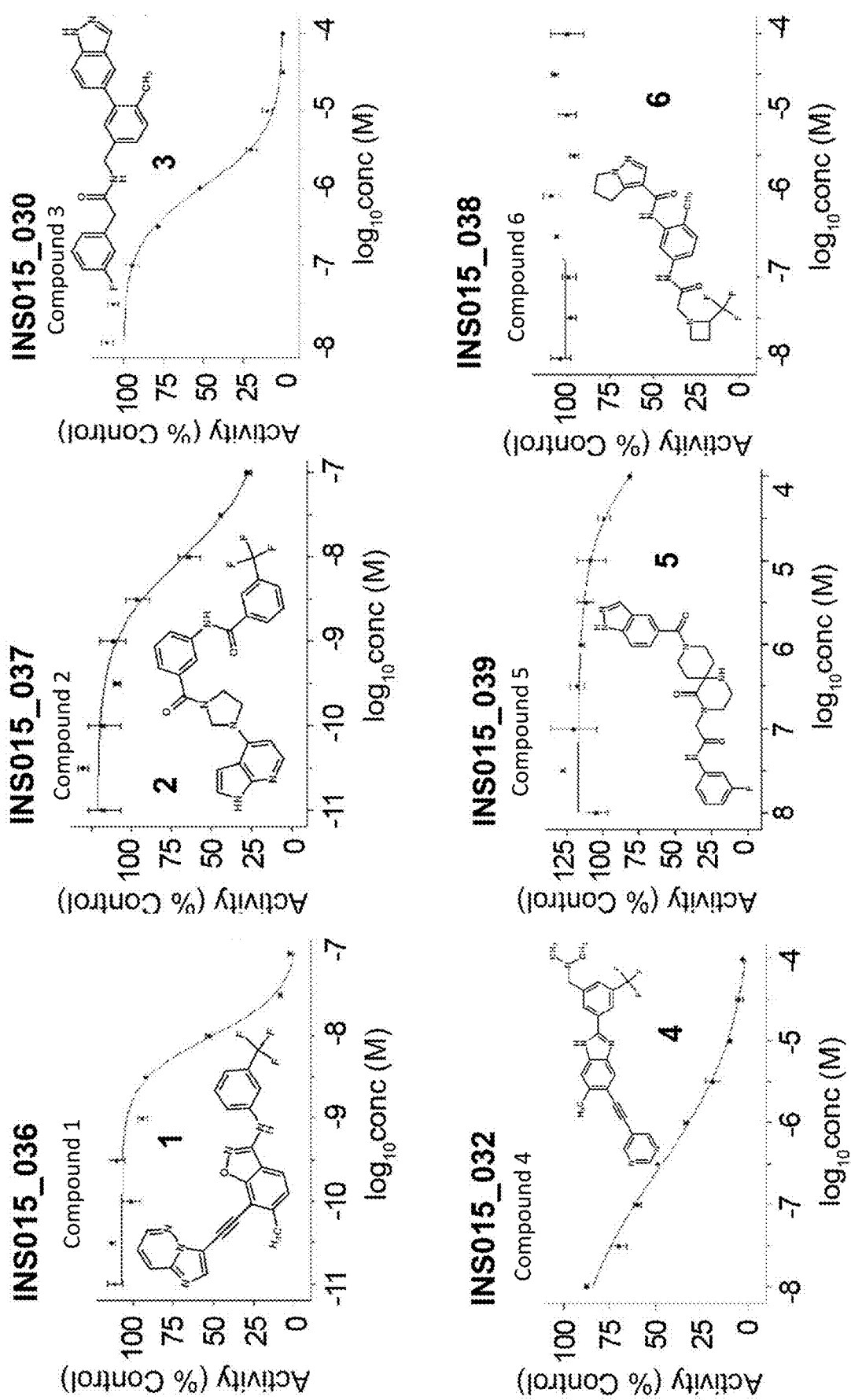
FIG. 4A includes dose-response curves for Compounds 1-6.
Figure 4B:
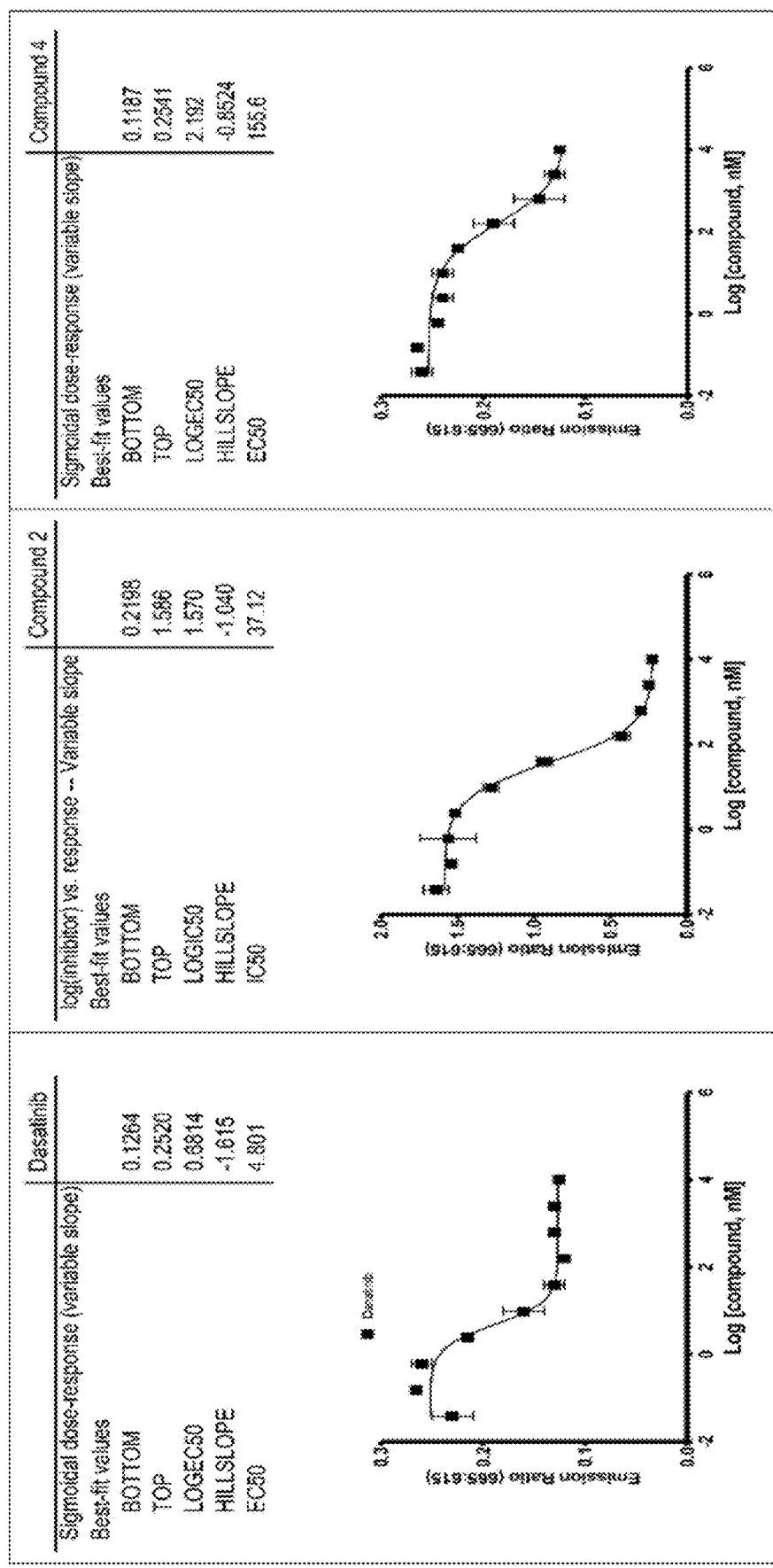
FIG. 4B includes graphs showing the IC50 of Compounds 2 and 4.
Figure 4C:
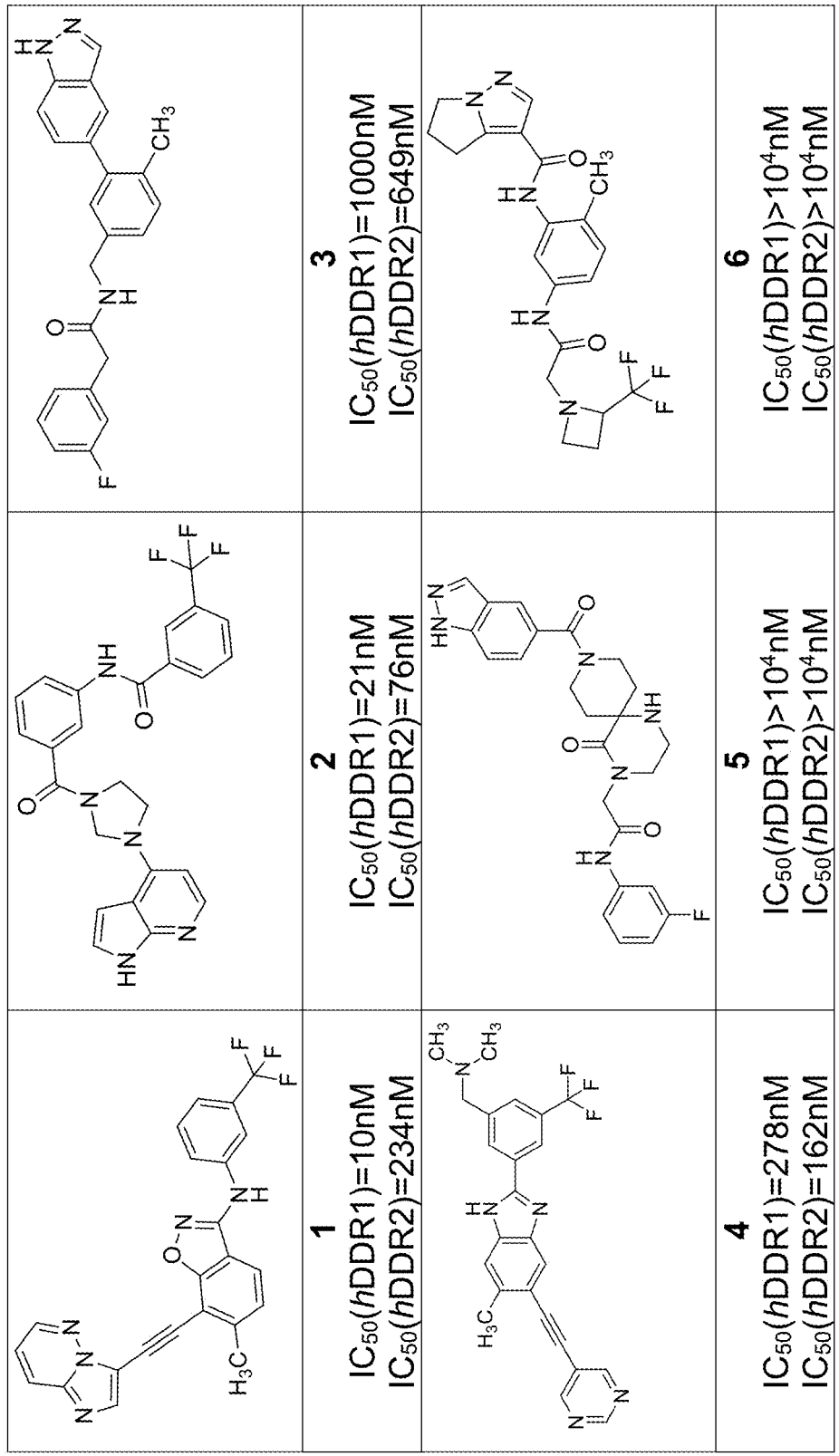
FIG. 4C shows the structures of Compounds 1-6 and their IC50 value for DDr1 and DDR2.

FIGS. 4A-4B show the structures and dose-response curves for the generated molecules. The six generated compounds were tested in a dose-dependent manner against DDR1 tyrosine kinase. Compounds 1 and 2 demonstrated the IC50 values in the low nanomolar range (FIG. 4A). Compounds 2 and 4 were additionally rescreened towards DDR1 kinase using another biochemical assay (Thermo Fisher-PR6913A) and have demonstrated the IC50 values of 37.12 and 155.6 nM respectively (FIG. 4B). FIG. 4C shows the structure and the IC50 against DDR1 and DDR2 for Compounds 1-6, as identified by their compound number.

To partially elucidate the results obtained from the biological study, quantum mechanical (QM) calculations were performed. FIGS. 5A-5C show the rigid alignment of a conformation best fitted pharmacophore hypothesis and a conformation predicted by QM-calculations. The predicted 3D conformation of Compound 1, passing the pharmacophore hypothesis, was very similar to that verified in vacuo as more preferred and stable, using ab initio QM calculations (FIG. 5A). For Compound 1 there may be a "lock and key" entropy-driven binding mechanism. For Compound 3 it was observed a moderate RMSD value (FIG. 5B). Benzimidazole Compound 4 was much less active than its close structural analogue Compound 1 (not shown); however, QM calculations have shown that its conformation with an amino group in the para-position to methyl group is more stable and does not match hydrogen bond acceptor (HBA) feature in the hypothesis. Moreover, at a physiologically relevant pH value of 7.4, the second basic nitrogen in this core in Compound 4 is almost fully protonated.

Among a pool of 3D conformations of Compound 5 verified by QM, it was observed that none passed the pharmacophore hypothesis (FIG. 5C). Compound 6 did not demonstrate any activity, presumably due to bulky hydrophobic moiety with the chiral point. The positioning of the trifluoromethyl fragment may not be appropriate within the binding site. Moreover, it is speculated that the vicinal amide group is not located in a beneficial binding position.

To overcome some issues of compounds that are not favorable or do not satisfy certain criteria, the protocol can include obtaining a list of expert opinions on the selected structures provided by a professional medicinal chemistry team.

For Compound 1, human experts noticed the similarity with ponatinib (IC50=9 nM, DDR1 inhibition). The Compound 1 is bearing a bioisostere of amide bond. The Compound 1 is very impressive from the A standpoint. Compound 2 is bearing a unique central linker (imidazolidine), the chemistry is very different from Compound 1. The human expert indicated that stability should be checked for Compound 2. For Compound 3, some issues were addressed to potential metabolic stability of the compound (acetylene, pyrimidine and dimethylamino groups). The tertiary amine of Compound 3 is also under question in terms of activity and SAR observed for DDR1 inhibitors. For Compound 4, human experts have found the presented chemotype rather neutral or attractive, and patentability has been mentioned as a challenging issue; however, recent patent search has revealed clear IP status. For Compound 5, the human expert indicted an interesting chemotype in kinase chemistry, with good physicochemical properties, in particularly solubility. According to expert opinion the Compound 6 has novel structure and contains interesting and unique moieties, e.g. unique hinge binding core. According to the human expert comments, almost all the compounds inspected have been recognized as novel and attractive for further biological trials. Several novel compounds have been classified as bearing unique structure. On the other hand, expert-identified features, that require more work in terms of further drug development, including metabolic instability, a relatively poor synthetic accessibility and potential need for solubility tuning, have been properly attributed to some moieties. These are features that could be added to more sophisticated screening protocols or be integrated in a second round of refinement. Accordingly, the protocol for generating the compounds can include a step for a human expert in chemistry to analyze the structures of the compounds to facilitate selection of a lead compound or for selection of a compound to be synthesized and validated for biological activity.

In some embodiments, the compounds can be analyzed for patentability with the platform. It is noteworthy that almost all the selected compounds have been recognized as having good IP position as shown in Table 1. The protocol can preliminary score these compounds using available specific databases on chemical patents. Formally, 39 structures have been classified as novel because they fall outside the scope of any published patents or applications. One of the generated structures was claimed in a patent application describing multimodal kinase inhibitors, but the kinases listed therein do not include DDR1.

TABLE 1

| IP Summary | | | | | |
|---|---|---|---|---|---|
| ID | Results of Similarity Searching, %* | Markush** | Example*** | MolPort**** | Zinc**** |
| INS015_001 | <70 | 0 | 0 | 0.27 | 0.27 |
| INS015_002 | 70-74 (4) | 0 | 0 | 0.24 | 0.24 |
| INS015_003 | <70 | 0 | 0 | 0.21 | 0.29 |

TABLE 1-continued

IP Summary

| ID | Results of Similarity Searching, %* | Markush** | Example*** | MolPort**** | Zinc**** |
|---|---|---|---|---|---|
| INS015_004 | 85-89 (2); 80-84 (10); 75-79 (29); 70-74 (57) | 0 | 0 | 0.39 | 0.39 |
| INS015_005 | 75-79 (9); 70-74 (20) | 0 | 0 | 0.27 | 0.27 |
| INS015_006 | 80-84 (9); 75-79 (22); 70-74 (62) | 0 | 0 | 0.39 | 0.39 |
| INS015_007 | 95-98 (1); 90-94 (10); 85-89 (8); 80-84 (17); 75-79 (61); 70-74 (336) | 0 | 0 | 0.36 | 0.36 |
| INS015_008 | <70 | 0 | 0 | 0.21 | 0.19 |
| INS015_009 | 75-70 (16) | 0 | 0 | 0.38 | 0.38 |
| INS015_010 | 71-70 (4) | 0 | 0 | 0.38 | 0.38 |
| INS015_011 | <70 | 0 | 0 | 0.22 | 0.22 |
| INS015_012 | 75-79 (2); 70-74 (11) | 0 | 0 | 0.33 | 0.33 |
| INS015_013 | <70 | 0 | 0 | 0.21 | 0.21 |
| INS015_014 | 80-84 (1); 75-79 (16); 70-74 (149) | 0 | 0 | 0.25 | 0.28 |
| INS015_015 | <70 | 0 | 0 | 0.38 | 0.4 |
| INS015_016 | <70 | 0 | 0 | 0.22 | 0.27 |
| INS015_017 | <70 | 0 | 0 | 0.25 | 0.24 |
| INS015_018 | 75-79 (5); 70-74 (85) | 0 | 0 | 0.31 | 0.31 |
| INS015_019 | <70 | 0 | 0 | 0.23 | 0.25 |
| INS015_020 | 70-71 (6) | 0 | 0 | 0.22 | 0.22 |
| INS015_021 | <70 | 0 | 0 | 0.28 | 0.28 |
| INS015_022 | <70 | 0 | 0 | 0.33 | 0.34 |
| INS015_023 | 80-84 (1); 75-79 (10); 70-74 (46) | 0 | 0 | 0.36 | 0.37 |
| INS015_024 | 70-74 (6) | 0 | 0 | 0.36 | 0.39 |
| INS015_025 | 70-74 (9) | 0 | 0 | 0.41 | 0.41 |
| INS015_026 | 70-74 (3) | 0 | 0 | 0.31 | 0.31 |
| INS015_027 | 75-79 (1); 70-74 (25) | 0 | 0 | 0.33 | 0.33 |
| INS015_028 | 70-74 (27) | 0 | 0 | 0.48 | 0.46 |
| INS015_029 | <70 | 0 | 0 | 0.31 | 0.31 |
| INS015_030 | 75-79 (21); 70-74 (222) | 0 | 0 | 0.41 | 0.43 |
| INS015_031 | 70-74 (2) | 0 | 0 | 0.25 | 0.25 |
| INS015_032 | 75-79 (1); 70-74 (45) | 0 | 0 | 0.23 | 0.23 |
| INS015_033 | 70-74 (10) | 0 | 0 | 0.2 | 0.21 |
| INS015_034 | <70 | 0 | 0 | 0.19 | 0.19 |
| INS015_035 | 70-74 (1) | 1 | 0 | 0.36 | 0.36 |
| INS015_036 | 70-74 (1) | 0 | 0 | 0.29 | 0.23 |
| INS015_037 | 75-79 (37); 70-74 (426) | 0 | 0 | 0.48 | 0.48 |
| INS015_038 | 80-84 (1); 75-79 (3); 70-74 (37) | 0 | 0 | 0.43 | 0.43 |
| INS015_039 | 75-79 (6); 70-74 (106) | 0 | 0 | 0.33 | 0.33 |
| INS015_040 | 70-74 (10) | 0 | 0 | 0.38 | 0.38 |

*Similarity searching in SciFinder database was carried out. The ranges of structural similarity are presented. The number of similar compounds in the certain range is enclosed in parenthesis. In the absence of molecules with similarity >70% it was displayed as <70%.
**The number of patent Markush structures a compound match.
***The presence of a compound among the examples in patents
****The maximal similarity between generated compound and molecules from MolPort and ZINC databases Thus, the generated compounds can be screened for patentability by the protocol. This can facilitate compound generation so that compounds that are not patentable are not synthesized and validated. This allows for significant focus of generating compounds that can be commercially viable.

Figure 6:
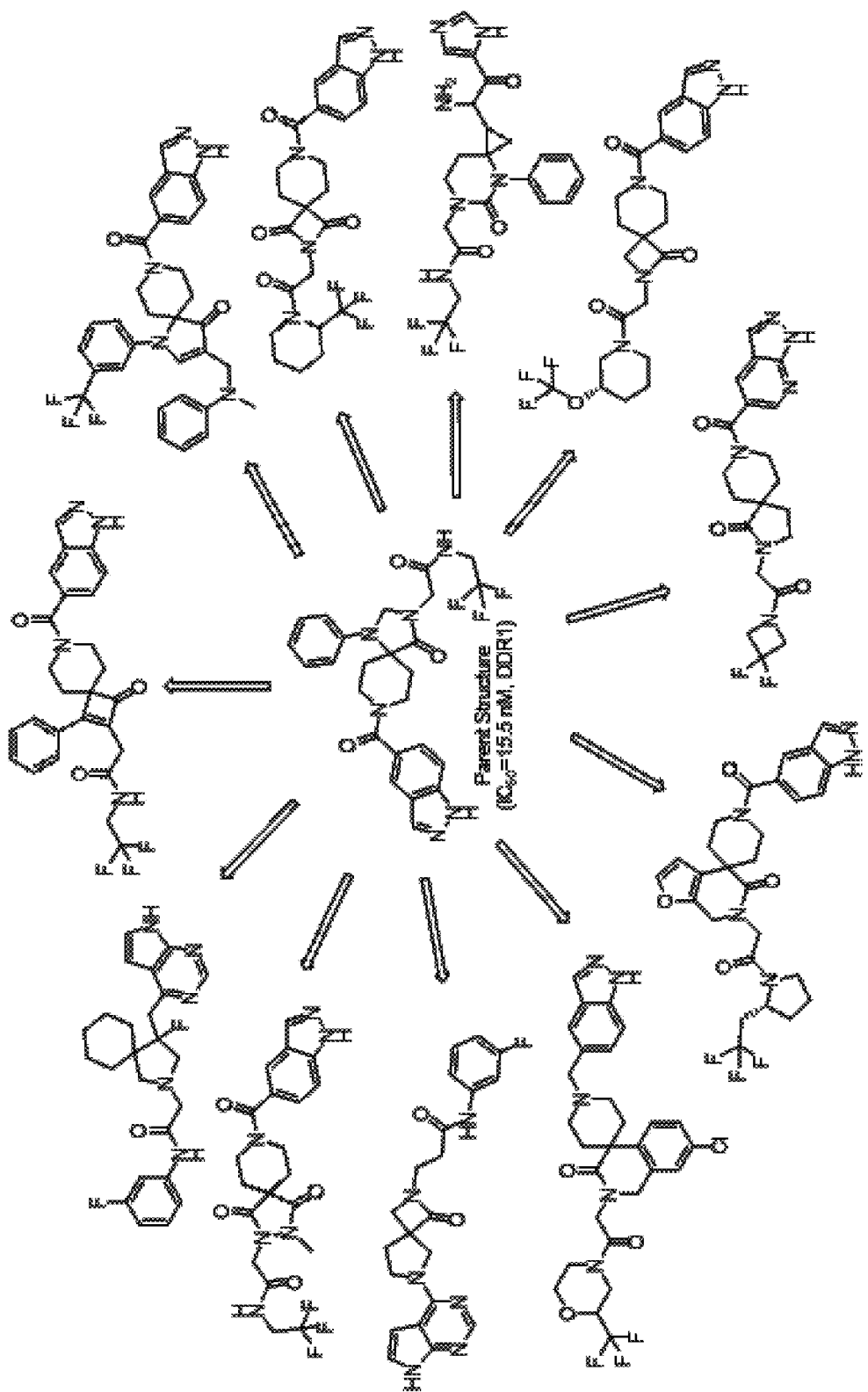
FIG. 6 shows representative examples of the generated structures, compared to the parent DDR1 inhibitor.

In some embodiments, the protocol described herein can result in generating examples of structures that are non-trivial potentially bioisosteric replacements and topological modifications of compounds (FIG. 6). FIG. 6 shows representative examples of the generated structures, compared to the parent DDR1 inhibitor. In general, this in silico morphing does a good job of preserving both the intrinsic physicochemical properties of known DDR1 inhibitors, as well as retaining crucial binding points responsible for DDR1 affinity.

Figure 7:
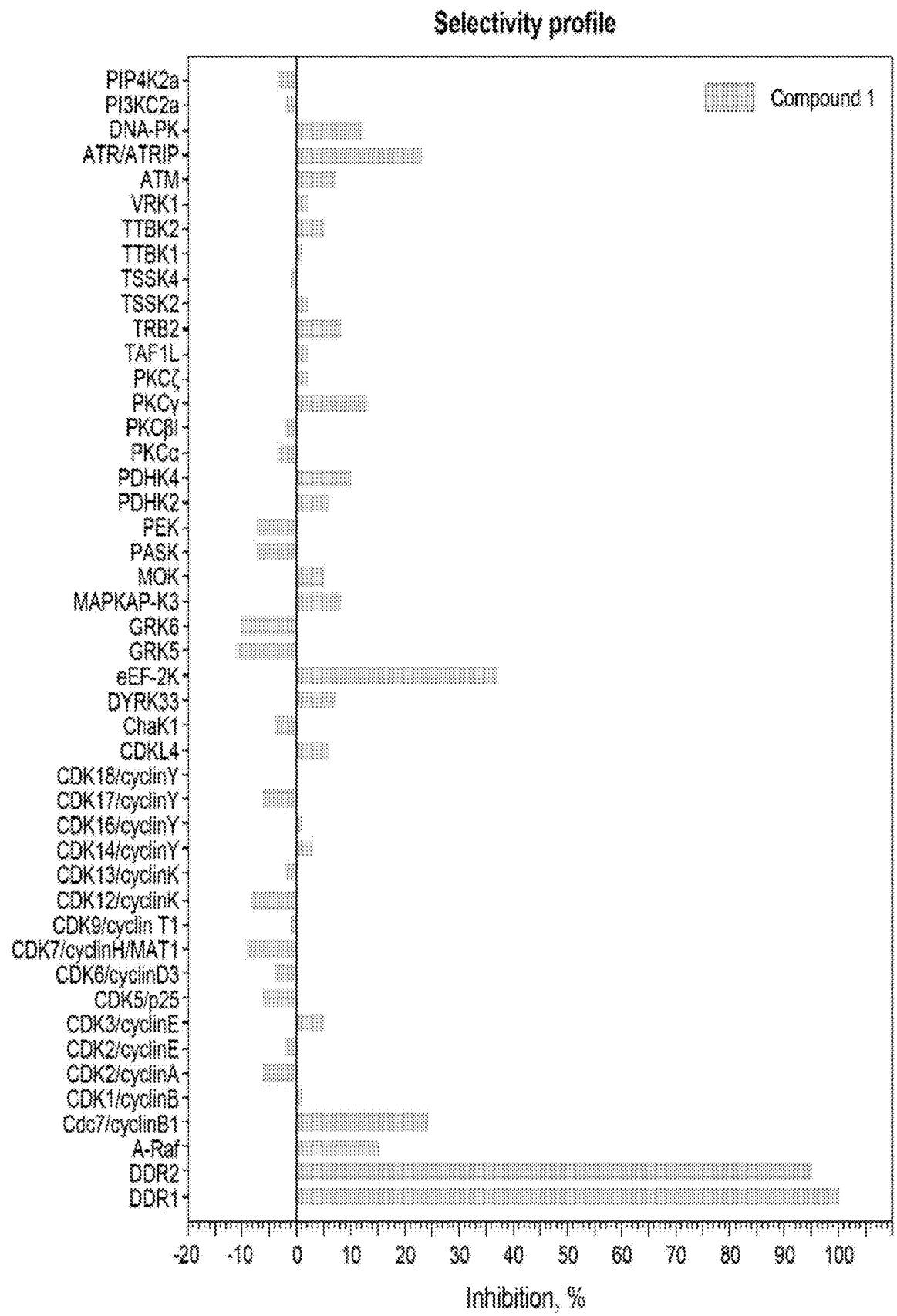
FIG. 7 includes a selectivity profile for Compound 1.
Figure 8A:
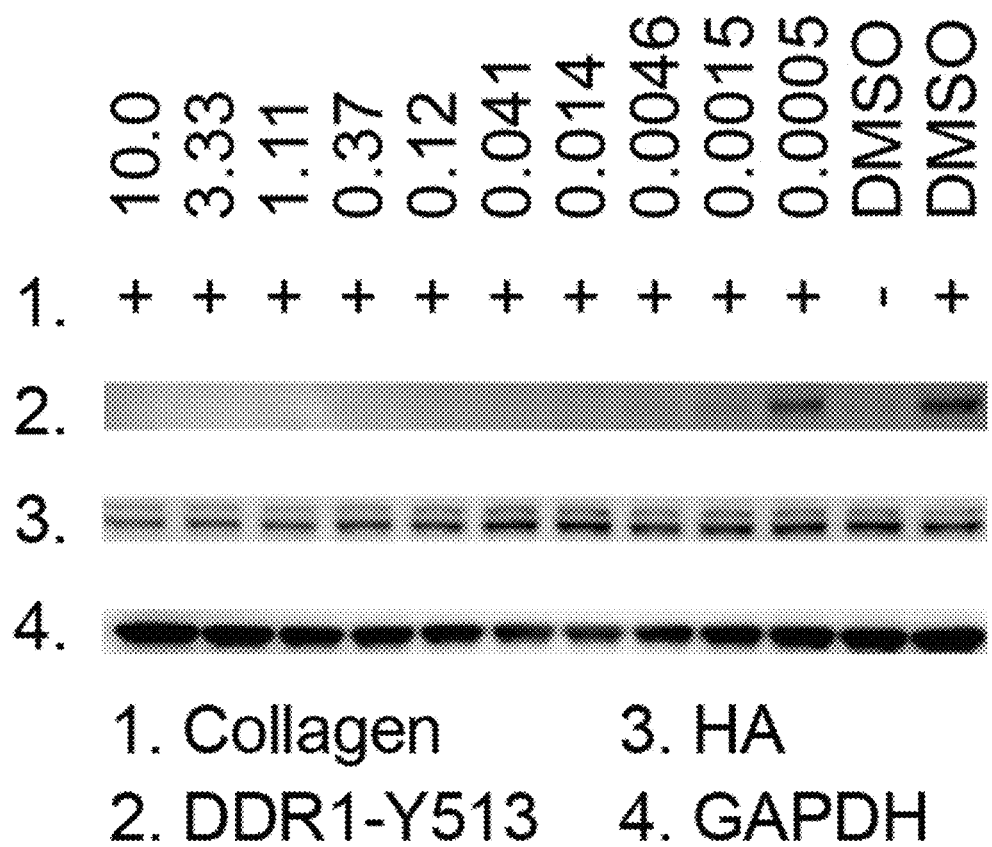
FIGS. 8A-8I include data that shows the Compound 1 and Compound 2 significantly block DDR1 autophosphorylation in a dose-dependent manner.
Figure 8B:
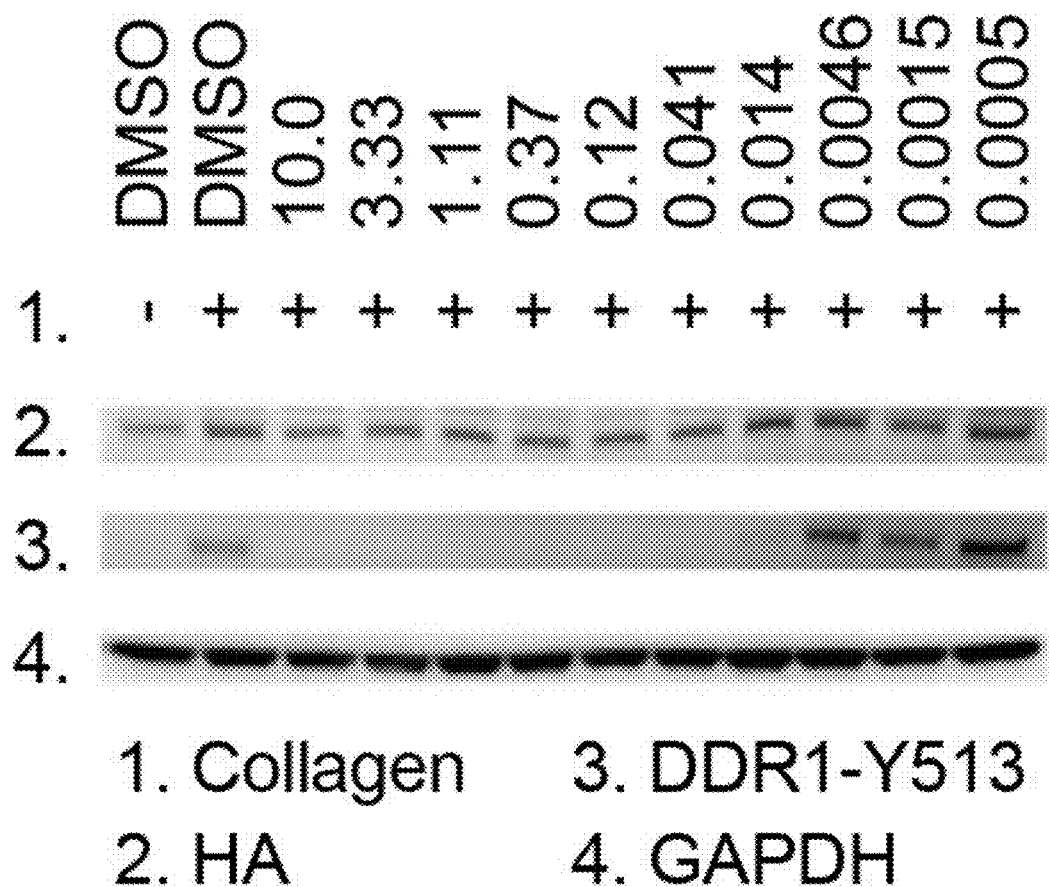
Figure 8C:
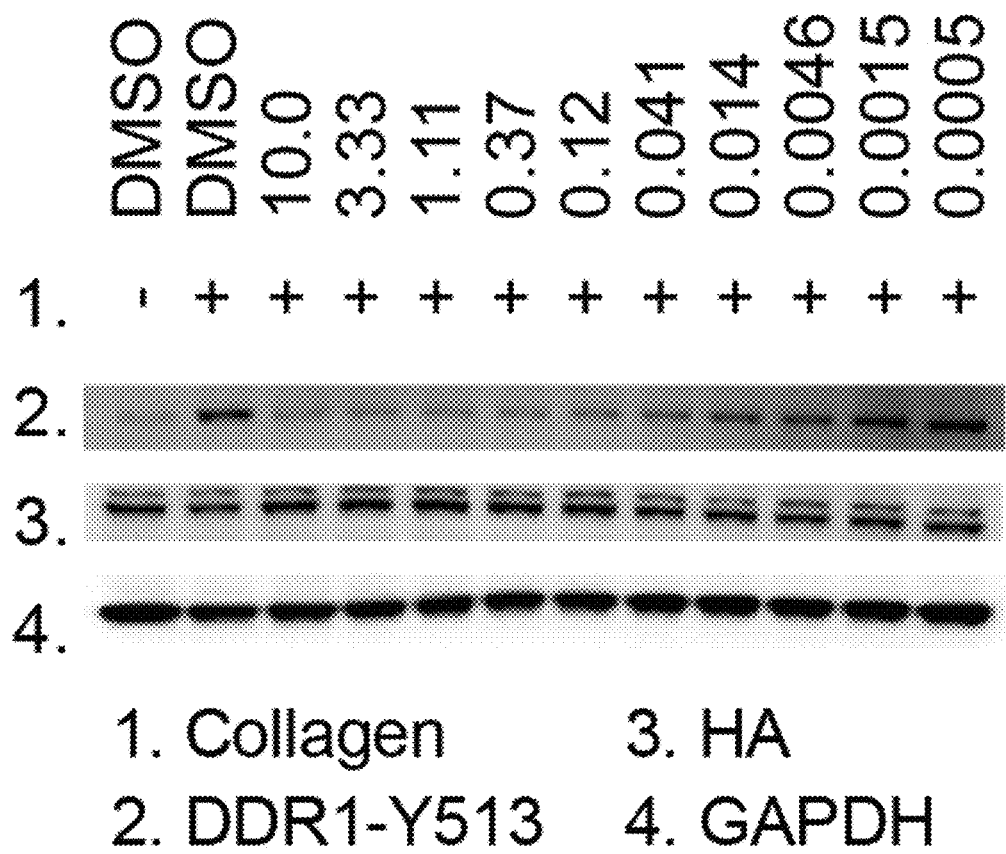
Figure 8D:
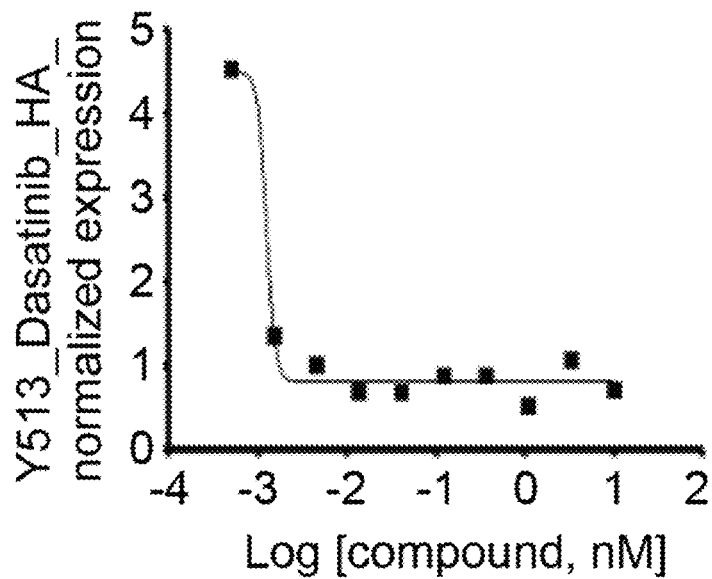
Figure 8E:
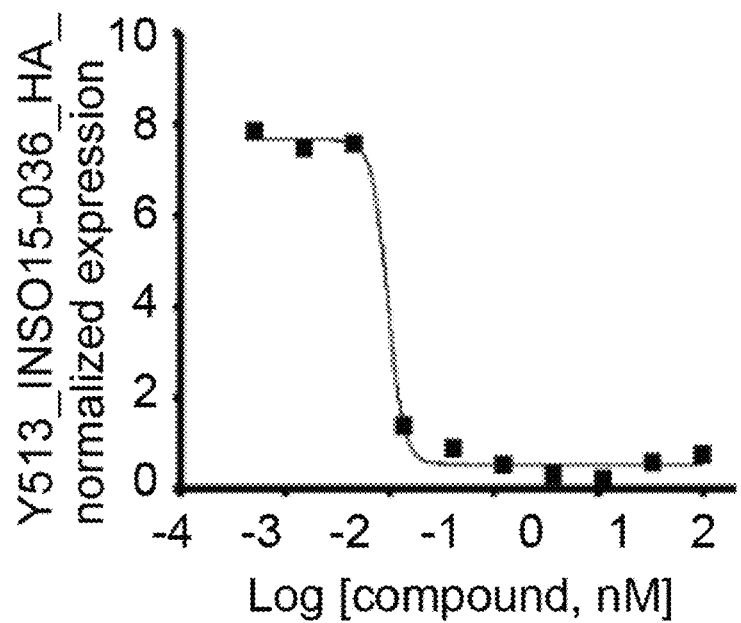
Figure 8F:
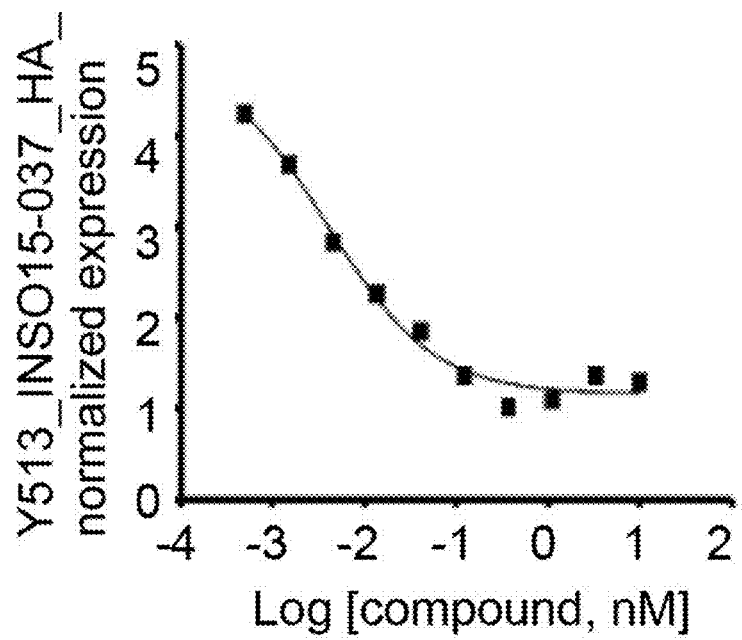
Figure 8G:
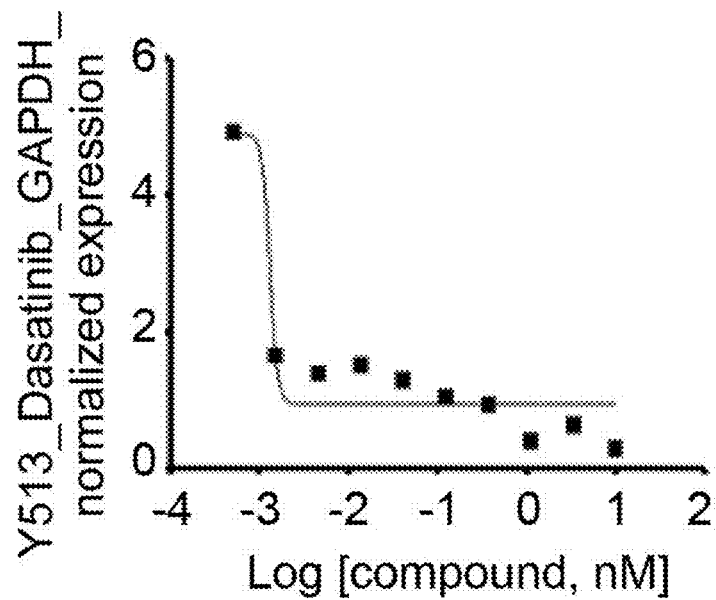
Figure 8H:
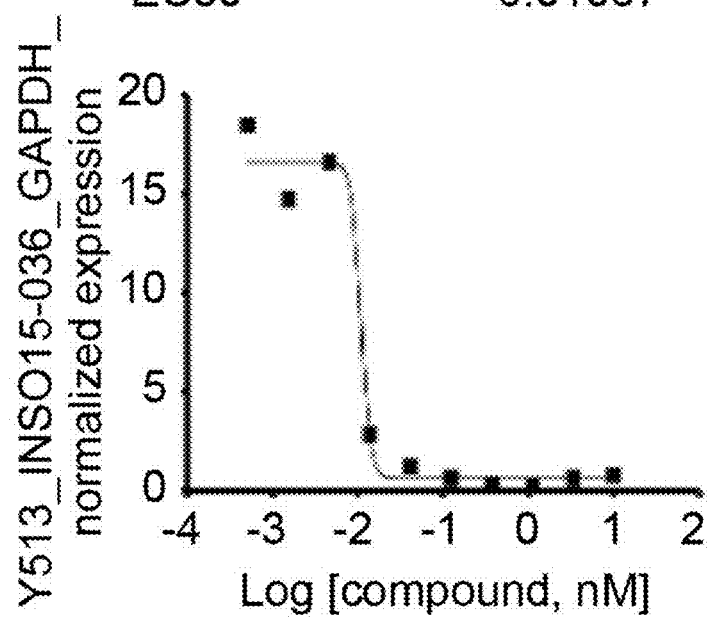
Figure 8I:
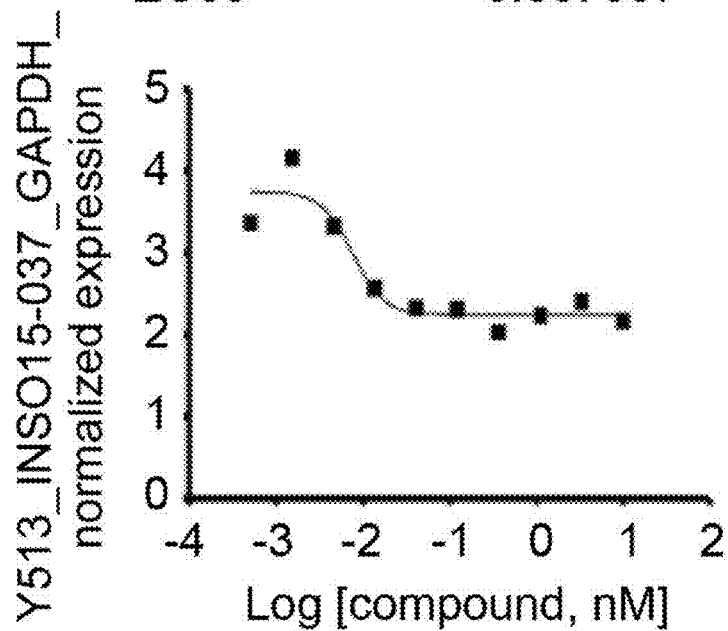

In some embodiments, the workflow protocol can result in generating compounds that are highly selective. The issue of selectivity is of vital importance for a lead compound to estimate possible off-target effects that can influence the pre-clinical evaluation success. The protocol can be configured to assess a selectivity index (SI) for the most active generated compound, such as in enzymatic assay using the scanMAX Delta Kinase Panel by Eurofins. Compound 1 was tested at 10 μM concentration and showed a relatively high SI over 44 kinases, including serine/threonine protein kinases (e.g. CDKs, PKCβ2, MAPKAPK3, TSSKs, TTBK1, A-Raf, etc.), lipid and atypical kinases, as well as dual-specificity protein kinases, as shown in FIG. 7. The highest inhibition potency within the panel was revealed against eEF-2K (INH %=37), while the activity of DDR1 kinase was completely inhibited at this concentration. DDR1 kinase is mostly expressed in epithelial cells, whereas the expression of DDR2 is generally observed in interstitial cells of Leydig. Even though that the prevention of fibrosis is the primary goal, the selectivity over DDR2 kinase is also a very important consideration. The inhibition activity of molecules Compound 1 and Compound 2 towards DDR2 kinase isoform was evaluated as well. Compounds 1 and 2 were found to have good and moderate SI: 23.4 and 3.6, respectively. Subsequent optimization of Compound 1 via a follow up synthesis of close structural analogues may results in an increase in selectivity. The detailed selectivity profile is presented in FIG. 7.

The ability of Compounds 1 and 2 to inhibit DDR1 autophosphorylation was studied in U2OS cells stimulated with collagen. The amount of activated DRR1 (Y543) was measured using Western blot analysis, the obtained data were normalized to HA and GAPDH protein levels. Dasatinib served as a positive control and showed high potency with an IC50 value of 1 nM. It was found that Compounds 1 and 2 significantly block DDR1 autophosphorylation in a dose-dependent manner with IC50 values of 10.3 and 5.8 nM, respectively (FIGS. 8A-8I). These values are close to the activities observed in biochemical assays for both compounds.

Figure 9A:
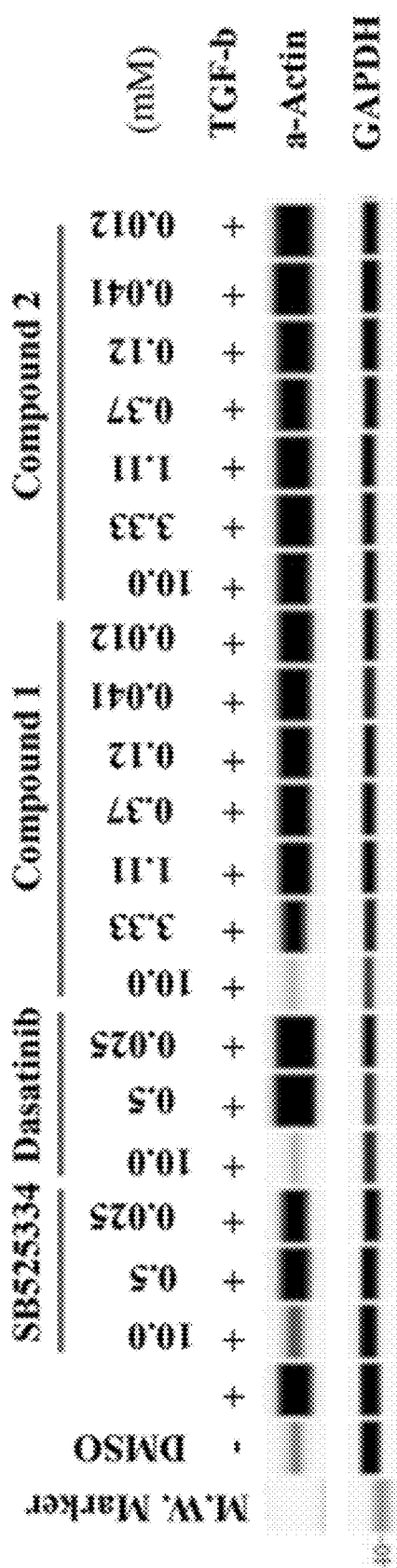
FIGS. 9A-9F include data that show the effects of compounds 1 and 2 on cellular fibrosis markers α-actin and CTGF (normalized to GAPDH) in MRC-5 cells.
Figure 9D:
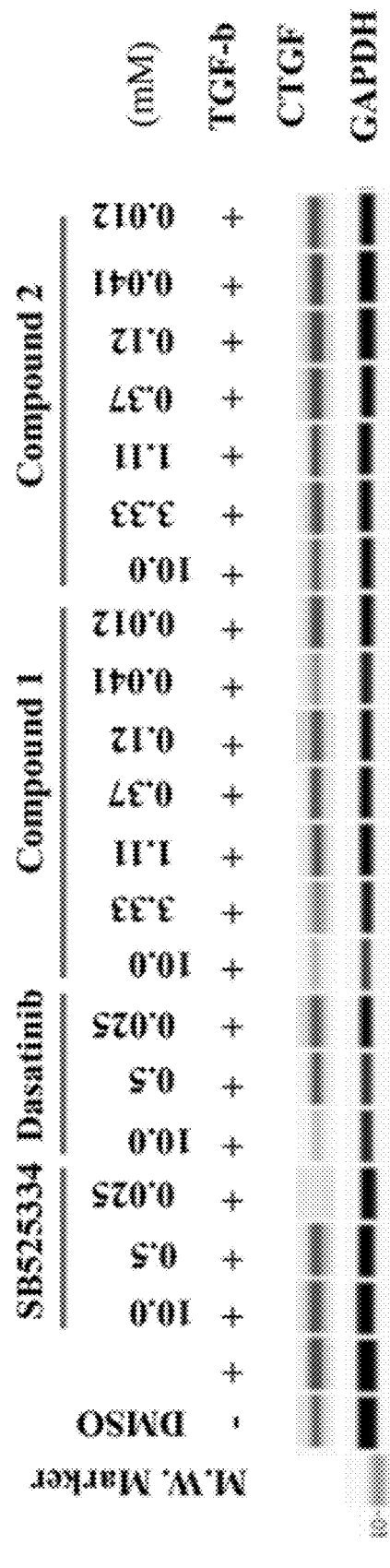
Figure 9B:
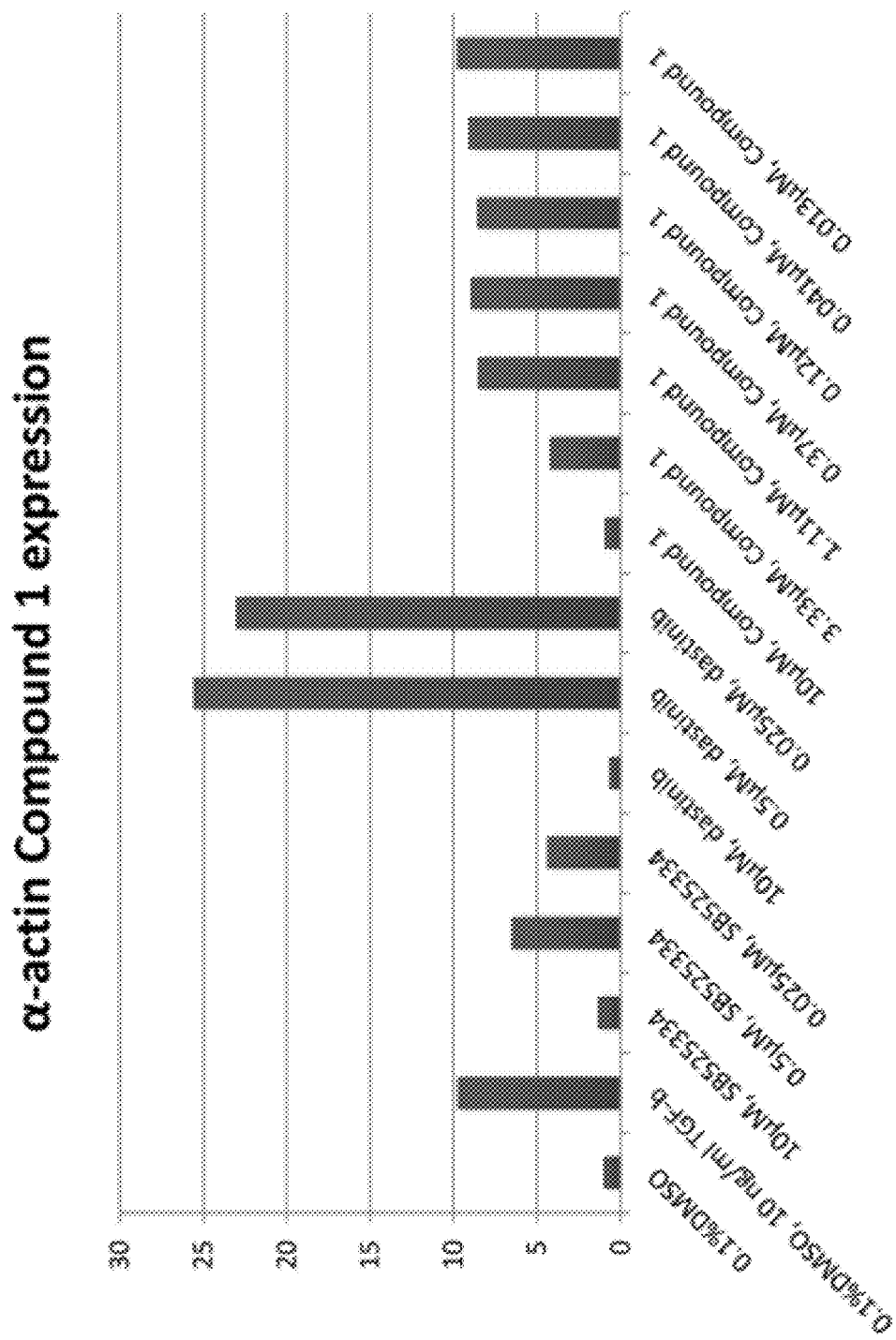
Figure 9C:
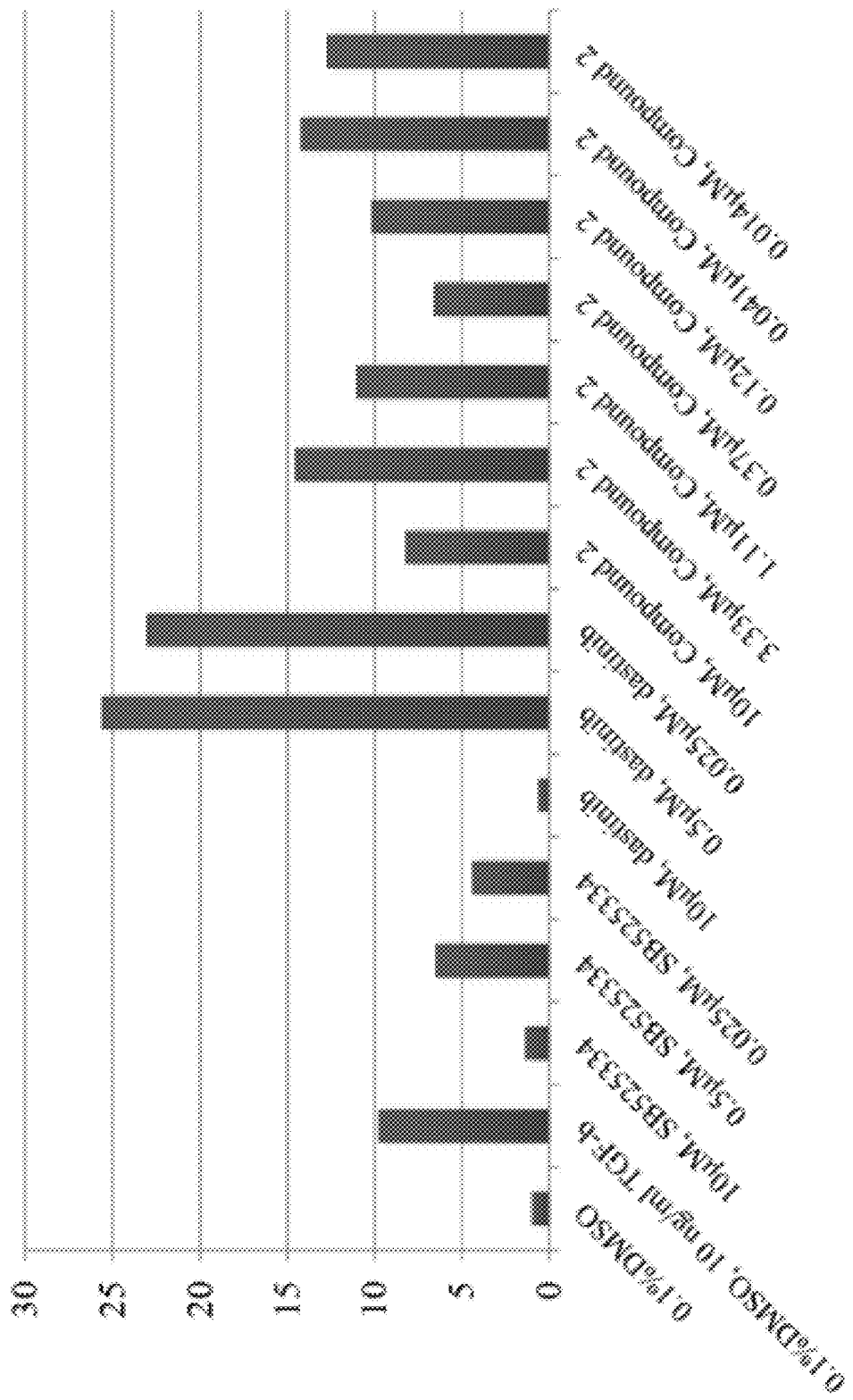
Figure 9E:
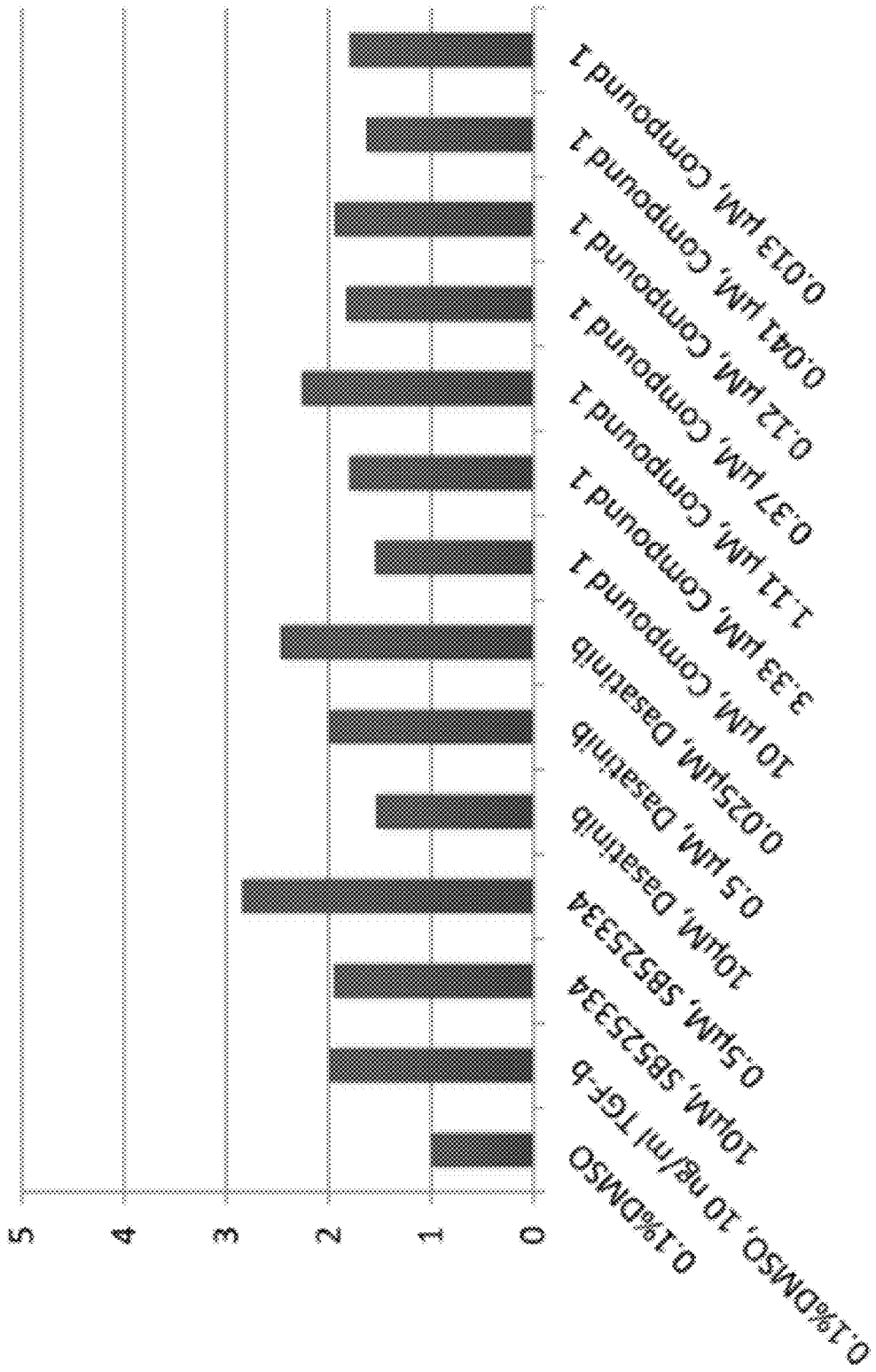
Figure 9F:
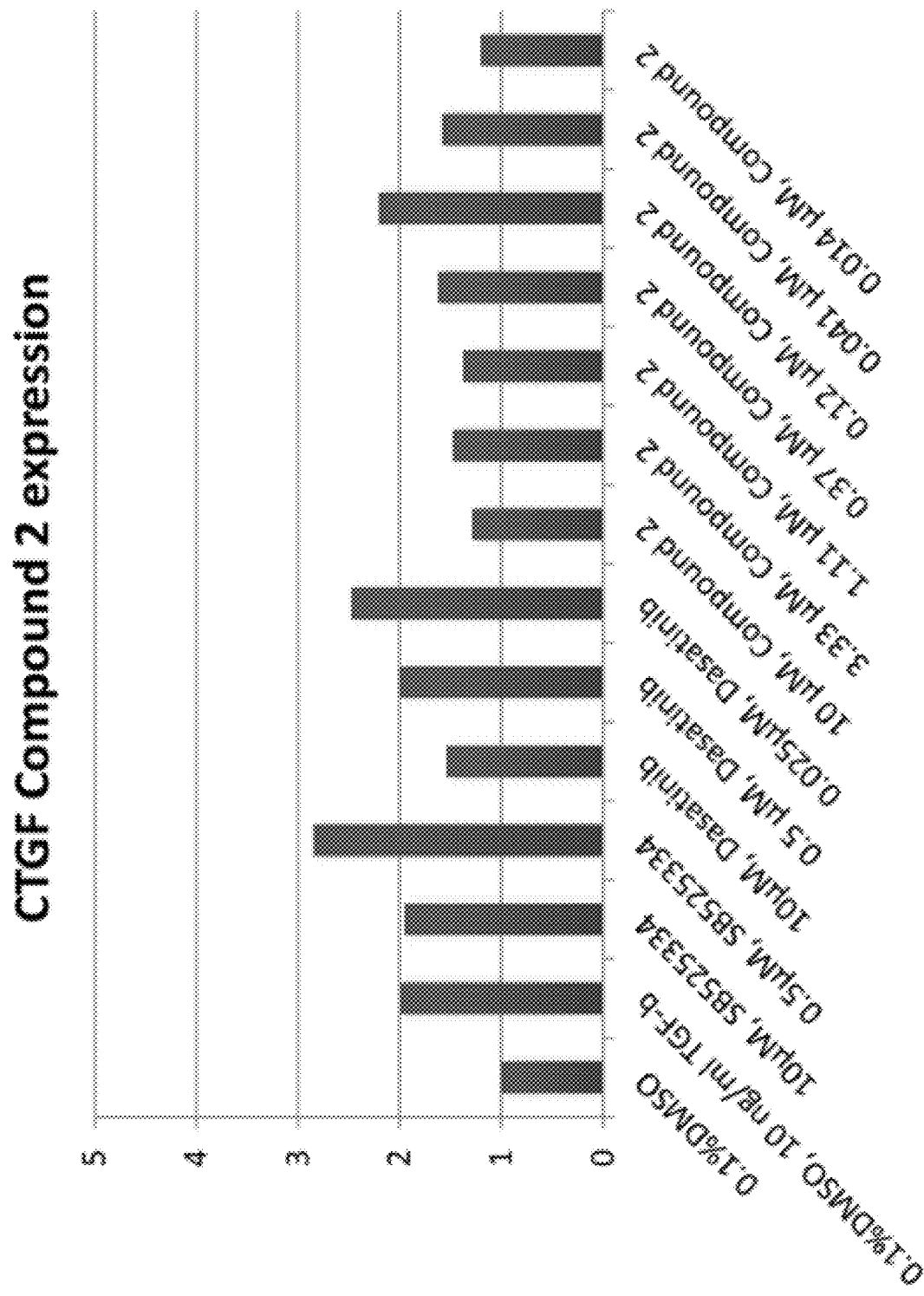

Antifibrotic activity of Compounds 1 and 2 was assessed using MRC-5 cell line as shown in FIGS. 9A-9F. Four antibodies were used to assess the antifibrotic effect of the selected molecules in comparison with two reference compounds, SB-525334[44] (TGFBR1 inhibitor, $IC_{50}$=5-15 nM) and dasatinib[45] (unselective kinase inhibitor, including DDR1 and DDR2, $IC_{50}$~15-30 nM), which were used as a positive control, while DMSO (0.1%) was used as a negative control. The obtained Western Blot results are depicted in FIG. 9A. As shown in FIGS. 9B-9C, DMSO demonstrated no effect in the test system, while the addition of TGF-β (10 ng) led to enhanced α-actin expression (up to 9.3-fold) and CTGF expression (2-fold). Unclear dose-dependent effect was observed for SB-525334, the maximum inhibition rate close to the negative control baseline was achieved at 10 μM (as for dasatinib), while at 0.5 μM we observed 2-fold reduction in α-actin expression level as compared to TGF+ DMSO stimulation. In contrast, at 0.5 μM and upper concentrations dasatinib showed a significant stimulation effect. SB-525334 (10 μM) slightly reduced CTGF expression (by 1.5-fold), whereas at 0.5 μM it had no effect (FIGS. 9E-9F). Dasatinib, at all the concentrations used, demonstrated only stimulation effect with no signs of inhibition. For Compound 1 the most inhibition potency against α-actin expression was achieved at 10 μM close to that determined for SB-525334 and dasatinib, while Compound 2 was less active. The maximum effect was observed at 0.37 μM (1.5-fold). Compound 1 demonstrated a robust dose-dependent effect in contrast to other molecules. In CTGF assay, Compound 1 had no inhibition potency at all the concentrations used, however, at 0.013 μM it demonstrated antifibrotic activity equal to that determined for SB-525334 at 38-fold higher concentration. Compound 2 showed the highest activity close to the negative control at 0.041 μM, and it was more active than both SB-525334 and dasatinib.

Besides the lung fibrosis model, the antifibrotic effect of the inhibitors Compound 1 and Compound 2 was also studied in a human hepatic stellate cell line LX-2 assay. Collagen α1, α-SMA, CTGF and GAPDH were traced using Western blot analysis. DMSO and SB-525334 were used as negative and positive controls, respectively. The unshown data shows the effects of Compounds 1 and 2 on cellular fibrosis markers collagen α1, α-actin and CTGF (normalized to GAPDH) in LX-2 cells.

Treatment with TGF-β induced collagen α1, α-SMA and CTGF production in LX-2 cells. SB-525334 strongly inhibited collagen al and α-actin expression in the concentration range from 0.5 to 10 μM, however at lower concentrations we observed a significant decrease in activity. The data normalized to GAPDH level has clearly demonstrated, that Compound 1 strongly inhibits collagen production in a dose-dependent manner with an IC50 value of 13 nM in TGF-β stimulated LX-2 cells. The highest inhibition of α-actin production was observed at a concentration of 41 nM, while in CTGF assay Compound 1 did not show the inhibition effect. Taking into account nanomolar potency of the molecule in enzymatic, autophosphorylation and fibrotic assays, the consistent translation from the biochemical to cellular activities has been clear and firm. Noteworthy, the IC50 value of Compound 1 in LX-2 assay significantly exceeds cytotoxicity (CC50=3.3 μM) against the same cell line. It was found that Compound 2 has micromolar activity (IC50>10 μM) in collagen assay. At a lower concentration between 3.3 and 0.014 μM, Compound 2 did not inhibit collagen al production. At the concentration of 14 nM it prevented almost a half of CTGF production (43%) and slightly inhibited α-SMA (15%). However, these effects diminished with increasing concentration. Compound 2 demonstrated low cytotoxicity in LX-2 cells with a CC50 value of 7.3 μM. Based on these preliminary results, it can be tentatively concluded that novel compounds can be reasonably regarded as having good antifibrotic activity.

Since Compound 2 contains an imidazolidine fragment typically unusual in drug discovery we experimentally assessed key properties for this molecule. Thus, kinetic solubility for Compound 2 at pH=7.4 was 1.09 μg/ml, while thermodynamic solubility was <0.59 μg/ml, log D 7.4 was 4.07 (TFA salt), and pKa=6.99. The inhibition activity of Compounds 1 and 2 towards a small panel of key cytochrome P450 (CYP450) isoforms was also assessed in vitro (Table 2).

TABLE 2

| | IC50 | | | | |
| --- | --- | --- | --- | --- | --- |
| | $IC_{50}(\mu M)$ | | | | |
| Compound ID | CYP1A2 | CYP2C9 | CYP2C19 | CYP2D6 | CYP3A4-M |
| Compound 1 | 7.36 | >50 | >50 | >50 | >50 |
| Compound 2 | 10.6 | 2.70 | 6.56 | 6.97 | 7.36 |

It was found that Compound 1 inhibited the activity of CYP1A2 with an IC50 value of 7.36 μM, while it was inactive against CYP2C9, CYP2C19, CYP2D6, and CYP3A4 (IC50>50 μM). Compound 2 demonstrated higher inhibition with IC50 values of 10.6, 2.70, 6.56, 6.97, and 7.36 μM, respectively. Both compounds did not show a significant CYP45 inhibition. Their CYP45 activities are much lower than the target nanomolar potency thereby providing a good selectivity index which is comparable to that observed for many drugs (including kinase inhibitors. The detailed description of the performed assay is provided in supporting information. Metabolic stability of Compound 2 (10 μM) was evaluated in human, SD rat, CD-1 mouse, and beagle dog liver microsomes (Table 3).

TABLE 3

Microsomal stability results summary for Compound 2

| Sample Name | $R^2$ | $T_{1/2}$ (min) | $CL_{int(mic)}$ (gL/min/ing) | $CL_{int(liver)}$ (mL/min/kg) | Remaining (T = 60 min) | Remaining (*NCF = 60 min) |
|---|---|---|---|---|---|---|
| HLM 0.5 | | | | | | |
| Compound 2 | 0.8843 | 12.8 | 108.2 | 97.3 | 2.8% | 88.7% |
| Testosterone | 0.9998 | 15.6 | 88.6 | 79.7 | 6.9% | 82.4% |
| Diclofenac | 0.9964 | 10.7 | 129.9 | 116.9 | 1.9% | 87.9% |
| Propafenone | 0.9868 | 8.3 | 166.3 | 149.7 | 0.7% | 103.3% |
| RLM 0.5 | | | | | | |
| Compound 2 | 0.9272 | 17.2 | 80.6 | 145.0 | 7.1% | 88.3% |
| Testosterone | 1.0000 | 1.1 | 1309.5 | 2357.2 | 0.0% | 86.8% |
| Diclofenac | 0.9934 | 23.6 | 58.7 | 105.7 | 17.5% | 89.8% |
| Propafenone | 0.9897 | 1.5 | 895.7 | 1612.3 | 0.4% | 87.1% |
| DLM 0.5 | | | | | | |
| Compound 2 | 0.9614 | 8.5 | 162.6 | 234.1 | 0.6% | 99.9% |
| Testosterone | 0.9988 | 17.5 | 79.4 | 114.3 | 9.5% | 88.6% |
| Diclofenac | 0.6896 | >145 | <9.6 | <13.8 | 85.7% | 96.9% |
| Propafenone | 0.9458 | 8.2 | 169.8 | 244.5 | 0.6% | 101.6% |
| MLM 0.5 | | | | | | |
| Compound 2 | 0.9226 | 15.1 | 91.8 | 363.6 | 5.3% | 86.0% |
| Testosterone | 0.9975 | 3.4 | 409.4 | 1621.1 | 0.0% | 75.4% |
| Diclofenac | 0.9347 | 58.5 | 23.7 | 93.8 | 50.2% | 91.8% |
| Propafenone | 0.9654 | 2.9 | 472.2 | 1869.7 | 0.4% | 88.0% |

*NCF: the abbreviation of no co-factor. No NADPH regenerating system is added into NCF sample (replaced by buffer) during the 60 min-incubation, if the NCF remaining is less than 60%, then Non-NADPH dependent occurs
$R^2$ is the correlation coefficient of the linear regression for the determination of kinetic constant (see raw data worksheet)
$T_{1/2}$ is half life and $CL_{int(mic)}$ is the intrinsic clearance
$CL_{int(mic)}$ = 0.693/half life/mg microsome protein per mL
$CL_{int(liver)}$ = $CL_{int(mic)}$ * mg microsomal protein/g liver weight * g liver weight/kg body weight mg microsomal protein/g liver weight: 45 mg/g for 5 species
Liver weight: 88 g/kg, 40 g/kg, 32 g/kg, 30 g/kg and 20 g/kg for mouse, rat, dog, monkey and human.

In human microsomes, Compound 2 demonstrated the half life time (t½) of 12.8 min and an intrinsic clearance value (human liver weight 20 g/kg, Clint/liver) of 97.3 mL/min/kg. For instance, under the same conditions, testosterone, diclofenac, and propafenone showed the following values: t½=15.6, 10.7, 8.3 min, and Clint/liver=79.7, 116.9, 149.7 mL/min/kg, respectively. Based on the obtained results, it is concluded that Compound 2 shows a relatively good metabolic stability as compared to the control molecules. It should be especially noted that the metabolic reaction for all the tested compounds proceeded only in the presence of NADPH regenerating system which was added into the sample (2.8% of Compound was remained after 60 min-incubation), while without NADPH we observed that 88.7% of Compound 2 was unmodified based on LC/MS/MS data. The remaining amounts of testosterone, diclofenac, and propafenone were 6.9%, 1.9%, and 0.7%, respectively. This clearly indicates that Compound 2 is quite stable under the assay conditions. The detailed summary of the metabolic stability of Compound 2 as well as the control molecules is presented in supporting information. In addition, we assessed the stability of Compound 2 (10 μM) in phosphate buffer (50 mM, pH=7.4) and MOPS/EDTA (8 mM/0.2 mM, pH=7.0). The samples were incubated for 0, 120, 240, 360, and 1440 min then subjected immediately for LC/MS/MS analysis. Thus, under the assay conditions Compound 2 was very stable (the remaining amount of the compound was close to 100% at each time point, see Table 4).

TABLE 4

Buffer stability results for Compound 2

| Buffer | Comp. ID | Final Conc. | Incubation Time (min) | Analyte Peak Area | IS1(Labetalol) Peak Area | IS2(tolbutamide) Peak Area | PAR | Mean (n = 2) | % Remain | % CV |
|---|---|---|---|---|---|---|---|---|---|---|
| 50 mM phosphate buffer, pH 7.4 | 2 | 10 μM | 0 | 1929905 | 6033253 | 2370965 | 0.81 | 0.82 | 100.00 | |
| | | | | 1897033 | 5767532 | 2312289 | 0.82 | | | |
| | | | 120 | 2014536 | 5997906 | 2443293 | 0.82 | 0.82 | 100.65 | 0.35 |
| | | | | 1993993 | 6362157 | 2430358 | 0.82 | | | |
| | | | 240 | 1959004 | 6227270 | 2506330 | 0.78 | 0.79 | 97.05 | 1.98 |
| | | | | 1927245 | 6082958 | 2395458 | 0.80 | | | |
| | | | 360 | 2143657 | 6248040 | 2497383 | 0.86 | 0.82 | 100.07 | 7.03 |
| | | | | 1900890 | 6111501 | 2446086 | 0.78 | | | |
| | | | 1440 | 2030579 | 5699870 | 2293050 | 0.89 | 0.88 | 107.23 | 1.61 |
| | | | | 2002559 | 5723871 | 2309804 | 0.87 | | | |

TABLE 4-continued

Buffer stability results for Compound 2

| Buffer | Comp. ID | Final Conc. | Incubation Time (min) | Analyte Peak Area | IS1(Labetalol) Peak Area | IS2(tolbutamide) Peak Area | PAR | Mean (n = 2) | % Remain | % CV |
|---|---|---|---|---|---|---|---|---|---|---|
| 8 mM MOPS pH 7.0, 0.2 mM EDTA, pH 7.0 | 2 | 10 µM | 0 | 1562845 | 6211850 | 2369241 | 0.66 | 0.64 | 100.00 | |
| | | | | 1603841 | 6233248 | 2576393 | 0.62 | | | |
| | | | 120 | 1573942 | 6034502 | 2394434 | 0.66 | 0.65 | 101.41 | 1.60 |
| | | | | 1627098 | 6275956 | 2530982 | 0.64 | | | |
| | | | 240 | 1649971 | 6239927 | 2452320 | 0.67 | 0.67 | 103.81 | 1.62 |
| | | | | 1542025 | 6088004 | 2343021 | 0.66 | | | |
| | | | 360 | 1694387 | 6053386 | 2438806 | 0.69 | 0.68 | 106.18 | 3.11 |
| | | | | 1631932 | 6188803 | 2448220 | 0.67 | | | |
| | | | 1440 | 1709036 | 6175205 | 2435887 | 0.70 | 0.68 | 105.37 | 5.76 |
| | | | | 1625303 | 6005431 | 2502723 | 0.65 | | | |

Additionally, the binding interactions of Compound 1 in the target kinase were analyzed using the DDR1 crystal structure (PDB code: 3ZOS) by molecular docking. The putative binding mode reveals several characteristics featuring the type II inhibition mechanism of the protein kinase (data not shown). The procedure of molecular docking was performed using Schrodinger Maestro. It was found that the N1 of the imidazopyridazine scaffold forms the conserved hinge interaction with Met704. The C(2)H of the scaffold also engages a pseudo-hydrogen bond with the backbone of Asp702. Connected via the ethynyl linker, the 6-methylbenzoisoxazole moiety exhibits an orthogonal geometry to the hinge element, a conformation required for the DFG-out pocket. Strong contacts are established by the isoxazole via hydrogen bond with Asp784 of the DFG motif, as well as π-cation interaction with the catalytic Lys655. Occupying the hydrophobic pocket opened up by the DFG motif, the CF3-phenyl group of Compound 1further stabilizes the binding complex by close contacts with Ile675, Met676, Leu679, Ile684, Ile685, Leu757 and Ile782. The exocyclic amine hydrogen bonds with Glu672, which is part of the extensive hydrogen bond and/or charge network consisting of Lys655, Glu672 and Asp784. In total, Compound 1 forms multiple hydrogen bonds, favorable charge and hydrophobic interactions with the active site residues of DDR1 kinase. The outstanding complementarity of Compound 1 to the ATP site prerequisites corroborates its potent inhibitory activity against DDR1.

This workflow protocol has demonstrated that deep generative networks with reinforcement learning can be used to generate novel active molecules and provide a reasonably high hit rate. The complexity of achieving a balance of desirable activity, specificity, selectivity, solubility, bioavailability, synthetic accessibility, and many other properties requires target and therapeutic-area specific modeling, which can be performed with the workflow protocol described herein. The generative models can provide hit compounds with higher levels of complexity and higher levels of novelty.

Methods
Reference DDR1 Small-Molecule Inhibitors.

The dataset of compounds with reported activity against DDR1 kinase was prepared using available databases, scientific publications, and patent records: 63 molecules were received from Thomson Reuters Integrity[49] and ChEMBL[50] databases, 77 compounds were obtained from literature, and 1230 structures were collected manually from patent records. Overall, the final dataset included 1370 compounds.

Pre-Training Dataset.

For the pre-training procedure, we have prepared a dataset of structures using Clean Leads set from the ZINC database[51] and proprietary databases from our partners. We have removed structures with undesirable atoms other than C, N, O, S, F, Cl, Br and H. Routine medicinal chemistry filters were applied to exclude compounds with potentially toxic and reactive groups. The resulted dataset contained approximately 1.9 million structures in the form of canonical SMILES. The dataset was parsed in order to collect a vocabulary of 34 unique tokens, such as atom symbols, brackets, and other SMILES-specific syntax elements. The average length of a string was 36 tokens, and the maximum length was 58 tokens.

Kinase Inhibitors and "Negative" Dataset.

The dataset of active and inactive molecules against various kinases was prepared using the data available in the Integrity Database. More than 56,000 unique structures of kinase inhibitors were collected and analyzed in terms of chemical diversity. Using standard clustering and diversity sorting procedures[52], the dataset was reduced to the size of 23K unique structures. The second part of the dataset containing 17,000 compounds with high diversity in structure with activity towards other targets was prepared based on ChEMBL database.

Compounds from Patent Records by Priority Date.

The dataset of structures claimed in patent records since 1950 by Big Pharma (Top-10 pharmaceutical companies in 2017)[53] as new drug substances was collected using the Integrity Database. A priority date was assigned for all the compounds included. A filtration procedure was performed in order to collect only unique records and resulted in 22,000 compounds. The structures underwent the following preparation procedure: salt part removing, error correction, filtration (non-drug-like elements, isotopes), clustering and cluster normalization, outlier exclusion, as well as duplicates elimination. The final dataset contained 17,000 records.

Model.

In the heart of our generative pipeline was GENTRL, a variational autoencoder with a rich prior distribution in the latent space (FIG. 11), which is a generative tensorial reinforcement learning model. The GENTRL model includes a learning and generation space 200 and a generation strategy space 208 tailored for a specific biological target. The GENTRL model includes a chemical dataset 202 that can include the types of groups of compounds as described herein. The chemical dataset 202 is input (e.g., as input vectors) into the encoder 204 and processed to generate the compounds in the latent space 206. The latent space is conditioned with the medicinal chemistry filter (MCF) 210, medicinal chemistry evolution (MCE) 212, and the pIC50 214. The latent space 206 utilizes a generation strategy by a generator 215 that generates compounds in the latent space 218, which are then filtered by rewards 220, such as the SOM rewards (e.g., trending SOM, General SOM, and specific SOM). The latent space 206 outputs the results into the generator 216 to generate the generated compounds 222 in the chemical space. These generated compounds can then be synthesized and validated as being biological active to the target. Thus, the training procedure consists of two parts. In the first stage we train a conditional model to learn the relation between molecular structures and properties. In the second stage, we explore the chemical space to find promising molecules with high reward.

The GENTRL model uses tensor decompositions to encode the relations between molecular structures and their properties. The GENTRL model is trained in a semi-supervised fashion without imputing the missing values. The code of the GENTRL model is available at github.com/insilicomedicine/gentrl.

The tensor-train decomposition[54] approximates high-dimensional tensors with a relatively small number of parameters. A joint distribution $p(r_1, r_2, \ldots, r_n)$ of discrete random variables $r_i \in \{0, \ldots N_i-1\}$ can be represented as elements of n-dimensional tensor:

$$p(r_1, r_2, \ldots, r_n) = \frac{1}{Z} 1_m \cdot \prod_{i=1}^{n} Q_i[r_i] \cdot 1_m^T,$$

where tensors $Q_i \in \mathbb{R}_+^{N_i \times m \times m}$ are cores, $1_m$ is a vector of ones, and Z is a normalizing constant. With larger core sizes, we better approximate the distribution, although the number of parameters grows quadratically with core size 7. In tensor-train, we can efficiently marginalize the distribution with respect to any variable:

$$p(r_1, \ldots, r_{k-1}, r_{k+1}, \ldots, r_n) = \frac{1}{Z} 1_m \cdot \left(\prod_{i=1}^{k} Q_i[r_i]\right) \cdot \tilde{Q}_k \cdot \left(\prod_{i=k+1}^{k} Q_i[r_i]\right) \cdot 1_m^T,$$

Where $\tilde{Q}_k = \Sigma_{r_i} Q_k[r_i]$ can be computed efficiently. With marginal distributions, we can compute conditional distributions and sample using a chain rule. The normalizing constant Z is given by:

$$Z = \Pi_{i=1}^{n} \tilde{Q}_i.$$

Since generative autoencoders use continuous latent codes, we use continuous tensor-train representation. For simplicity of notation, assume that latent codes z are continuous, and properties y are continuous. We approximate distributions $p_\psi(z_i)$ as mixtures of Gaussians with components index $s_i$. The joint distribution on z and y is:

$$p_\psi(z,y) = \Sigma_{s_1, \ldots, s_d} p_\psi(s,z,y) = \Sigma_{s_1, \ldots, s_d} p_\psi(s,y) p_\psi(z|y,s)$$

For conditional distribution $p_\psi(z|y,s)$, we select a fully factorized Gaussian that does not depend on y:

$$p_\psi(z|y,s) = p_\psi(z|s) = \Pi_{k=1}^{d} N(z_k | \mu_{k,s_k}, \sigma_{k,s_k}^2)$$

The tunable parameters of the distribution $p_\psi$ are tensor-train cores $Q_i$, means $\mu_{k,s_k}$ and variances $\sigma_{k,s_k}^2$ of the Gaussian components. We store tensor W in a tensor-train format. The resulting distribution becomes:

$$p_\psi(z,y) = \Sigma_{s_1, \ldots, s_d} P[s,y] \Pi_{k=1}^{d} N(z_k | \mu_{k,s_k}, \sigma_{k,s_k})$$

Our model is a variational autoencoder with a prior distribution $p_\psi(z,y)$, encoder $q_\phi$ and a decoder $p_\theta$. Consider a training example $(x, y_{ob})$, where x is a molecule, and $y_{ob}$ are its known properties. The evidence lower bound for our model is:

$$L(\theta, \phi, \psi) = \mathbb{E}_{q_\phi(z|x, y_{ob})}(\log p_\theta(x|z, y_{ob}) + \log p_\psi(y_{ob}|z)) - KL(q_\phi(z|x, y_{ob}) \| p_\psi(z|y_{ob}))$$

Since the molecule determines its properties, we assume that, $q_\phi(z|x, y_{ob}) = q_\phi(z|x)$. We also assume that $p_\theta(x|z, y_{ob}) = p_\theta(x|z)$, indicating that an object is fully defined by its latent code. The resulting evidence lower bound is:

$$L(\theta, \phi, \psi) =$$
$$\mathbb{E}_{q_\phi(z|x)}(\log p_\theta(x|z) + \log p_\psi(y_{ob}|z)) - KL(q_\phi(z|x) \| p_\psi(z|y_{ob})) \approx$$
$$\frac{1}{l} \Sigma_{i=1}^{l} \left[\log p_\theta(x|z_i) - \log \frac{q_\phi(z_i|x)}{p_\psi(z_i|y_{ob})} + \log p_\psi(y_{ob}|z_i)\right],$$

where $z_i \sim q_\phi(z|x)$. For the proposed joint distribution $p_\psi(z,y)$, we can compute the posterior distribution on the latent codes given observed properties $p_\psi(z|y_{ob})$ analytically.

By maximizing the evidence lower bound, we train and autoencoder and a prior on a dataset described above: we sample molecules in a SMILES format from the dataset along with their properties (e.g., conditions), including MCE-18, $pIC_{50}$ (negative log of the IC50), and a binary feature indicating if a molecule passed MCFs. We train this model and obtain a mapping from the chemical space to the latent codes. This mapping is aware of the relation between molecules and their physicochemical properties.

In the next stage of training, we fine-tuned the model towards inhibitors of the specific biological target (e.g., DDR1 kinase inhibitors). We used reinforced learning (RL) to expand the latent manifold towards novel inhibitors with reward functions described in the next section (e.g., general kinase SOM, specific kinase SOM, and trending SOM). We used the REINFORCE[55] algorithm (also known as a log-derivative trick) to directly optimize the model:

$$\max_\psi \mathbb{E}_{z \sim p_\psi(z)} R(z), \ R(z) = \mathbb{E}_{x \sim p_\theta(x|z)} R_{general}(x) + R_{specific}(x) + R_{trending}(x)$$

$$\nabla_\psi \mathbb{E}_{z \sim p_\psi(z)} R(z) = \mathbb{E}_{z \sim p_\psi(z)} \nabla_\psi \log p_\psi(z) \cdot R(z)$$

We reduced the variance of the gradient, we used a standard variance reduction technique called a "baseline"—after calculating the rewards for all molecules in the batch, we subtracted the average reward in a batch from each reward:

$$\nabla_\psi \mathbb{E}_{z \sim p_\psi(z)} R(z) \approx \frac{1}{N} \Sigma_{i=1}^{N} \nabla_\psi \log p_\psi(z_i) \left[R(z_i) - \frac{1}{N} \Sigma_{j=1}^{N} R(z_j)\right]$$

Figure 11:
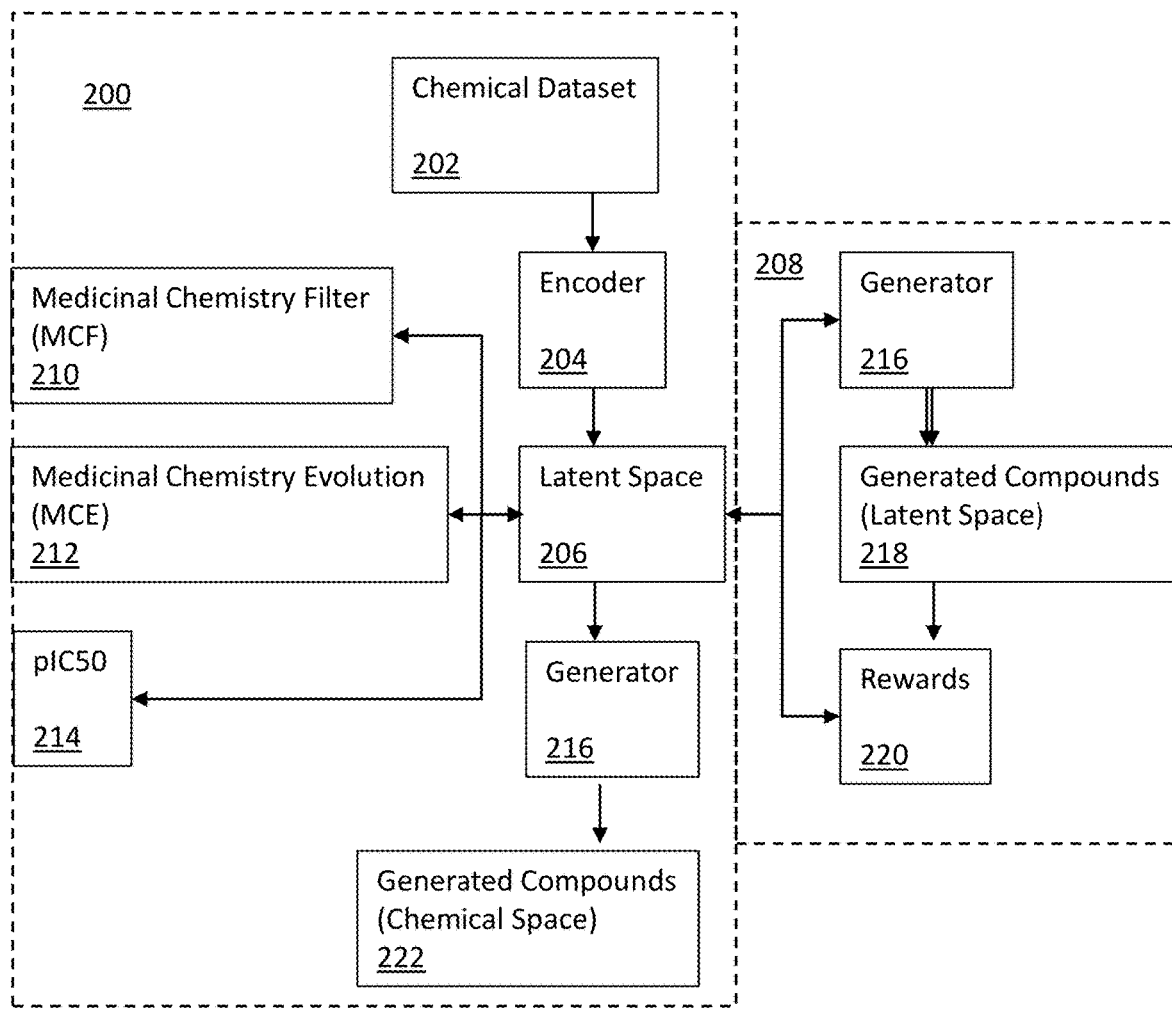
FIG. 11 illustrates an example of a chemical generating system platform in accordance with the workflow and generative model.

To preserve the mapping of the chemical space, we fixed the parameters of the encoder and decoder and only trained the manifold distribution $p_\psi(z)$. We combined exploration and exploitation approaches. For the exploration, we sampled $z^{explore} \sim \mathcal{N}(\mu, (2\sigma)^2)$ outside from the currently explored latent space, where the $\mu$ and $\sigma^2$ are mean and the variance of $p_\psi(z)$ for all dimensions. If the reward $R(z^{explore})$ for a newly-discovered area was high, the latent manifold expanded towards it (FIG. 11 Generation strategy 208).

The comparison of generative chemistry models is very important for the advancement of this emerging field, and there are several benchmarking platforms in development[56, 57]. We successfully compared the performance of GENTRL with the previous approaches such as ORGAN[38,39], RANC[18] and ATNC[17] and provide the training details in supporting information.

The proposed pipeline performed well for the generation of inhibitors for the biological target (e.g., DDR1 inhibitors). In some aspects, the workflow protocol can perform proper hyperparameter tuning and exploration, and configure GENTRL so that it is not prone to mode collapse. This can be done by tracking the entropy of $p_\psi(z)$ and increasing the exploration rate if the entropy drops too quickly. Also, if some of the promising molecules are far outside the exploration region $\mathcal{N}(\mu(2\sigma)^2)$ the model will never discover them. It can also be helpful to use special multi-objective reinforcement learning techniques to balance the performance on all rewards. Finally, for some tasks we found it beneficial to train the decoder together with the latent space during the reinforcement learning training.

Reward Function.

A reward function was developed on the basis of Kohonen SOM (FIG. 12A-12D). FIGS. 12A-12D show a smoothed representation of the General Kinase and Trending SOMs This algorithm was introduced by Teuvo Kohonen[58] as a unique unsupervised machine-learning dimensionality reduction technique. It can effectively reproduce an intrinsic topology and patterns hidden into the input chemical space in a faithful and unbiased fashion. The input chemical space is usually described in terms of molecular descriptors (input vector), while, at the output, 2D- or 3D-feature map convenient for visual inspection is generated. An ensemble of three SOMs was used as a reward function: the first SOM was trained to predict the activity of compounds against kinases (general kinase SOM, $R_{general}$) (e.g., general biological target family SOM), the second one was developed to select compounds located in neurons associated with DDR1 inhibitors within the whole kinase map (specific kinase SOM, $R_{specific}$) (e.g., specific biological target SOM), and the last one was trained to assess the novelty of chemical structures in terms of the current trends in medicinal chemistry (trending SOM, $R_{trending}$). During learning, the generative model was rewarded when the generated structures were classified as molecules acting on kinases, positioned in neurons attributed to DDR1 inhibitors as well as tended to be a relatively novel.

Trending SOM.

Figure 12A:
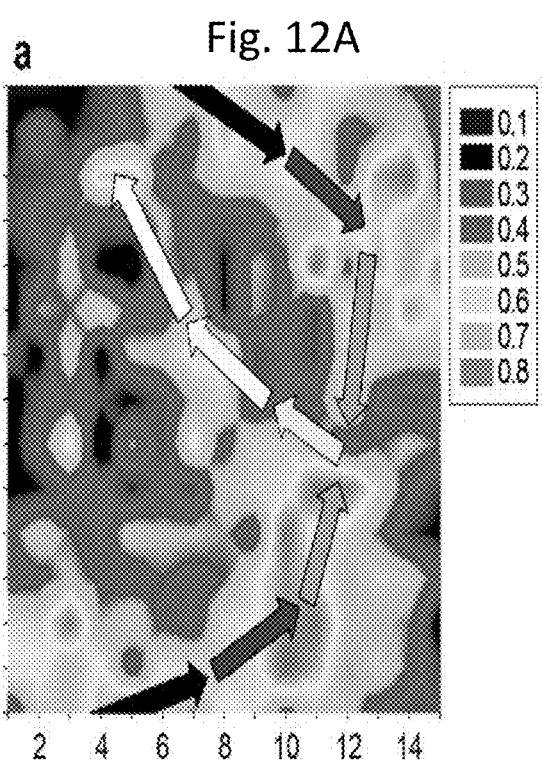
FIGS. 12A-12D show images of implementation of a reward function based on Kohonen SOMs.
Figure 12B:
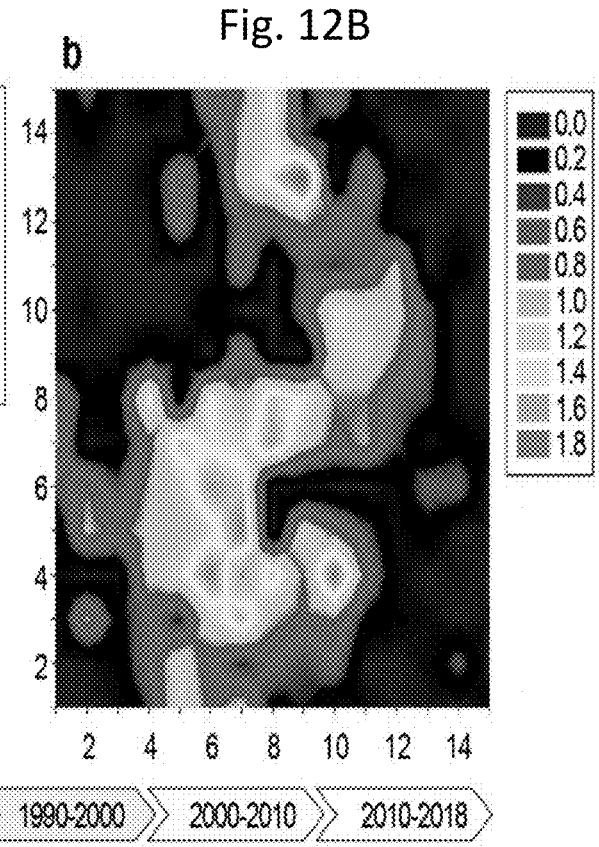
Figure 12C:
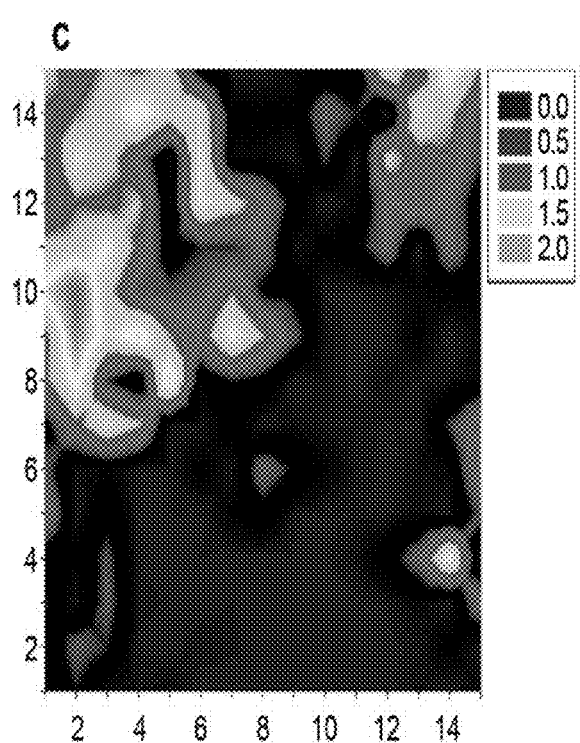
Figure 12D:
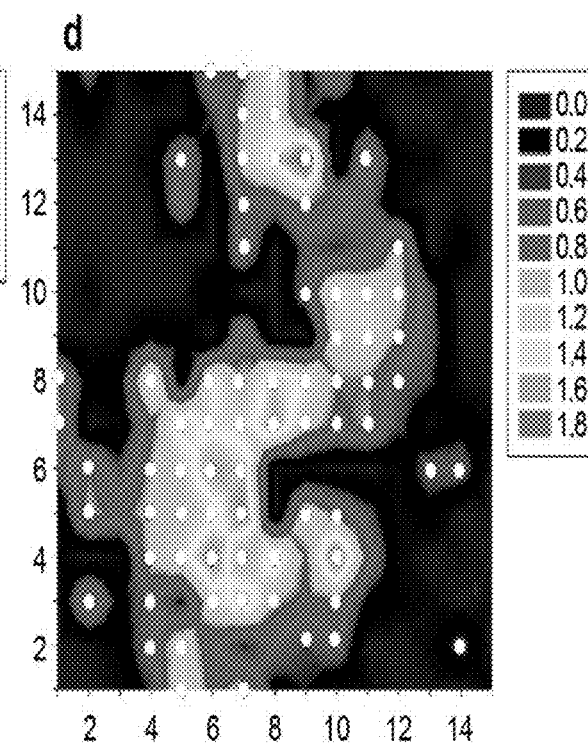

As an additional reward function, we also used the Kohonen map which was developed based on the training dataset of molecules by the top ten pharmaceutical companies, claimed in the intellectual property records with an assigned priority date. The following key molecular descriptors were selected for training procedure: MW, Log P (lipophilicity, the calculated partition coefficient in octanol-1/water system), Log $S_w$ (solubility in water), PSA (polar surface area, $Å^2$), HBA, HBD, SS, MCE-18 (medicinal chemistry evolution). The MCE-18 function correlates well with the chemical evolution and reflects true non-planarity of molecules vs. simple and false-positive $sp^3$-rate. MCE-18 is a sufficiently sensitive to follow the tendencies observed in modern medicinal chemistry in terms of novelty. The map size was 15×15 2D-representation (random distribution threshold was 75 molecules per neuron), learning epochs: 2000, initial learning rate: 0.4 (linear decay), initial learning radius: 10, winning neurons were determined using Euclidean distance. The initial weight coefficients were generated using a random distribution. After the training process was completed, the areas containing compounds claimed in different time periods were displayed (FIG. 12A). As shown in FIG. 12A, molecules which have been described in relatively novel patent records (claimed between 2015-2018) are located in a separate region of the map, whereas "vecchio" structures are positioned predominantly in radically distinct areas providing a statistically relevant separation. Within the map, we have clearly observed an intrinsic trend through the years and depict it as a set of simple vectors. Neurons attributed to novel structures (the last decade) were used to reward our AI-core in contrast to neurons associated with "ancient" chemotypes.

General Kinase SOM.

Figure 13:
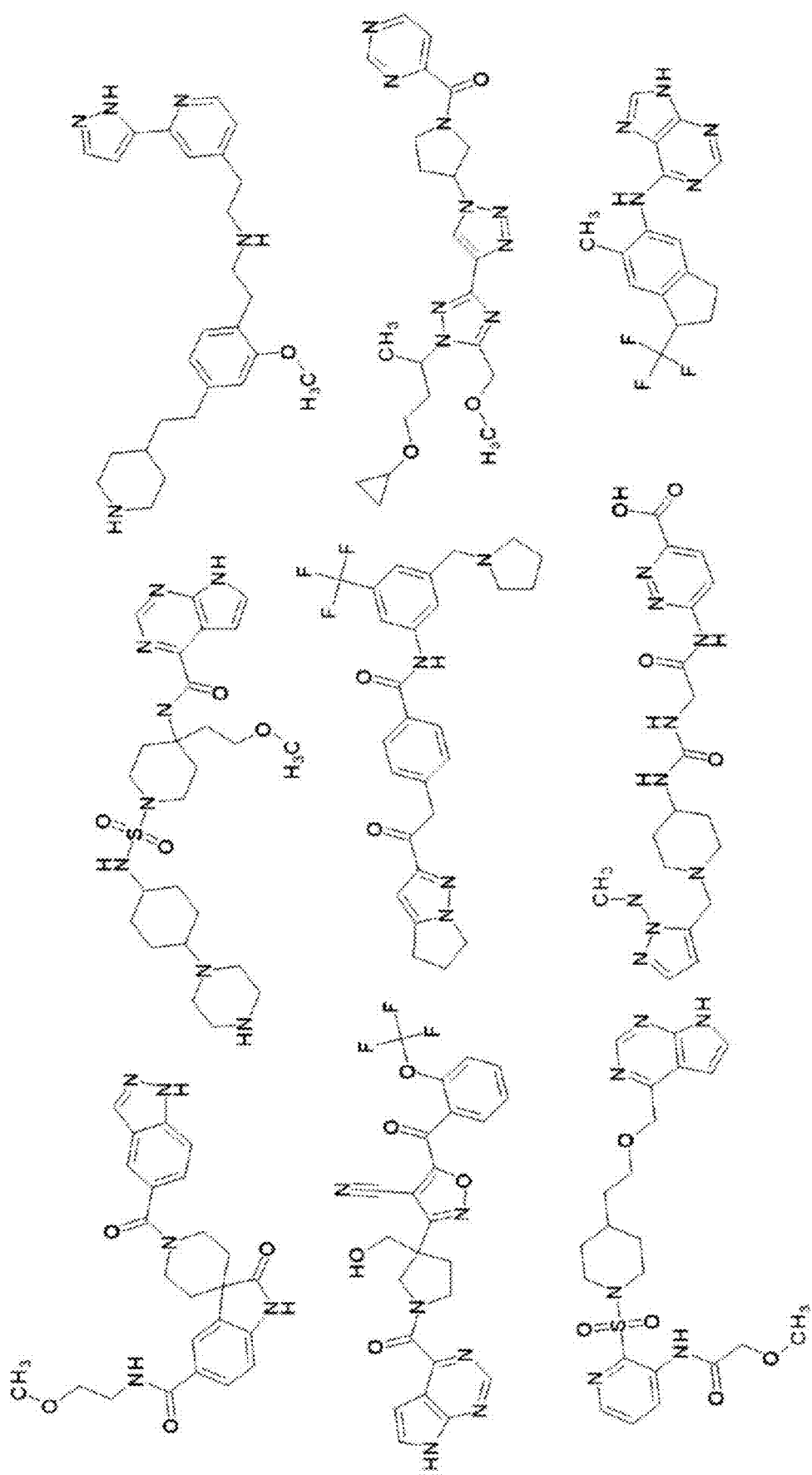
FIG. 13 shows examples of rejected molecules.

The pre-processed training dataset included of total 41,000 small-molecule compounds: 24,000 kinase inhibitors and 17,000 molecules with the reported activity (at the concentration of <1 µM) against non-kinase targets. For the whole database more than 2K molecular descriptors were calculated using RDKit[59], Mordred library[60], and SmartMining Software[61,62]. Descriptors were ranked in accordance with bivariate Student's t-values and then 9 descriptors were selected as the most privileged and theoretically valid for distinguishing between kinase and non-kinase chemistry. The set included: MW (molecular weight, t=−63.4), Q' (binormalized quadratic index, t=77.3), SS (common electrotopological index, t=−69.3), S[>C<] (partial SS index, t=−50.3), 1 Ka ($1^{st}$ Kier topological index, t=−66.5), Hy (hydrophilicity index, t=−55.9), $VDW^wvol$ (weighted atomic van der Waals volumes, t=−70), HBA (number of hydrogen bond acceptors, t=−34.0), HBD (number of hydrogen bond donors, t=−8.5), and RGyr (Radius of gyration, t=−55). The map size was 15×15 2D-representation (random distribution threshold was 177 molecules per neuron), learning epochs: 2000, initial learning rate: 0.3 (linear decay), initial learning radius: 8, winning neuron was determined using Euclidean metrics, initial weight coefficients: random distribution. After the training process was completed, the areas populated by kinase inhibitors and molecules acting on other biological targets were highlighted. We observed that compounds from these two categories were mainly located in distinct regions within the map (FIGS. 13B-13D). Neurons were then prioritized based on the following privileged factor (PF): $N_K^i(\%)/N_{NK}^i(\%)$, where N is the percent of kinase inhibitors located in i-th neuron, while $N_{NK}^i$ t is the percent of other molecules located in the same neuron and vice versa. PF value greater than 1.3 was used as a threshold to assign neurons to one of these two classes. Upon examination, there were no "dead" neurons within the map. The average classification accuracy was 84% with a random threshold. All the generated structures were scored using this model during learning cycles as well as at the prioritization step. Compounds which were classified as kinase inhibitors with the lowest error (Euclidean metrics) were subsequently subjected to the specific kinase SOM.

Specific Kinase SOM.

Similar procedure was performed to construct Kohonen map for the identification of nodes assigned with DDR1 inhibitors among the kinase inhibitors chemical space. Structures which were classified as kinase inhibitors by the general kinase SOM (vide supra) were used as an input chemical pool. The final set of molecular descriptors included: MW (t=−44), Q' (t=37), 1 Ka (t=−42), SS (t=−52), Hy (t=−30), $VDW^{sum}vol$ (t=−35), HBA (t=−40), and HBD (t=14). Map size was 10×10 2D-representation (random distribution threshold was 245 molecules per neuron), the learning settings were identical to that applied for the general kinase SOM, except the initial learning radius which was equal to six. After the map was constructed we identified neurons containing at least one DDR1 inhibitor. The formal average classification accuracy was 68% and the bias towards DDR1 inhibitors was observed. "Active" neurons were then used to select structures during the learning procedure to reward the core GENTRL and for the prioritization process. This case, we did not use PF for the selection decision to overcome over-training and to enhance novelty for the generated structures operating around close topographic proximity.

Pharmacophore Hypotheses.

On the basis of X-ray data available in PDB database (PDB codes: 3ZOS, 4BKJ, 4CKR, 5BVN, 5BVO, 5FDP, 5FDX, 6GWR), we have developed three pharmacophore models describing DDR1 inhibitors. In order to obtain the superposition of the ligands, 3D-alignment of the complexes was carried out. These 3-, 4- and 5-centered pharmacophore hypotheses contain key features responsible for binding to the active site of DDR1 kinase including hydrogen bond acceptor at the hinge region, aromatic/hydrophobic linker and hydrophobic center in the pocket located in proximity to DFG motif. For the detailed information on pharmacophore features and distances see FIGS. 2A-2C.

Nonlinear Sammon Mapping.

To make the final selection we used Sammon-based mapping technique[63]. The main goal of this algorithm lies in the approximation of local geometric and topological relationships hidden in the input chemical space on a visually intelligible 2D- or 3D-dimensional plot. The fundamental idea of this method is to substantially reduce the high dimensionality of the initial dataset into the low-dimension feature space, and, in this aspect, it resembles SOM approach and multidimensional scaling. However, in contrast to other algorithms, classical Sammon-based method allows scientists to construct a projection which reflects as global topographic relationships as pair-wise distances between all the objects within the whole space of input vector samples. Structures which successfully passed all the selection procedures described above were used as an input chemical space. For mapping, we used the same set of molecular descriptors which was applied for specific kinase SOM and added RMSD values obtained during pharmacophore modeling as additional inputs. Euclidean distances were used as a similarity metric, stress threshold: 0.01, interaction number: 300, optimization step: 0.3, structural similarity factor: 0.5. The resulting map (FIG. 3) demonstrates that structures are normally distributed within the Sammon plot.

Molecule Generation and Selection Procedure.

Using the GENTRL model, we generated 30,000 unique valid structures by sampling latent codes from the learned manifold $p_\psi(z)$ and sampling structures from the decoder distribution $p_\theta(x|z)$. To select the batch of molecules for synthesis and biological studies, we have developed a prioritization pipeline (for the examples of rejected molecules see FIG. 13). At initial step, the dataset was reduced to the size of 12,147 compounds using the following molecular descriptor thresholds: $-2<\log P<7$, $250<MW<750$, HBA+HBD<10, TPSA<150, NRB<10. After that, 150 MCFs were applied to remove potentially toxic structures and compounds containing reactive and undesirable groups. These include: substrates for 1,4-addition (Michael-bearing moieties) and other electrophilic species (e.g. para- or ortho-halogen substituted pyridines, 2-halogen substituted furans and thiophenes, alkyl halides, aldehydes and anhydrides, etc.), disulfides, isatins, barbiturates, strained heterocycles, fused polyaromatic systems, detergents, hydroxamic acids and diazo-compounds, peroxides, unstable fragments as well as sulfonyl ester derivatives. In addition, we used more trivial filtering rules including the following: <2NO$_2$ groups, <3Cl, <2Br, <6F, <5 aromatic rings, undesired atoms, like Si, Co or P, to reasonably reduce the number of structures spread within the entire chemical space to a more compact and drug-like biased. This procedure resulted in 7912 structures. A clustering analysis was then performed based on Tanimoto similarity and standard Morgan fingerprints implemented in the RDKit package. All compounds that satisfied 0.6 similarity threshold were assigned to the same cluster, with minimum value of 5 structures per cluster. Inside each cluster, the compounds were sorted according to their internal dissimilarity coefficient[52] to output top 5 items with the maximum diversity in structure. As the result, the dataset was reduced to 5542 molecules. Then, we performed a similarity search using vendors' collections (MolPort[64] and ZINC[51]) and additionally removed 900 compounds with similarity >0.5 to increase the novelty of the generated structures. General kinase SOM and specific kinase SOM were used to prioritize the compounds by their potential activity against DDR1 kinase. Out of 2570 molecules classified as kinase inhibitors by general kinase SOM, 1951 molecules were classified as DDR1 inhibitors by specific kinase SOM and were used for pharmacophore-based virtual screening. For every molecule, 10 conformations were generated and minimized using RDKit's implementation of Universal Force Field (UFF)[65]. Using the developed hypotheses, the screening procedure was then performed and resulted in a set of RMSD values for 848 molecules matching at least one pharmacophore hypothesis. On the basis of Sammon mapping we have performed the random selection procedure placing special attention to the areas of RMSD values obtained for 4- and 5-centered pharmacophores (Table 5). As a result, 40 molecules were selected for synthesis and subsequent biological evaluation.

TABLE 5

RMSD values (Å) for 40 molecules matching the pharmacophore hypothesis

| ID | 3c_rmsd | 4c_rmsd | 5c_rmsd |
|---|---|---|---|
| INS015_001 | 0.21 | 1.18 | NA |
| INS015_002 | 0.18 | 0.68 | 1.25 |
| INS015_003 | 0.31 | 0.80 | 0.96 |
| INS015_004 | 0.44 | 1.01 | 1.37 |
| INS015_005 | 0.18 | 0.79 | 1.23 |
| INS015_006 | 0.50 | 1.07 | NA |
| INS015_007 | 0.39 | 0.82 | 1.34 |
| INS015_008 | 0.32 | 0.67 | 0.96 |
| INS015_009 | 0.24 | 0.66 | 0.83 |
| INS015_010 | 0.34 | 0.87 | 1.08 |
| INS015_011 | 0.09 | 0.43 | NA |
| INS015_012 | 0.47 | 1.05 | 1.19 |
| INS015_013 | 0.07 | 0.13 | NA |
| INS015_014 | 0.35 | 0.77 | 1.35 |
| INS015_015 | 0.14 | 0.84 | 0.94 |
| INS015_016 | 0.21 | 0.75 | 0.83 |
| INS015_017 | 0.48 | 0.76 | 1.08 |
| INS015_018 | 0.45 | 0.70 | 0.99 |
| INS015_019 | 0.18 | 0.38 | NA |
| INS015_020 | 0.38 | 0.92 | 1.01 |
| INS015_021 | 0.15 | 0.97 | 1.30 |
| INS015_022 | 0.63 | 1.12 | NA |
| INS015_023 | 1.07 | 1.00 | NA |
| INS015_024 | 0.89 | 1.05 | NA |

TABLE 5-continued

RMSD values (Å) for 40 molecules
matching the pharmacophore hypothesis

| ID | 3c_rmsd | 4c_rmsd | 5c_rmsd |
|---|---|---|---|
| INS015_025 | 0.49 | 0.65 | 1.52 |
| INS015_026 | 0.06 | 0.99 | 0.91 |
| INS015_027 | 0.55 | 0.92 | NA |
| INS015_028 | 0.75 | 0.98 | NA |
| INS015_029 | 0.41 | 0.52 | 1.41 |
| INS015_030 | 0.60 | 1.32 | NA |
| INS015_031 | 0.15 | 0.35 | 0.72 |
| INS015_032 | 0.40 | 0.77 | 0.99 |
| INS015_033 | 0.17 | 0.41 | 0.79 |
| INS015_034 | 0.19 | 0.50 | 0.66 |
| INS015_035 | 0.18 | 0.84 | 0.82 |
| INS015_036 | 0.25 | 0.55 | 0.79 |
| INS015_037 | 0.94 | 1.38 | NA |
| INS015_038 | 0.43 | 0.85 | 1.28 |
| INS015_039 | 0.31 | 0.57 | 1.54 |
| INS015_040 | 0.72 | 0.65 | 1.29 |

3c_rmsd—RMSD value for a compound matched 3-centered pharmacophore hypothesis
4c_rmsd—RMSD value for a compound matched 4-centered pharmacophore hypothesis
5c_rmsd—RMSD value for a compound matched 5-centered pharmacophore hypothesis
NA—a compound did not match pharmacophore hypothesis Ab Initio Calculation Details.

We carried out first-principles calculations to the lowest conformer as predicted with the RDKit/UFF methodology above. The geometry optimization was performed using local correlated coupled-cluster method including single and double excitations (LCCSD) with the 6-31++G basis set. Final energies were calculated at the LCCSD(T) level of theory. The localized Pipek-Mezey procedure was used for obtaining the initial molecular orbitals.

Docking Simulations.

Molecular modeling was performed in the Maestro suite[66]. PDB structure 3ZOS was preprocessed and energy minimized using the Prep module. The binding site grid was generated around the ATP binding site with 20 Å buffer dimensions. Docking poses were generated by extra-precision (XP) Glide runs using the optimized ligand structure. The final model was selected based on its lowest docking score of −15 kcal/mol.

Cytochrome Inhibition.

Water used in the assay and analysis was purified by ELGA Lab purification systems. Potassium phosphate buffer (PB) in concentration of 100 mM and $MgCl_2$ in concentration of 33 mM were used. Test compounds (Compound 1 and Compound 2) and standard inhibitors (α-naphthoflavone, sulfaphenazole, (+)-N-3-benzylnirvanol, quinidine, ketoconazole) working solutions (100×) were prepared. Microsomes were pulled out of the −80° C. freezer to thaw on ice, labeled the date and put back to freezer immediately after using. 20 μL of the substrates solutions were added to corresponding wells. 20 μL PB were added to Blank wells. 2 μL of the test compounds and positive control working solution were added to corresponding wells. Then, HLM working solution was prepared. 158 μL of the HLM working solution was added to all wells of incubation plate. The plate was pre-warmed for about 10 min at 37° C. water bath. Then, NADPH cofactor solution was prepared. 20 μL NADPH cofactor was added to all incubation wells. The solution was mixed and incubated for 10 minutes at 37° C. water bath. At the time point, the reaction was terminated by adding 400 μL cold stop solution (200 ng/mL Tolbutamide and 200 ng/mL Labetalol in ACN). The samples were centrifuged at 4000 rpm for 20 minutes to precipitate protein. 200 μL supernatant was transferred to 100 μL HPLC water and shaken for 10 min. XL fit was used to plot the percent of vehicle control versus the test compound concentrations, and for non-linear regression analysis of the data. $IC_{50}$ values were determined using 3- or 4-parameter logistic equation. IC50 values were reported as ">50 μM" when % inhibition at the highest concentration (50 μM) is less than 50%. See Table 2.

Microsomal Stability.

Microsomal stability of Compound 2 was accessed as follows: working solutions of Compound 2 and control compounds (testosterone, diclofenac, propafenone) were prepared. The appropriate amount of NADPH powder (β-Nicotinamide adenine dinucleotide phosphate reduced form, tetrasodium salt, NADPH.4Na, Vendor: Chem-impex international, Cat. No. 00616) was weighed, and diluted into $MgCl_2$ (10 mM) solution (work solution concentration: 10 unit/mL; final concentration in reaction system is 1 unit/mL). The appropriate concentration microsome working solutions (human: HLM, Cat No. 452117, Corning; SD rat: RLM, Cat No. R1000, Xenotech; CD-1 mouse: MLM, Cat No. M1000, Xenotech; Beagle dog: DLM, Cat No. D1000, Xenotech) was prepared with 100 mM potassium phosphate buffer. Cold acetonitrile (ACN) including 100 ng/mL Tolbutamide and 100 ng/mL Labetalol as internal standard (IS) were used for stop solution. 10 μL compound or control working solution/well was added to all plates (T0, T5, T10, T20, T30, T60, NCF60) except matrix blank. Dispense 80 μL/well microsome solution was added to every plate by Apricot, the mixture of microsome solution and compound were incubated at 37° C. for about 10 min. After pre-warming, dispense 10 μL/well NADPH regenerating system was added to every plate by Apricot to start reaction. The solution was then incubated at 37° C. 300 (μL/well) stop solution (cold in 4° C.) was added to terminate the reaction. The sampling plates were shaken for approximately 10 min. Samples were centrifuged at 4000 rpm for 20 min under 4° C. While centrifuging, 8×new 96-well plate were loaded with 300 μL HPLC water, then 100 μL supernatant was transferred and mixed for LC/MS/MS. See Table 3.

Buffer Stability.

The stability of compound 2 was accessed in phosphate buffer (pH=7.0 and pH=7.4). Test compounds (at 10 μM) were incubated at 25° C. with 50 mM phosphate buffer, pH=7.4 and 8 mM MOPS pH 7.0, 0.2 mM EDTA, pH=7.0. Duplicate samples were used. Time samples (0, 120, 240, 360 and 1440 min) were removed and immediately mixed with cold 50% acetonitrile/water containing internal standard (IS). Curcumin was used as positive control in this assay at neutral-basic condition. Samples were analyzed by LC/MS/MS, disappearance of test compound was assessed based on peak area ratios of analyte/IS (no standard curve). See Table 4.

Hyperparameters for GENTRL Model.

Architecture.

The encoder $q_\varphi(z|x)$ was a 2-layer recurrent neural network with gated recurrent units (GRU)[69] of hidden size 128. The decoder $p_\theta(x|z)$ was a 7-layer stacked dilated convolutions with 128 channels. The latent space z was 50 dimensional with 10 mixture components at each dimension. Core size of a tensor-train m was 30.

Autoencoder Training:

We used multiple molecular properties y for learning the mapping of the chemical space onto a latent manifold. For all training molecules, we calculated MCE-18 and a binary flag MCF indicating if a molecule successfully passed medicinal chemistry filters. For molecules from a Kinase and "negative" dataset, we specified if a molecule was a kinase (for molecules outside these datasets the value was unknown). For known DDR1 inhibitors, we specified $pIC_{50}$. For each update, we constructed a batch containing 200 molecules: 60 active molecules from DDR1, 60 molecules from ZINC, 20 molecules from Kinase dataset, 20 from the negative dataset and 40 molecules from the patent records. We used an Adam[70] optimizer with a learning rate of $10^{-4}$ and ran the optimization procedure for 300,000 updates.

Reinforcement Learning:

We trained a model with the REINFORCE algorithm for 2,000 updates with Adam optimizer, learning rate $2 \cdot 10^{-5}$ and a batch size 200. We sampled exploratory batches $z^{explore}$ with probability 0.1 and standard batches $z \sim p_\psi(z)$. Estimated from 50,000 randomly sampled molecules, 97.8% were valid and 73% were unique.

Biological Studies.

Biochemical Assay.

The experimental procedures were performed by Eurofins. The activity of the molecules against hDDR1 and hDDR2 kinases was assessed using KinaseProfiler[67]. The enzyme sample was incubated with 8 mM MOPS buffer (pH=7.0), 0.2 mM EDTA, 250 µM target protein hDDR1 and hDDR2 kinases, 10 mM Magnesium acetate/Manganese chloride, respectively, and [γ-$^{33}$P]-ATP. The enzymatic reaction processed in the presence of $Mg^{2+}$ cations and ATP at room temperature for 40 minutes and terminated by addition of phosphoric acid. The reaction mixture (10 µL) was spotted onto a P30 filtermat and washed four times using 0.425% phosphoric acid and once with methanol. All the compounds were prepared in 100% DMSO. Staurosporine was used as a reference inhibitor and was added to each plate at an estimated concentration resulted in complete inhibition. The biological evaluation of selectivity against non-target kinases was performed in Dundee Eurofins, using Scan Max Delta Panel [10 µM ATP] KinaseProfiler[68].

Auto-Phosphorylation.

Human DDR1b gene with HA-tag was cloned into pCMV Tet-On vector (Clontech) and stable inducible cell lines established in U2OS were used for the $IC_{50}$ test. The cells were seeded in 12-well plates and DDR1b expression was induced with 10 pg/ml doxycycline (Selleckchem #S4163) for 48 h at 37° C. in a humidity controlled incubator with 5% $CO_2$ prior to DDR1 activation by rat tail collagen I (sigma #11179179001). The cells were detached with trypsinization and transferred to a 15-ml tube. Then, after being pre-treated with compound for 0.5 h, the cells were treated with compounds in the presence of 10 µg/ml rat tail collagen I for 1.5 h at 37° C. At the end of the treatment, each sample was washed with cold PBS one time and lysed in RIPA buffer with protease and phosphatase inhibitors (Sigma #0278, Sigma #P5726 and Sigma #P0044) for 20 min at 4° C. The lysates were cleared by centrifugation and the supernatants were subject to Western blot analysis for the activated human DDR1b (Y513) (Cell Signaling #14531S), total DDR1b (HA-tag, sigma #H9658) after stripping, and GAPDH. The integrated intensity of each band was quantified and the $IC_{50}$ values of the evaluated compounds were calculated on a 10-point 3-fold dilution series.

MRC-5 Fibrosis Assay.

MRC-5 cells were grown in Minimum Essential Medium Eagle (Sigma, M2279) supplied with 1% MEM Non-Essential Amino Acids (Invitrogen, 11140-050), 10% fetal bovine serum (Hyclone, SV30087.03), Penicillin (100 U/mL)-streptomycin (100 µg/mL) (Millipore, TMS-AB2-C) and 2 mM L-Glutamine (Invitrogen, 25030-001). After the cells grew in 12-well plates for 24 h, the cell culture medium was changed to the same as above except using 2% fetal bovine serum. After 20 h growth in the reduced serum medium, the cells were treated with indicated doses of compounds for 30 minutes. Subsequently, the cells were stimulated with 10 ng/mL TGF-β (R&D Systems, 240-B-002) for 48 or 72 hours. The cells were rinsed twice with DPBS before being harvested with 100 mL RIPA buffer (Sigma, R0278) supplemented with protease inhibitor cocktail (Roche, 04693132001) at 4° C. The total protein content in each sample was quantified using BCA Protein Assay Kit (Pierce™, 23227) and equal amount of total protein of each sample was loaded onto WES Automatic Western Blot System (ProteinSimple, Bio-techne) following the manufacturer's instruction. Antibodies used were mouse anti-α-Actin (SPM332) (sc-365970) and mouse anti-CTGF (E5) (sc-365970), from Santa Cruz Biotechnologies; and mouse anti-GAPDH (6C5) (EMD Millipore, MAB374).

LX-2 Fibrosis Assay.

Human hepatic stellate cells LX-2 were grown in DMEM (Invitrogen, 11960) supplied with 1% MEM Non-Essential Amino Acids (Invitrogen, 11140-050), 2% fetal bovine serum (Hyclone, SV30087.03), Penicillin (100 U/mL)-streptomycin (100 µg/mL) (Millipore, TMS-AB2-C) and 2 mM L-Glutamine (Invitrogen, 25030-001). After the cells grew in 12-well plates for 24 h, the cell culture medium was changed to the same as above except using 0.4% fetal bovine serum. After 20 h growth in the reduced serum medium, the cells were treated with indicated doses of compounds for 30 minutes. Subsequently, the cells were stimulated with 4 ng/mL TGF-β (R&D Systems, 240-B-002) for 48 h. The cells were rinsed twice with DPBS before being harvested with 100 µL RIPA buffer (Sigma, R0278) supplemented with protease inhibitor cocktail (Roche, 04693132001) at 4° C. The total protein in each sample was quantified using BCA Protein Assay Kit (Pierce™, 23227) and equal amount of total protein of each sample was subject to Western blot analysis. Antibodies used were mouse anti-α-Actin (SPM332) (sc-365970), mouse anti-CTGF (E5) (sc-365970), and mouse anti-collagen a1 (3G3) (sc-293182), from Santa Cruz Biotechnologies; and mouse anti-GAPDH (6C5) (EMD Millipore, MAB374).

Cytotoxicity.

LX-2 cells were seeded into 96 well plates in the presence of a compound and allowed to grow for 72 h before CellTiter-Glo® Luminescent Cell Viability Assay was carried out according the manufacturer's instruction. Cytotoxicity ($CC_{50}$) was calculated on a 10 dose 3-fold compound dilution series using GraphPad Prism software.

Physicochemical properties of Compounds 1 and 2 are shown in Table 6.

TABLE 6

| ID | MW | logP* | TPSA | HBD | HBA | $IC_{50}$ (nM) | N | LE** |
|---|---|---|---|---|---|---|---|---|
| 1 | 433.39 | 4.94 | 68.25 | 1 | 4 | 10 | 32 | 0.35 |
| 2 | 479.45 | 3.88 | 81.33 | 2 | 3 | 21 | 35 | 0.31 |

*Predicted
**LE = 1.4*(pIC50)/N, N – number of heavy atoms

Full mouse PK study results for 10 mg/kg Compound 1 IV administration. Formulation: 5 mg/mL in NMP/PEG400/H2O=1:7:2, clear solution are shown in Table 7.

TABLE 7

| | IV | | | | |
|---|---|---|---|---|---|
| | M01 | M02 | M03 | Mean IV SD | CV (%) |
| IV Time (h) | | | | | |
| 0.0830 | 2140 | 2810 | 2120 | 2357 ± 393 | 16.7 |
| 0.250 | 2000 | 2090 | 1760 | 1950 ± 171 | 8.75 |
| 0.500 | 1630 | 2070 | 1430 | 1710 ± 327 | 19.1 |
| 1.00 | 1400 | 1490 | 1170 | 1353 ± 165 | 12.2 |
| 2.00 | 893 | 886 | 862 | 880 ± 16.3 | 1.85 |
| 4.00 | 417 | 456 | 528 | 467 ± 56.3 | 12.1 |
| 8.00 | 244 | 261 | 261 | 255 ± 9.81 | 3.84 |
| 24.0 | 9.37 | 12.5 | 11.3 | 11.1 ± 1.58 | 14.3 |
| PK Parameters | | | | | |
| Rsq_adj | 0.993 | 0.996 | 0.999 | — ± — | — |
| No. points used for $T_{1/2}$ | 3.00 | 3.00 | 3.00 | 3.00 ± — | — |
| $C_0$ (ng/mL) | 2213 | 3255 | 2325 | 2598 ± 572 | 22.0 |
| $T_{1/2}$ (h) | 3.58 | 3.79 | 3.58 | 3.65 ± 0.123 | 3.36 |
| $Vd_{ss}$ (L/kg) | 5.24 | 4.85 | 5.55 | 5.21 ± 0.349 | 6.69 |
| Cl (mL/min/kg) | 19.8 | 18.0 | 19.3 | 19.1 ± 0.970 | 5.09 |
| $T_{last}$ (h) | 24.0 | 24.0 | 24.0 | 24.0 ± — | — |
| $AUC_{0-last}$ (ng · h/mL) | 6555 | 7223 | 6712 | 6830 ± 349 | 5.11 |
| $AUC_{0-inf}$ (ng · h/mL) | 6603 | 7291 | 6770 | 6888 ± 359 | 5.21 |
| $MRT_{0-last}$ (h) | 4.22 | 4.26 | 4.56 | 4.35 ± 0.187 | 4.29 |
| $MRT_{0-inf}$ (h) | 4.41 | 4.50 | 4.78 | 4.56 ± 0.193 | 4.23 |
| $AUC_{Extra}$ (%) | 0.732 | 0.938 | 0.863 | 0.845 ± 0.104 | 12.3 |
| $AUMC_{Extra}$ (%) | 4.85 | 6.15 | 5.27 | 5.42 ± 0.663 | 12.2 |

ND = Not determined (Parameters not determined due to inadequately defined terminal elimination phase)
BQL = Below the lower limit of quantitation (LLOQ)
If the adjusted rsq (linear regression coefficient of the concentration value on the terminal phase) is less than 0.9, T1/2 might not be accurately estimated.
If the % $AUC_{Extra}$ > 20%, $AUC_{0-inf}$, Cl, $MRT_{0-inf}$ and $Vd_{ss}$ might not be accurately estimated.
If the % $AUMC_{Extra}$ > 20%, $MRT_{0-inf}$ and $Vd_{ss}$ might not be accurately estimated.
The adjusted linear regression coefficient of the concentration value on the terminal phase is less than 0.9, $T_{1/2}$ might not be accurately estimated.
a: Bioavailability (%) was calculated using $AUC_{0-inf}$ (% $AUC_{Extra}$ < 20%) or $AUC_{0-last}$ (% $AUC_{Extra}$ > 20%) with administered dose Full mouse PK study results for 15 mg/kg Compound 1 PO administration. Formulation: 3 mg/mL in NMP/PEG400/H20=1:7:2, clear solution are shown in Table 8.

TABLE 8

| | PO | | | | |
|---|---|---|---|---|---|
| | M04 | M05 | M06 | Mean PO SD | CV (%) |
| PO Time (h) | | | | | |
| 0.250 | 65.4 | 203 | 47.1 | 105 ± 85.2 | 81.0 |
| 0.500 | 179 | 254 | 99.7 | 178 ± 77.2 | 43.5 |
| 1.00 | 291 | 322 | 185 | 266 ± 71.8 | 27.0 |
| 2.00 | 317 | 259 | 175 | 250 ± 71.4 | 28.5 |
| 4.00 | 226 | 200 | 189 | 205 ± 19.0 | 9.27 |
| 8.00 | 69.9 | 71.2 | 164 | 102 ± 54.0 | 53.1 |
| 24.0 | 2.18 | 3.85 | 3.33 | 3.12 ± 0.855 | 27.4 |
| PK Parameters | | | | | |
| Rsq_adj | 0.994 | 0.995 | 0.950 | — ± — | — |
| No. points used for $T_{1/2}$ | 3.00 | 4.00 | 3.00 | ND ± — | — |
| $C_{max}$ (ng/mL) | 317 | 322 | 189 | 276 ± 75.4 | 27.3 |
| $T_{max}$ (h) | 2.00 | 1.00 | 4.00 | 2.33 ± 1.53 | 65.5 |
| $T_{1/2}$ (h) | 3.04 | 3.59 | 3.24 | 3.29 ± 0.278 | 8.45 |
| $T_{last}$ (h) | 24.0 | 24.0 | 24.0 | 24.0 ± — | — |
| $AUC_{0-last}$ (ng · h/mL) | 1843 | 1841 | 2004 | 1896 ± 93.7 | 4.94 |
| $AUC_{0-inf}$ (ng · h/mL) | 1852 | 1860 | 2019 | 1911 ± 94.3 | 4.93 |
| $MRT_{0-last}$ (h) | 4.84 | 5.10 | 6.69 | 5.54 ± 1.000 | 18.0 |
| $MRT_{0-inf}$ (h) | 4.97 | 5.36 | 6.86 | 5.73 ± 0.999 | 17.4 |
| $AUC_{Extra}$ (%) | 0.517 | 1.07 | 0.771 | 0.787 ± 0.278 | 35.4 |

TABLE 8-continued

| | PO | | | | |
|---|---|---|---|---|---|
| | M04 | M05 | M06 | Mean PO SD | CV (%) |
| $AUMC_{Extra}$ (%) | 2.96 | 5.84 | 3.22 | 4.01 ± 1.60 | 39.8 |
| Bioavailability (%)[a] | — | — | — | 17.8 ± — | — |

ND = Not determined (Parameters not determined due to inadequately defined terminal elimination phase)
BQL = Below the lower limit of quantitation (LLOQ)
If the adjusted rsq (linear regression coefficient of the concentration value on the terminal phase) is less than 0.9, T1/2 might not be accurately estimated.
If the % $AUC_{Extra}$ > 20%, $AUC_{0-inf}$ Cl, $MRT_{0-inf}$ and $Vd_{ss}$ might not be accurately estimated.
If the % $AUMC_{Extra}$ > 20%, $MRT_{0-inf}$ and $Vd_{ss}$ might not be accurately estimated.
The adjusted linear regression coefficient of the concentration value on the terminal phase is less than 0.9, $T_{1/2}$ might not be accurately estimated.
[a]Bioavailability (%) was calculated using $AUC_{0-inf}$ (% $AUC_{Extra}$ < 20%) or $AUC_{0-last}$ (% $AUC_{Extra}$ > 20%) with administered dose Case Study The Generative Tensorial Reinforcement Learning (GENTRL) module was used to generate in vivo active DDR1 and DDR2 inhibitors (See FIGS. 1, 12, and 15) in a first case study. As described herein, the GENTRL module (e.g., model, or combination of models) is an Advanced VAE with RL optimization which prioritizes the synthetic feasibility of a compound, its effectiveness against a biological target, and how distinct it is from other molecules. The model training and validation was done using a set of molecules obtained from the ZINC database. Structures containing atoms other than carbon, nitrogen, oxygen, sulfur, fluorine, chlorine, bromine, and hydrogen were removed. MCFs were applied to exclude compounds with potentially toxic and reactive groups. In addition, a dataset of known DDR1 kinase inhibitors, a set of common kinase inhibitors (positive set), a set of molecules that act on non-kinase targets (negative set) and patent data for biologically active molecules that have been claimed by pharmaceutical companies were included. The Integrity database was used to collect the data set of structures claimed as new drug substances in patent records and 3D structures for DDR1 inhibitors.

The GENTRL module generated a total of 30,000 unique valid structures which were prioritized as follows. Firstly, the set was reduced to 12,147 compounds using molecular descriptor thresholds and MCFs were applied to remove potentially toxic structures and compounds containing reactive and undesirable groups. Then, filtering rules were used to exclude undesired atoms, such as silicon, cobalt or phosphorus. This procedure resulted in a subset of 7,912 structures. A subsequent clustering analysis based on the Tanimoto similarity and standard Morgan fingerprints resulted in a set of 5,542 molecules. General kinase SOM and specific kinase SOM were then used to prioritize the compounds by their activity against DDR1 kinase. 1,951 molecules were classified as DDR1 inhibitors and were used for pharmacophore-based virtual screening. On the basis of Sammon mapping, a random selection was performed, with a particular attention to the areas of RMSD values obtained for four- and five-centered pharmacophores.

The successive filtering steps further reduced the number of compounds into consideration. Based on the final scoring results, forty molecules were selected for subsequent biological evaluation. Six of them were chosen on the basis of their selectivity profiles and SA. These six compounds (e.g., Compounds 1-6) herein were tested for their in vitro inhibitory activity in an enzymatic kinase assay. The results showed that two compounds with favorable physicochemical properties strongly inhibited DDR1 activity while exhibiting selectivity towards DDR1. The pharmacokinetics of the most promising compound was tested in vivo using a rodent model.

A second case study The second case study (See FIGS. 1, 12, and 15) aimed at generating non-covalent inhibitors of the SARS-CoV-2 3C-like protease (Mpro). The reason to launch a program to design non-covalent inhibitors is that most of the initial efforts undertaken within the scientific community focused on the development of SARS-CoV-2 Mpro covalent inhibitors while the possibilities to identify non-covalent inhibitors remained less investigated. However, covalent inhibitors are not always suitable for treating patients due to the high probability of side effects while non-covalent inhibitors with their higher therapeutic index offer an alternative despite their reduced potency.

The methodology and time frame was similar to the DDR1 case study. The first step was to select, filter and process the datasets to be used for training and validation of the DL models. The main protease dataset was assembled with molecules active against proteases in enzymatic assays extracted from the Integrity database. The structural duplicates were excluded during the standardization procedure, and salt parts were removed. MCFs were applied to exclude non-drug-like molecules and structures containing cycles with more than 8 atoms and polypeptides. The final dataset contained 60,293 unique structures. To adapt the scoring metrics and the reward functions to the type of structures to be generated, a protease peptidomimetics dataset was extracted from the protease dataset using SMARTS queries for common peptidomimetic substructures. The final protease peptidomimetics dataset contained 5,891 compounds.

For the generation of the novel molecular structures, a ligand-based and a pocket-based approach was used. To that end, the pocket and ligand features were obtained from the binding site amino acid environment and from the co-crystallized fragment 6W63 derived from the same PDB record, respectively.

In total, 28 ML models were used to generate molecular structures. Those structures were optimized with RL based on a reward function that was a weighted sum of multiple intermediate rewards. This included medicinal chemistry and drug-likeness scoring, active chemistry scoring, structural scoring, novelty and diversity scoring and SA score. The ML models exploited different molecular representations, including fingerprints, string representations, and graphs. Every model optimized the reward function to explore the chemical space, investigate promising clusters, and generate molecular structures. These structures shared the structural patterns common to peptidomimetics. After successive filtering steps, 20 compounds were selected for synthesis and went further into biological evaluation which included enzymatic and cell-based antiviral essays.

Figure 14:
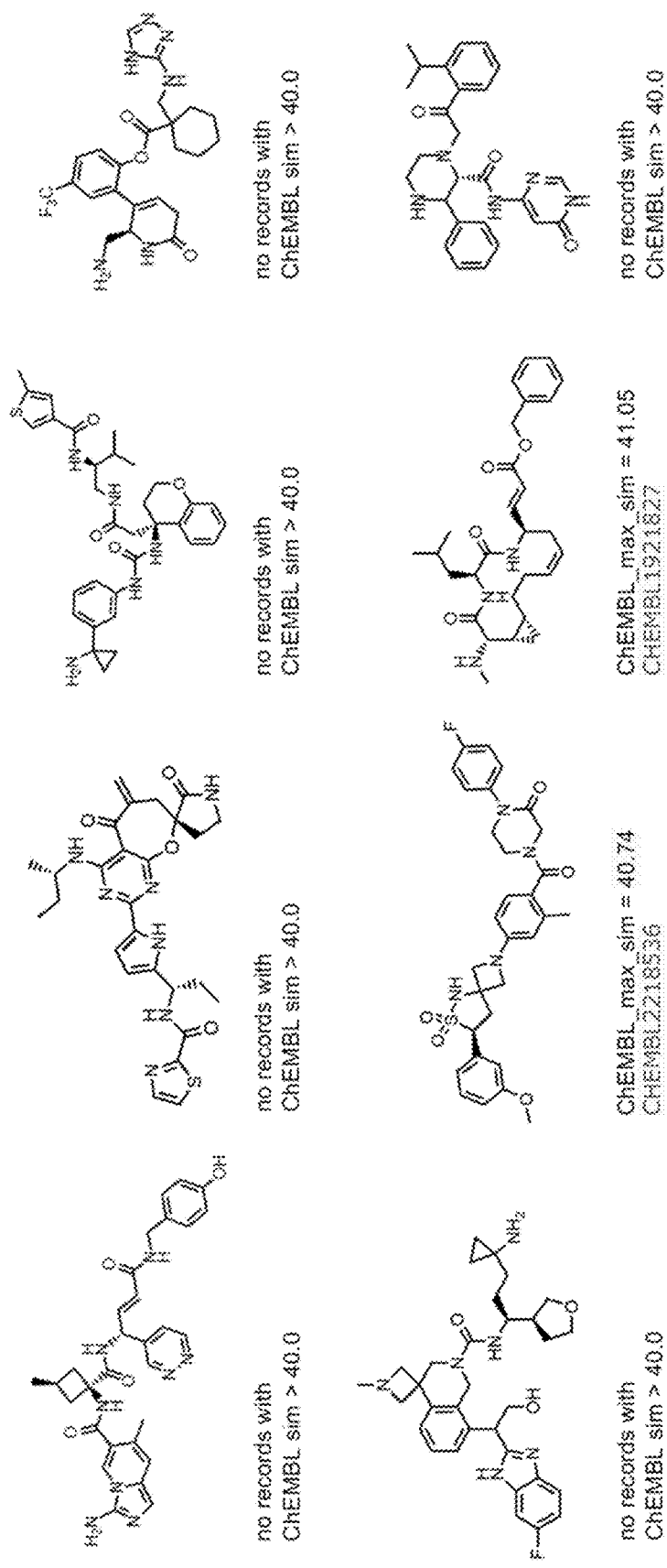
FIG. 14 shows examples of generated molecules provide by the GENTRL model.

Generated Structures:

The systems and methods described herein were used to generate a number of novel structures, which include a ChEMBL similarity score of <700). Some examples are shown herein, such as in FIG. 14.

For the models, and processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 15:
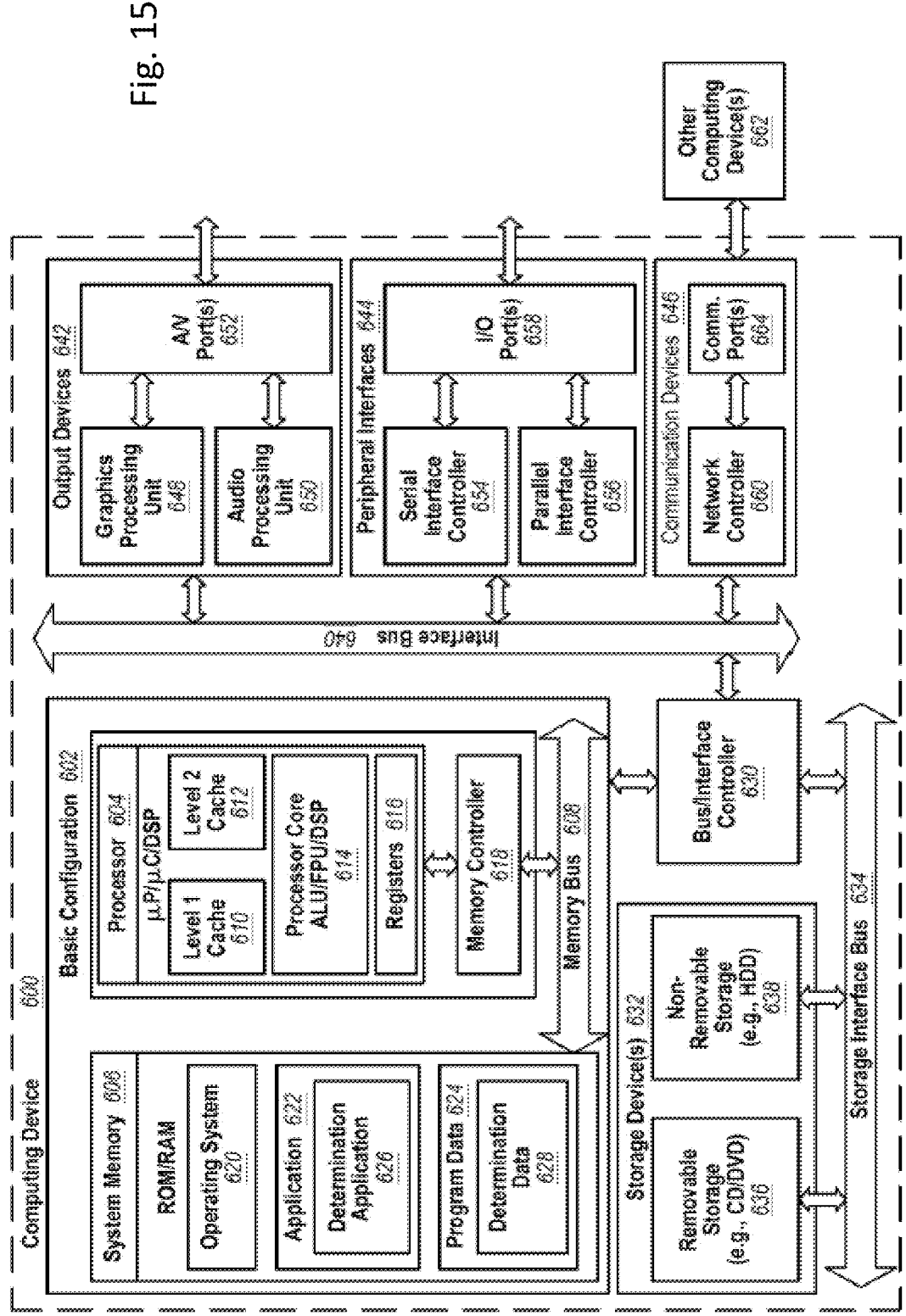
FIG. 15 shows an example of a computing system for performing the computing methods described herein.

FIG. 15 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (μP), a microcontroller (μC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and or an experimental protocol for validating the molecule. Other executable instructions may also be provided.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

ABBREVIATIONS

DCM dichloromethane
DMF dimethylformamide

DMSO dimethylsulphoxide
EA ethyl acetate
HPLC high performance liquid chromatography methanol
PBS phosphate buffered saline
THE tetrahydrofuran
TFA trifluoroacetic acid
TLC thin layer chromatography
Py pyridine
EDCI 1-ethyl-3-(3-dimethylaminopropyl)carbodiimide
ACN acetonitrile
T3P 1-Propanephosphonic anhydride solution
Pd(dppf)Cl2 [1,1'-Bis(diphenylphosphino)ferrocene]dichloropalladium(II)
NIS N-Iodosuccinimide
TEA triethylamine
TFA trifluoroacetic acid
HATU 1-[Bis(dimethylamino)methylene]-1H-1,2,3-triazolo[4,5-b]pyridinium 3-oxid hexafluorophosphate
DIEA diisopropylethylamine
NMP N-Methyl-2-pyrrolidone
XPhos Pd G3 (2-Dicyclohexylphosphino-2',4',6'-triisopropyl-1,1'-biphenyl)[2-(2'-amino-1,1'-biphenyl)]palladium(II) methanesulfonate
MTBE Methyl-tert-butyl ether
CDI 1,1'-Carbonyldiimidazole This patent cross-references: U.S. application Ser. No. 16/015,990 filed Jun. 2, 2018; U.S. application Ser. No. 16/134,624 filed Sep. 18, 2018; U.S. Application No. 62/727,926 filed Sep. 6, 2018; U.S. Application No. 62/746,771 filed Oct. 17, 2018; and U.S. Application No. 62/809,413 filed Feb. 22, 2019; which applications are incorporated herein by specific reference in their entirety.

All references recited herein are incorporated herein by specific reference in their entirety.

1. Paul, S. M. et al. How to improve R&D productivity: the pharmaceutical industry's grand challenge. *Nat. Rev. Drug Discov.* 9, 203-214 (2010).
2. Avorn, J. The $2.6 Billion Pill Methodologic and Policy Considerations. N. *Engl. J. Med.* 372, 1877-1879 (2015).
3. Fleming, N. How artificial intelligence is changing drug discovery. *Nature* 557, S55 (2018).
4. Chen, H., Engkvist, O., Wang, Y., Olivecrona, M. & Blaschke, T. The rise of deep learning in drug discovery. *Drug Discov. Today* 23, 1241-1250 (2018).
5. Butler, K. T., Davies, D. W., Cartwright, H., Isayev, O. & Walsh, A. Machine learning for molecular and materials science. *Nature* 559, 547-555 (2018).
6. Segler, M. H. S., Preuss, M. & Waller, M. P. Planning chemical syntheses with deep neural networks and symbolic AI. *Nature* 555, 604-610 (2018).
7. De Fauw, J. et al. Clinically applicable deep learning for diagnosis and referral in retinal disease. *Nat. Med.* 24, 1342-1350 (2018).
8. Wang, K., Wan, M., Wang, R.-S. & Weng, Z. Opportunities for Web-based Drug Repositioning: Searching for Potential Antihypertensive Agents with Hypotension Adverse Events. *J. Med. Internet Res.* 18, e76 (2016).
9. Mamoshina, P., Vieira, A., Putin, E. & Zhavoronkov, A. Applications of Deep Learning in Biomedicine. *Mol. Pharm.* 13, 1445-1454 (2016).
10. Baskin, I. I., Winkler, D. & Tetko, I. V. A renaissance of neural networks in drug discovery. *Expert Opin. Drug-Discov.* 11, 785-795 (2016).
11. Zhang, L., Tan, J., Han, D. & Zhu, H. From machine learning to deep learning: progress in machine intelligence for rational drug discovery. *Drug Discov. Today* 22, 1680-1685 (2017).
12. Goodfellow, I. et al. Generative Adversarial Nets. in *Advances in Neural Information Processing Systems* 2672-2680 (2014).
13. Sanchez-Lengeling, B. & Aspuru-Guzik, A. Inverse molecular design using machine learning: Generative models for matter engineering. *Science* 361, 360-365 (2018).
14. Kadurin, A. et al. The cornucopia of meaningful leads: Applying deep adversarial autoencoders for new molecule development in oncology. *Oncotarget* 8, 10883-10890 (2017).
15. Kadurin, A., Nikolenko, S., Khrabrov, K., Aliper, A. & Zhavoronkov, A. druGAN: An Advanced Generative Adversarial Autoencoder Model for de Novo Generation of New Molecules with Desired Molecular Properties in Silico. *Mol. Pharm.* 14, 3098-3104 (2017).
16. Gómez-Bombarelli, R. et al. Automatic Chemical Design Using a Data-Driven Continuous Representation of Molecules. *ACS Cent. Sci.* 4, 268-276 (2018).
17. Putin, E. et al. Adversarial Threshold Neural Computer for Molecular de Novo Design. *Mol. Pharm.* 15, 4386-4397 (2018).
18. Putin, E. et al. Reinforced Adversarial Neural Computer for de Novo Molecular Design. *J. Chem. Inf. Model.* 58, 1194-1204 (2018).
19. Harel, S. & Radinsky, K. Prototype-Based Compound Discovery Using Deep Generative Models. *Mol. Pharm.* 15, 4406-4416 (2018).
20. Polykovskiy, D. et al. Entangled Conditional Adversarial Autoencoder for de Novo Drug Discovery. *Mol. Pharm.* 15, 4398-4405 (2018).
21. Kuzminykh, D. et al. 3D Molecular Representations Based on the Wave Transform for Convolutional Neural Networks. *Mol. Pharm.* 15, 4378-4385 (2018).
22. Segler, Marwin H S and Kogej, Thierry and Tyrchan, Christian and Waller, Mark P. Generating focused molecule libraries for drug discovery with recurrent neural networks. ACS central science 4.1 (2017): 120-131.
23. Merk, Daniel and Friedrich, Lukas and Grisoni, Francesca and Schneider, Gisbert. De novo design of bioactive small molecules by artificial intelligence. Molecular informatics 37.1-2 (2018): 1700153
24. Merk, Daniel and Grisoni, Francesca and Friedrich, Lukas and Schneider, Gisbert. Tuning artificial intelligence on the de novo design of natural-product-inspired retinoid X receptor modulators. Communications Chemistry 1.1 (2018): 68.
25. Sutton, R. S. & Barto, A. G. *Reinforcement Learning: An Introduction*. (MIT Press, 1998).
26. Sutton, R. S., McAllester, D., Singh, S. & Mansour, Y. Policy gradient methods for reinforcement learning with function approximation. in *Proceedings of the 12th International Conference on Neural Information Processing Systems* 1057-1063 (MIT Press, 1999).
27. Yu, L., Zhang, W., Wang, J. & Yu, Y. SeqGAN: Sequence Generative Adversarial Nets with Policy Gradient. Preprint at arxiv.org/abs/1609.05473 (2017).
28. Sohn, K., Lee, H. & Yan, X. Learning Structured Output Representation using Deep Conditional Generative Models. in *Advances in Neural Information Processing Systems* 3483-3491 (2015).
29. Tomczak, J. M. & Welling, M. VAE with a VampPrior. *Proceedings of the 21st International Conference on Artificial Intelligence and Statistics (AISTATS)* (2017).
30. Imaizumi, M., Maehara, T. & Hayashi, K. On Tensor Train Rank Minimization Statistical Efficiency and Scalable Algorithm. in *Advances in Neural Information Processing Systems* 3930-3939 (2017).
31. Novikov, A., Rodomanov, A., Osokin, A. & Vetrov, D. Putting MRFs on a Tensor Train. In *International Conference on Machine Learning* 811-819 (2014).
32. Oseledets, I. V. Tensor-Train Decomposition. *SIAM J. Sci. Comput.* 33, 2295-2317 (2011).
33. Kingma, D. P. & Welling, M. Auto-Encoding Variational Bayes. Preprint at arxiv.org/abs/1312.6114 (2013).
34. Makhzani, A., Shlens, J., Jaitly, N., Goodfellow, I. & Frey, B. Adversarial Autoencoders. Preprint at arxiv.org/abs/1511.05644 (2015).
35. Kingma, D. P., Mohamed, S., Rezende, D. J. & Welling, M. Semi-supervised Learning with Deep Generative Models. in *Advances in Neural Information Processing Systems* 3581-3589 (2014).
36. Leo, A. J. Calculating log Poet from structures. *Chem. Rev.* 93, 1281-1306 (1993).
37. Bickerton, G. R., Paolini, G. V., Besnard, J., Muresan, S. & Hopkins, A. L. Quantifying the chemical beauty of drugs. *Nat. Chem.* 4, 90-98 (2012).
38. Guimaraes, G. L., Sanchez-Lengeling, B., Farias, P. L. C. & Aspuru-Guzik, A. Objective-Reinforced Generative Adversarial Networks (ORGAN) for Sequence Generation Models. Preprint at arxiv.org/abs/1705.10843 (2017).
39. Sanchez-Lengeling, B., Outeiral, C., Guimaraes, G. L. & Aspuru-Guzik, A. Optimizing distributions over molecular space. An Objective-Reinforced Generative Adversarial Network for Inverse-design Chemistry (ORGANIC). Preprint at chemrxiv.org/articles/ORGANIC_1_pdf/5309668 (2017).
40. Kohonen, T. The self-organizing map. *Proc. IEEE* 78, 1464-1480 (1990).
41. Wassermann, A. M., Camargo, L. M. & Auld, D. S. Composition and applications of focus libraries to phenotypic assays. *Front. Pharmacol.* 5, 164 (2014).
42. Szymanski, P., Markowicz, M. & Mikiciuk-Olasik, E. Adaptation of High-Throughput Screening in Drug Discovery-Toxicological Screening Tests. *Int. J. Mol. Sci.* 13, 427-452 (2011).
43. Morgan, P. et al. Impact of a five-dimensional framework on R&D productivity at AstraZeneca. *Nat. Rev. Drug Discov.* 17, 167-181 (2018).
44. Cong, L., Xia, Z.-K. & Yang, R.-Y. Targeting the TGF-β receptor with kinase inhibitors for scleroderma therapy. *Arch. Pharm.* 347, 609-615 (2014).
45. Liu, L. et al. Synthesis and biological evaluation of novel dasatinib analogues as potent DDR1 and DDR2 kinase inhibitors. *Chem. Biol. Drug Des.* 89, 420-427 (2017).
46. Drug Discovery I boehringer-ingelheim.com. Available at: boehringer-ingelheim.com/innovation/drug-discovery. (Accessed: 30 Oct. 2018).
47. Scannell, J. W., Blanckley, A., Boldon, H. & Warrington, B. Diagnosing the decline in pharmaceutical R&D efficiency. *Nat. Rev. Drug Discov.* 11, 191-200 (2012).
48. Munos, B. Lessons from 60 years of pharmaceutical innovation. *Nat. Rev. Drug Discov.* 8, 959-968 (2009).
49. Clarivate Analytics Integrity. Available at: integrity.thomson-pharma.com/integrity/xmlxsl/. (Accessed: 30 Oct. 2018).
50. EBI Web Team. ChEMBL. Available at: ebi.ac.uk/chembl/. (Accessed: 30 Oct. 2018).
51. Irwin, J. J., Sterling, T., Mysinger, M. M., Bolstad, E. S. & Coleman, R. G. ZINC: a free tool to discover chemistry for biology. *J. Chem. Inf. Model.* 52, 1757-1768 (2012).
52. Trepalin S V, E. al. New diversity calculations algorithms used for compound selection. *J. Chem. Inf. Comput. Sci.* 42, 249-258 (2002).
53. Top 25 Global Pharma Companies by Market Cap (end of 2017) GlobalData Plc. (2018). Available at: globaldata.com/top-25-global-pharma-companies-market-cap-end-2017/. (Accessed: 30 Oct. 2018).
54. Oseledets, I. V. Tensor-Train Decomposition. *SIAM J. Sci. Comput.* 33, 2295-2317 (2011).
55. Williams, R. J. Simple statistical gradient-following algorithms for connectionist reinforcement learning. *Mach. Learn.* 8, 229-256 (1992).
56. Brown N, Fiscato M, Segler M. H. S., Vaucher A. C. GuacaMol: Benchmarking Models for De Novo Molecular Design arXiv preprint arXiv:1811.09621 (2018).
57. Polykovskiy, D et al., Molecular Sets (MOSES): A Benchmarking Platform for Molecular Generation Models. arXiv preprint arXiv:1811.12823 (2018).
58. Ritter, H. & Kohonen, T. Self-organizing semantic maps. *Biol. Cybern.* 61, 241-254 (1989).
59. Landrum, G. RDKit. Available at: rdkit.org. (Accessed: 30 Oct. 2018).
60. Moriwaki, H., Tian, Y.-S., Kawashita, N. & Takagi, T. Mordred: a molecular descriptor calculator. *J Cheminform.* 10, 4 (2018).
61. Ivanenkov, Y. A. & Khandarova, L. M. Advanced Artificial Intelligence Methods Used in the Design of Pharmaceutical Agents. in *Pharmaceutical Data Mining* 457-489 (Wiley, 2009).
62. Pletnev, I. V., Ivanenkov, Y. A. & Tarasov, A. V. Dimensionality Reduction Techniques for Pharmaceutical Data Mining. in *Pharmaceutical Data Mining* 423-455 (Wiley, 2009).
63. Sammon, J. W. A Nonlinear Mapping for Data Structure Analysis. *IEEE Trans. Comput.* C-18, 401-409 (1969).
64. Molport. Available at: molport.com/. (Accessed: 30 Oct. 2018).
65. Rappe, A. K., Casewit, C. J., Colwell, K. S., Goddard, W. A. & Skiff, W. M. UFF, a full periodic table force field for molecular mechanics and molecular dynamics simulations. *J. Am. Chem. Soc.* 114, 10024-10035 (1992).
66. Schrödinger|Maestro Suite. Available at: schrodinger.com. (Accessed: 30 Oct. 2018).
67. EurofinsPharma Discovery Services. Available at: eurofinsdiscoveryservices.com/catalogmanagement/viewitem/DDR1-Human-TK-Kinase-Enzymatic-Radiometric-Assay-10-uM-ATP-KinaseProfiler/14-942KP10. (Accessed: 30 Oct. 2018).
68. Eurofins Pharma Discovery Services. Available at: eurofinsdiscoveryservices.com/catalogmanagement/viewitem/scanMAX-Delta-Panel-10 uM-ATP/50-100KP10. (Accessed: 30 Oct. 2018).
69. Cho, Kyunghyun; van Merrienboer, Bart; Gulcehre, Caglar; Bahdanau, Dzmitry; Bougares, Fethi; Schwenk, Holger; Bengio, Yoshua. Learning Phrase Representations using RNN Encoder-Decoder for Statistical Machine Translation. Proceedings of the 2014 Conference on Empirical Methods in Natural Language Processing (EMNLP), pages 1724-1734 (2014).
70. Kingma D. P., Ba J. Adam: A method for stochastic optimization, 3rd International Conference for Learning Representations, 2015.
71. Ivanenkov Y A, Zagribelnyy B A, Aladinskiy V A. Are We Opening the Door to a New Era of Medicinal Chemistry or Being Collapsed to a Chemical Singularity? J Med Chem. 2019; 62: 10026-10043.

The invention claimed is:

1. A method, comprising:
receiving input of a biological target or ligand;
receiving input of properties of a generated compound;
receiving at least one generative model trained with reference compounds, the reference compounds identified from one or more groups of compounds based on the biological target or ligand and the properties of the generated compound;
generating structures of generated compounds with each generative model, based on the input of properties of the generated compound, wherein the generated compounds are designed to interact with the biological target and/or correlate with structural features of the ligand, wherein generating includes refining the generated compounds with a rewards function and performing pharmacophore modeling;
prioritizing structures of the generated compounds of each generative model based on at least one reward criteria;
processing prioritized chemical structures of the generated compounds through a Sammon mapping protocol to obtain hit structures, wherein the Sammon mapping protocol uses molecular descriptors applied in the rewards function and a root-mean-square deviation (RMSD) value from the pharmacophore modeling;
removing compounds that cannot be synthesized from the hit structures;
providing chemical structures of the synthesizable hit structures; and
synthesizing the chemical structures of the synthesizable hit structures.

2. The method of claim 1, further comprising:
receiving the reference compounds; and
training the generative model with the reference compounds.

3. The method of claim 1, further comprising at least one:
refining, with the generative model, structures with at least one reward function; or
performing a pharmacophore modeling with the generative model.

4. The method of claim 1, wherein the at least one reward criteria is determined to be satisfied by at least one of:
performing a molecular filtering operation on the generated compounds;
performing a clustering/diversifying operation on the generated compounds;
analyzing vendor compounds in view of the generated compounds;
performing a reward prioritization;
performing a root-mean-square deviation value determination for fit of generated compounds to the biological target; or
analyzing novelty of the generated compounds based on published intellectual property documents.

5. The method of claim 1, wherein the prioritizing structures includes performing a structure refining protocol with at least one Kohonen self-organizing map (SOM).

6. The method of claim 5, wherein the Kohonen SOM includes:
a trending SOM that rewards structures that are newer based on a chronological timeline compared to older structures;
a general biological target SOM that rewards a class of structures for a family of biological targets that include the biological target over other classes of structures without biological activity to the family of biological targets; and
a specific biological target SOM that rewards a structure that specifically targets the biological target.

7. The method of claim 1, further comprising performing a pharmacophore modeling with a generated compound to analyze a scaffold structure or pendant substituent structures of the generated compound, wherein the generated compound is modeled to interact with the biological target and/or modeled to correlate with structural features of the ligand.

8. The method of claim 1, further comprising:
generating a latent space manifold having a plurality of the reference compounds in the trained GENTRL model; and
generating new compounds with the trained GENTRL model that are not present in the latent space manifold.

9. The method of claim 1, wherein the prioritizing of the structures of generated compounds based on at least one reward criteria includes at least one of the following:
filtering compounds to meet a predefined range molecular descriptors;
applying a medicinal chemistry filter to remove compounds having undesirable medicinal chemistry properties;
applying Lipinski's Rule of Five to the compounds;
applying T-indexes to the compounds to eliminate structures with unbalanced number of carbons and heteroatoms;
applying a similarity filter to the compounds based on an assessment of 2D-similarity between the compounds and available chemical space;
applying a physicochemical profile filter to the compounds based on physicochemical properties;
applying a drug-likeness filter to the compounds based on a drug-likeness estimation;
applying a privileged structure filter to the compounds to prioritize fragments that are useful for a selected class of compounds or the biological target;
applying a synthetic accessibility filter to the compounds based on an assessment of the synthetic accessibility of the compounds;
applying a diversity filter to the compounds based on privileged fragments of structures;
applying a clustering filter to the compounds based on privileged fragments of structures;
applying a Tanimoto-based clustering and diversity to remove compounds having similar structures;
applying a trending SOM that selects structures that are newer based on a chronological timeline compared to older structures;
applying a general biological target SOM that selects structures that are biologically active for a family of biological targets that include the biological;
applying a specific biological target SOM that selects structures that specifically target the biological target; or
applying a pharmacophore filter to remove compounds that fail pharmacophore modeling.

10. The method of claim 1, further comprising screening the generated compounds for patentability.

11. The method of claim 1, further comprising obtaining at least one data set having the reference compounds including:
general compounds;
compounds that modulate the biological target;
compounds that modulate biomolecules other than the biological target;
patient data for a set of known compounds having a specific functional activity with the biological target; or chemical structure data for a set of known compounds having the specific functional activity with the biological target.

12. The method of claim 1, further comprising identifying an activity threshold for a specific functional activity in modulating the biological target, wherein generated compounds with less than the activity threshold are defined as inactive and compounds having the activity threshold or higher activity are defined as active compounds.

13. The method of claim 1, further comprising:
processing data sets of the reference compounds to exclude outlier compounds; and
normalize an input chemical space by reducing the number of compounds containing similar structures per each cluster of compounds.

14. The method of claim 1, further comprising:
identify a plurality of first compounds, the plurality of first compounds being part of a learned manifold of the first compounds;
parameterizing a structure of the learned manifold with a tensor train using partially known properties of the compounds, the partially known properties include known properties of the compounds; and
generating a plurality of second compounds, the second compounds being based on the first plurality of compounds, wherein the second compounds are the generated compounds.

15. The method of claim 1, further comprising:
identifying a predetermined range of molecular descriptors;
obtaining an output of generated compounds from the generative model; and
excluding compounds outside of the predetermined range to obtain a chemical space with the generated compounds within the predetermined range.

16. The method of claim 1, further comprising randomly selecting a number of generated compound from the Sammon mapping that cover a chemical space to obtain the hit structures.

* * * * *